US011701364B2

(12) United States Patent
Lairson et al.

(10) Patent No.: US 11,701,364 B2
(45) Date of Patent: Jul. 18, 2023

(54) AGONISTS OF STIMULATOR OF INTERFERON GENES STING

(71) Applicant: The Scripps Research Institute, La Jolla, CA (US)

(72) Inventors: Luke L. Lairson, San Diego, CA (US); Emily Chin, San Diego, CA (US); Arnab K. Chatterjee, San Diego, CA (US); Manoj Kumar, San Diego, CA (US); Ana Maria Gamo Albero, La Jolla, CA (US); Hank Michael James Petrassi, San Diego, CA (US); Peter G. Schultz, La Jolla, CA (US); Chenguang Yu, La Jolla, CA (US); Junko Tamiya, Carlsbad, CA (US); William Vernier, Vista, CA (US); Anil Gupta, San Diego, CA (US); Ramkumar Modukuri, Houston, TX (US)

(73) Assignee: The Scripps Research Institute, La Jolla, CA (US)

( * ) Notice: Subject to any disclaimer, the term of this patent is extended or adjusted under 35 U.S.C. 154(b) by 187 days.

(21) Appl. No.: 15/733,535

(22) PCT Filed: Feb. 21, 2019

(86) PCT No.: PCT/US2019/018899

§ 371 (c)(1),
(2) Date: Aug. 21, 2020

(87) PCT Pub. No.: WO2019/165032

PCT Pub. Date: Aug. 29, 2019

(65) Prior Publication Data

US 2021/0205321 A1 Jul. 8, 2021

Related U.S. Application Data

(60) Provisional application No. 62/633,409, filed on Feb. 21, 2018.

(51) Int. Cl.

| | |
|---|---|
| *A61K 31/5365* | (2006.01) |
| *A61K 9/19* | (2006.01) |
| *A61K 9/127* | (2006.01) |
| *A61K 31/501* | (2006.01) |
| *A61K 31/506* | (2006.01) |
| *A61K 31/536* | (2006.01) |
| *A61K 45/06* | (2006.01) |
| *A61K 47/68* | (2017.01) |
| *A61K 9/00* | (2006.01) |

(52) U.S. Cl.

CPC ........ *A61K 31/5365* (2013.01); *A61K 9/0019* (2013.01); *A61K 9/0053* (2013.01); *A61K 9/127* (2013.01); *A61K 31/501* (2013.01); *A61K 31/506* (2013.01); *A61K 31/536* (2013.01); *A61K 45/06* (2013.01); *A61K 47/6803* (2017.08)

(58) Field of Classification Search

CPC combination set(s) only.
See application file for complete search history.

(56) References Cited

U.S. PATENT DOCUMENTS

| | | | | |
|---|---|---|---|---|
| 2012/0202787 A1* | 8/2012 | am Ende | ................ | A61P 21/00 544/405 |
| 2017/0158724 A1 | 6/2017 | Adams et al. | | |

FOREIGN PATENT DOCUMENTS

| | | |
|---|---|---|
| CN | 103204813 | 7/2013 |
| CN | 111971045 | 11/2020 |
| EA | 201692119 | 6/2017 |
| IN | 202017036638 | 10/2020 |
| JP | 2021514375 | 6/2021 |
| JP | 2022130684 | 9/2022 |
| WO | 2011048525 | 4/2011 |
| WO | WO-2017027646 A1 | 2/2017 |
| WO | WO-2019165032 A1 | 8/2019 |

OTHER PUBLICATIONS

Parker et al., "Antitumour actions of interferons: implications for cancer therapy," Nature Reviews Cancer vol. 16, pp. 131-144 (2016). (Year: 2016).*

Stuart, Webmd article, https://www.webmd.com/cancer/immunotherapy-different-cancers (evidentiary) 2021. (Year: 2021).*

Crunkhorn, "Immunotherapy opportunity emerges for Alzheimer disease," Nature Reviews Neurology Jan. 29, 2016). (Year: 2016).*

Naidoo et al., "Toxicities of the anti-PD-1 and anti-PD-L1 immune checkpoint antibodies," Annals of Oncology, vol. 26, Issue 12, Dec. 1, 2015, pp. 2375-2391. (Year: 2105).*

"Australian Application Serial No. 2019225919, First Examination Report dated Apr. 28, 2021", 3 pgs.

Anonymous, "N-(2,3-Dichlorophenyl)-6-(2-methylimidazol-1-yl)pyridazine-3-carboxamide", Pubchem Compound Database accession No. CID71791784, (Nov. 14, 2013), 6 pages.

Anonymous, "6-(2-Methylimidazol-1 -yl)-N-[4-(trifluoromethoxy)phenyl]pyridazine-3-carboxamide", Pubchem Compound Database accession No. CID71791787, (Nov. 14, 2013), 7 pages.

Anonymous, "Methyl 2-(6-(1H-imidazol-1-yl)pyridazine-3-carboxamido)benzoate", Pubchem Compound Database accession No. CID71791731, (Nov. 14, 2013), 6 pages.

"Canadian Application Serial No. 3,091,670, Response filed Jan. 12, 2022 to Office Action dated Oct. 8, 2021", 209 pages.

(Continued)

*Primary Examiner* — Jared Barsky

(74) *Attorney, Agent, or Firm* — Jennifer Kisko; Hugh Wang

(57) ABSTRACT

The invention provides compounds having STimulator of INterferon Genes (STING) agonistic bioactivity that can be used in the treatment of tumors in patients afflicted therewith. The compounds are of formula (I): as defined herein. Compounds for practice of a method of the invention can be delivered via oral delivery for systemic exposure, as well as delivered intratumorally. Antitumor therapy using a compound of formula (I) can further comprise administration of an effective dose of an immune-checkpoint targeting drug.

14 Claims, 3 Drawing Sheets

(56) References Cited

OTHER PUBLICATIONS

"Australian Application Serial No. 2019225919, Response filed Mar. 11, 2022 to First Examination Report dated Apr. 28, 2021", 236 pages.
"Canadian Application Serial No. 3,091,670, Office Action dated Oct. 8, 2021", 3 pages.
"European Application Serial No. 19757913.9, Extended European Search Report dated Oct. 19, 2021", 8 pages.
"Database Pubchem Compound [Online]", Registry entry 1797956-58-1 and further compounds, (Jan. 1, 2015) 7 pages.
"Japanese Application Serial No. 2020-544275, Notification of Reasons for Refusal dated Nov. 8, 2021", with English translation, 6 pages.
Anonymous, "SID 336981916—PubChem", Pubchem, (Jan. 1, 2017), pp. 1-6.
"Mexican Application Serial No. MX a 2020 008771, Office Action dated Sep. 4, 2020", with machine English translation, 7 pages.
"European Application Serial No. 19757913.9, Response filed May 18, 2022 to Extended European Search Report dated Oct. 19, 2021", 162 pgs.
"Mexican Application Serial No. MX/a/2020 008771, Office Action dated Oct. 12, 2022", w/ English Machine Translation, 8 pgs.
"Russian Application Serial No. 2020130864, Official Action dated Aug. 19, 2022", w/ English Translation, 25 pgs.
"PubChem CID 71791730", (Nov. 14, 2013), 9 pgs.
"PubChem CID 121114373", (Jun. 20, 2016), 8 pgs.
"Russian Application Serial No. 2020130864, Response filed Dec. 12, 2022 to Official Action dated Aug. 19, 2022", w/ English claims, 52 pgs.
"International Application No. PCT/US2019/018899, International Search Report and Written Opinion dated Apr. 29, 2019", (Apr. 29, 2019), 7 pgs.
"Pubchem CID 71791731", Create Date Nov. 14, 2013; p. 2, see 2D structure, (Nov. 14, 2013), 1-6.
"Pubchem CID 71791784", Create Date Nov. 14, 2013; p. 2, see 2D structure, (Nov. 14, 2013), 1-6.
"Pubchem CID 71791787", Create Date Nov. 14, 2013; p. 2, see 2D structure, (Nov. 14, 2013), 1-7.
Ager, Casey R., et al., "Intratumoral STING activation with T-cell checkpoint modulation generates systemic antitumor immunity", Cancer Immunol Res. Aug. 2017; 5(8): 676-684, (Aug. 2017), 676-684.
Ariyan, Charlotte E., et al., "Robust Antitumor Responses Result from Local Chemotherapy and CTLA-4 Blockade", Cancer Immunol Res; 6(2) Feb. 2018, (Jan. 16, 2018), 189-200.
Corrales, Leticia, et al., "Direct Activation of STING in the Tumor Microenvironment Leads to Potent and Systemic Tumor Regression and Immunity", Cell Reports 11, 1018-1030, (May 19, 2015), 1018-1030.
Corrales, Leticia, et al., "Innate immune signaling and regulation in cancer immunotherapy", Cell Research (2017) 27:96-108, (Dec. 16, 2016), 96-108.
Corrales, Leticia, et al., "The host STING pathway at the interface of cancer and immunity", J Clin Invest. 2016;126(7):2404-2411, (Jul. 2016), 2404-2411.
Deng, Liufu, et al., "STING-dependent Cytosolic DNA Sensing Promotes Radiationinduced Type I interferon-dependent Antitumor Immunity in Immunogenic Tumors", Immunity. Nov. 20, 2014; 41(5): 843-852, (Nov. 20, 2014), 843-852.
Fu, Juan, et al., "STING agonist formulated cancer vaccines can cure established tumors resistant to PD-1 blockade", Sci Transl Med. Apr. 15, 2015; 7(283): 283ra52, (Apr. 15, 2015), 24 pgs.
Mackenzie, Karen J., et al., "cGAS surveillance of micronuclei links genome instability to innate immunity", Nature. Aug. 24, 2017; 548(7668): 461-465, (Aug. 24, 2017), 461-465.
Song, Chung Kil, et al., "Chemotherapy Enhances CD8+ T Cell-mediated Antitumor immunity Induced by Vaccination with Vaccinia Virus", www.moleculartherapy.org vol. 15, No. 8, 1558-1563, (Aug. 2007), 1558-1563.
Wang, Hua, et al., "cGAS is essential for the antitumor effect of immune checkpoint blockade", PNAS | Feb. 14, 2017 | vol. 114 | No. 7, (Feb. 14, 2017), 1637-1642.
Wang, Weimin, et al., "Effector T Cells Abrogate Stroma-Mediated Chemoresistance in Ovarian Cancer", Cell. May 19, 2016; 165(5): 1092-1105, (May 19, 2016), 1092-1105.
Sivick, Kelsey E., et al., "Magnitude of Therapeutic STING Activation Determines CD8+ T Cell-Mediated Anti-tumor Immunity", Cell Reports 25, 3074-3085, (Dec. 11, 2018), 3074-3085.
Woo, Seng-Ryong, et al., "STING-Dependent Cytosolic DNA Sensing Mediates Innate Immune Recognition of Immunogenic Tumors", Immunity 41, 830-842, (Nov. 20, 2014), 830-842.
"Mexican Applcation Serial No. MX a 2020 008771, Response fled Dec. 16, 22 to Office Action dated Oct. 12, 2022", w/ English claims, 50 pgs.
"Chinese Application Serial No. 201980021235.X, Office Action dated Jan. 12, 2023", w/ English Translation, 13 pgs.
"Israel Application Serial No. 276844, Notification of Defects in Patent Application dated Jan. 31, 2023", 5 pgs.
"Russian Application Serial No. 2020130864, Office Action dated Feb. 9, 2023", w/ English Translation, 14 pgs.
Belikov, V. G, "The relationship between the chemical structure, properties of agents and their effect on the organism", Pharmaceutical Chemistry Chapter 2.6, M.: MEDpress-inform, (2007), 27-29.

* cited by examiner

A.

B.

C.

| Compound | $T_m$ (°C) | $\Delta T_m$ (°C) |
|---|---|---|
| water | 43 | |
| 2'3'-cGAMP | 45.9 | 2.9 |
| DMSO | 42.5 | |
| 181 | 44.3 | 1.8 |

AGONISTS OF STIMULATOR OF INTERFERON GENES STING

CROSS-REFERENCE TO RELATED APPLICATION

This application is a U.S. national stage filing under 35 U.S.C. § 371 from International Application No. PCT/US2019/018899, filed on 21 Feb. 2019, and published as WO2019/165032 on 29 Aug. 2019, which claims the priority of U.S. provisional application Ser. No. 62/633,409, filed 21 Feb. 2018, the benefit of priority of each of which is claimed herein, and which applications and publication are hereby incorporated herein by reference in their entirety.

STATEMENT OF GOVERNMENT SUPPORT

This invention was made with government support under grant number CA200970-02 awarded by the National Institutes of Health. The government has certain rights in the invention.

BACKGROUND

The cGAS-STING signaling pathway plays a critical role in the innate immune response that mammalian host cells mount to eliminate diverse DNA and RNA viruses. STING (Stimulator of Interferon Genes) is an endoplasmic reticulum (ER) resident signaling protein, partially localized to mitochondria-associated membranes, which is broadly expressed in both immune and non-immune cell types. In response to cyclic dinucleotides (CDNs), including 2'-3' cGAMP produced in response to cytosolic DNA by cyclic GMP-AMP synthase (cGAS), STING translocates to the perinuclear region where it rapidly induces type I interferon (IFN) and pro-inflammatory cytokine production in a TBK1-/IRF3-dependent fashion. STING has also been found to directly bind cytosolic DNA, although the physiological relevance of direct DNA sensing activity remains to be fully characterized.

Recent work has demonstrated that STING plays essential roles in immune responses to tumor cells. Efficient tumor-initiated T cell priming within the tumor microenvironment requires interferon-beta (IFN-b) production by resident dendritic cells and the expression of IFN-b has been demonstrated to be dependent upon activation of the STING pathway (1). Indeed, intratumoral delivery of nucleotide-based STING agonists have been demonstrated to induce the profound regression of established tumors in syngeneic mouse models (1). In addition, activation of the STING pathway has also been demonstrated to significantly contribute to the anti-tumor effect of radiation, via IFN-b mediated immune response within the irradiated tumor microenvironment.

SUMMARY

In various embodiments, the invention provides an agonist of the Stimulator of Interferon Genes (STING), which can be used in the treatment of tumors.

For instance, the invention can provide a method of stimulating expression of interferon genes, comprising administering to a patient an effective dose of an agonist of the Stimulator of Interferon Genes (STING), comprising a compound of formula (I) (below), and a method of treating a tumor in a patient, comprising administering to the patient an effective dose of an agonist of the Stimulator of Interferon Genes (STING), comprising a compound of formula (I)

(I)

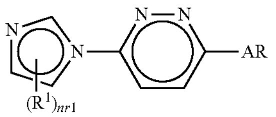

wherein each $R^1$ is independently (C1-C4)alkyl, or CN, nr1 is 0, 1, 2, or 3, provided that each $R^1$ is bonded to a carbon atom; and, AR is a group of formula —C(═O)N(R)$Ar^1$;

wherein $Ar^1$ is chosen from the group consisting of:

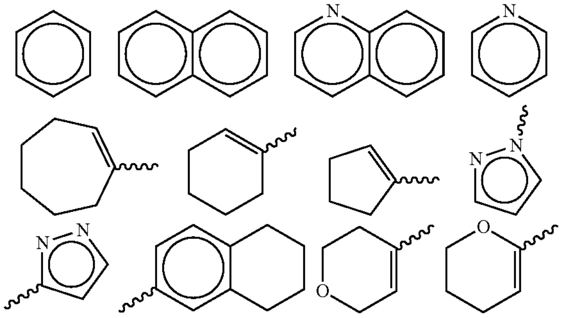

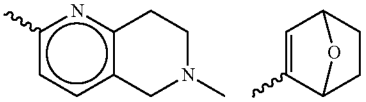

and

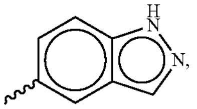

wherein a wavy line indicates a position of bonding;

wherein any $Ar^1$ is substituted with nr2 independently selected $R^2$ groups chosen from the group consisting of:

—(C1-C4)-alkyl, —(C1-C4)-alkylO, —(C1-C4)-alkylOC(O), —CN, -halo, —(C3-C7)cycloalkyl, —(C1-C4)-alkOC(O), —COOH, (C3-C7)-cycloalkylOC(O), —CN, —F, —Cl, —$SF_5$, -methylenedioxy, -difluoromethylenedioxy, -ethylenedioxy, —$CF_3$, —$OCF_3$, —C(O)$NH_2$, —C(O)NH$(CH_2)_2$OH, —$CH_2$OH, —$NR_2$, —C(/)ONH-arginine, —C(O)O$(CH_2)_2NR_2$,

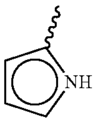

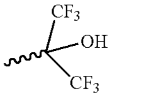

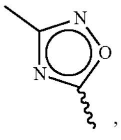

,

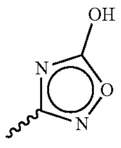

, and

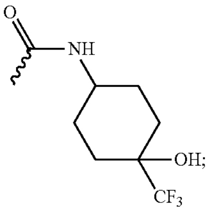

wherein a wavy line indicates a position of bonding; and, nr2=0, 1, 2, or 3;

or,

AR is a group of formula

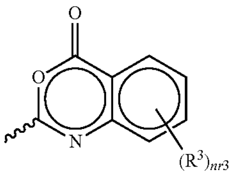

wherein $R^3$ is selected from the group consisting of (C1-C4)-alkyl, (C1-C4)-alkylO, (C1-C4)-alkylOC(O), CN, halo, (C3-C7)cycloalkyl, (C1-C4)-alkOC(O), COOH, (C3-C7)-cycloalkylOC(O), CN, F, Cl, —$SF_5$, methylenedioxy, difluoromethylenedioxy, ethylenedioxy, $CF_3$, —$OCF_3$, $CONH_2$, $CONH(CH_2)_2OH$, $CH_2OH$, $NR_2$, CONH-arginine, and $C(O)O(CH_2)_2NR_2$; and nr3=0, 1, 2, or 3;

or a pharmaceutically acceptable salt thereof.

More specifically, the method can be carried out using a compound of formula (I), wherein n1 is 0; or n1 is 1 or 2 and $R^1$ is methyl.

More specifically, the method can be carried out using a compound of formula (I), wherein X is a methyl, ethyl, or isopropyl carboxylic ester. Further, the method can be carried out using a compound of formula (I), wherein X is a 1,1,1,3,3,3-hexafluoropropan-2-ol-2-yl group. Further, the method can be carried out using a compound of formula (I), wherein Ar is phenyl. Further, the method can be carried out using a compound of formula (I), Further, the method can be carried out using a compound of formula (I), wherein $R^2$ is independently selected fluoro, chloro, (C1-C4)alkyl, trifluoromethyl, or cyano, and n2 is 1 or 2; or two $R^2$ together form a methylenedioxy group.

Additionally, a method of the invention can be carried out using an effective dose of any one of the specific compounds disclosed in the application; see, for example, Tables 1, 2, and 5.

In various embodiments, the method of treatment of a tumor can further comprise administering an effective dose of the compound of formula (I) or of any of the specific compounds disclosed herein via oral or intratumoral administration, or both.

In various embodiments, the method of treatment of a tumor can further comprise administering an effective dose of the compound of formula (I) or of any of the specific compounds disclosed herein, wherein administering comprises administering the compound to the patient as an antibody-drug conjugate, or in a liposomal formulation.

In various embodiments, the method of treatment of a tumor can further comprise administering an effective dose of the compound of formula (I) or of any of the specific compounds disclosed herein, further comprising administration of an effective dose of an immune-checkpoint targeting drug. For example, the immune-checkpoint targeting drug can be an anti-PD-L1 antibody, anti-PD-1 antibody, anti-CTLA-4 antibody, or an anti-4-1BB antibody.

In various embodiments, the method of treatment of a tumor can further comprise administering an effective dose of the compound of formula (I) or of any of the specific compounds disclosed herein, further comprising administration of ionizing radiation or anticancer drugs.

The invention also can include a novel compound of formula (I) as disclosed and claimed herein.

Figure 1:
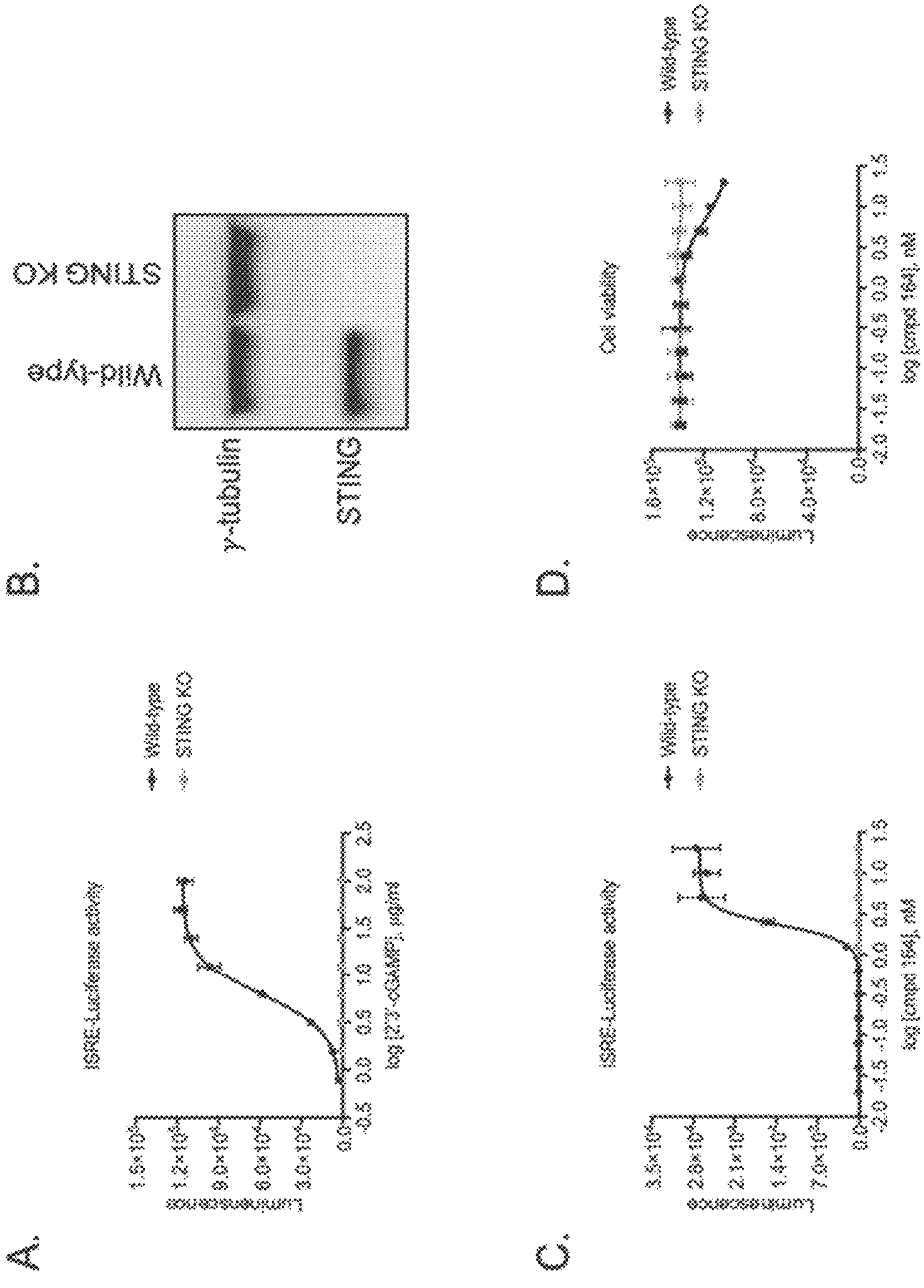
FIG. 1.
Figure 2:
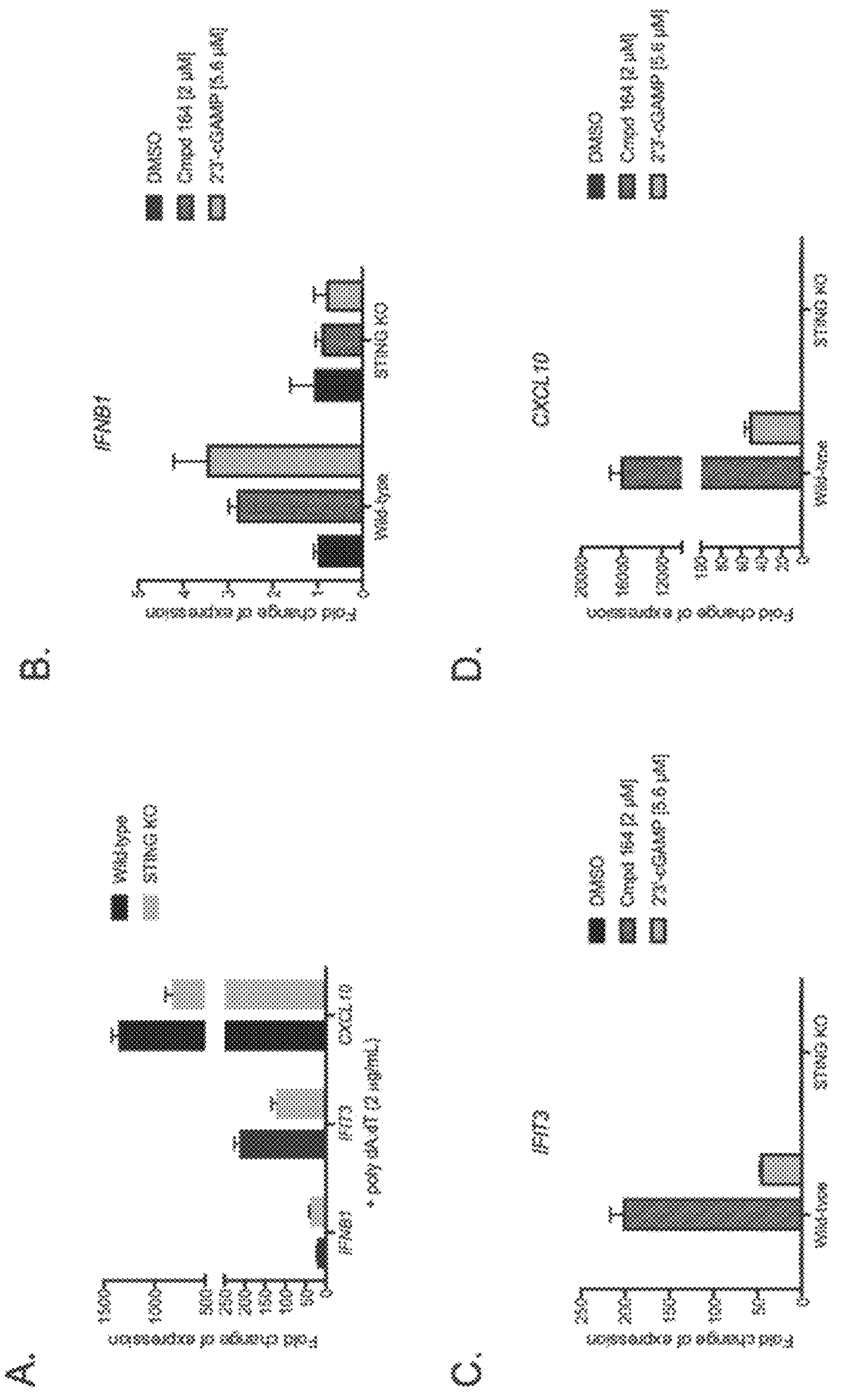
Figure 3:
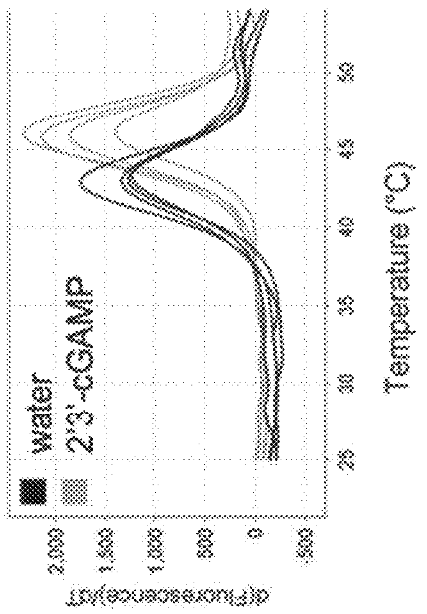
Figure 3:
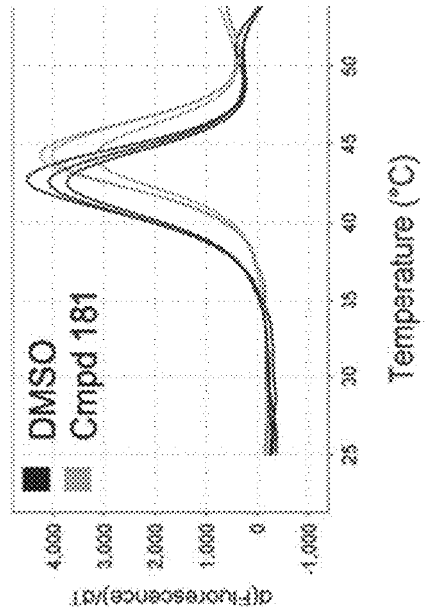

Wild-type and STING KO THP-1 ISRE-Luciferase reporter cells were treated with increasing doses of 2'3'-cGAMP and reporter activity (luminescence) was assessed 48 h after treatment (A). Lack of STING protein expression was confirmed in STING KO THP-1 cells by western blot with gamma-tubulin used as a protein loading control (B). Wild-type and STING KO THP-1 reporter cells were treated with increasing doses of Compound 164 (Cmpd 164) and reporter activity and cell viability were assessed 24 h after treatment (C-D).

FIG. 2:

Wild-type and STING KO THP-1 cells were stimulated with poly(dA:dT), a known activator of both RIG-I and cGAS-dependent signaling cascades, and downstream target gene expression was assessed 48 h later by qPCR (A). Wild-type and STING KO THP-1 cells were stimulated with 2'3'-cGAMP or Cmpd 164 at the indicated doses and activation of type I interferon signaling was assessed by gene expression analysis of IFNB1 (B) and interferon stimulated genes, IFIT3 (C) and CXCL10 (D).

FIG. 3:

The c-terminal domain of human STING protein (amino acids 138-379) was incubated with 2'3'-cGAMP [100 μM] (A) or Cmpd 181 [100 μM] (B) and 1× fluorescent dye followed by exposure to increasing temperature. The melting temperature ($T_m$) was calculated using the derivative method and the change in melting temperature ($\Delta T_m$) induced by ligand binding was obtained by normalizing to the appropriate vehicle control (C).

DETAILED DESCRIPTION

There is significant interest in the development of STING pathway agonists for diverse immuno-oncology applications. Most notably, STING pathway agonists have significant potential application as part of combination therapies involving immune-checkpoint targeting drugs, in patients that fail to respond to checkpoint blockade alone.

We have established a robust platform for identifying non-nucleotide small molecule STING agonists. This has been established using a primary assay involving a human THP-1 cell line carrying an IRF-inducible reporter with 5 copies of the IFN signaling response element. Counter screens, involving alternative reporter constructs, rodent cell-based assays, as well as cGAS and STING knock-out cell lines, are used to eliminate luciferase artifacts and ensure human-rodent cross species reactivity, as well as pathway selectivity. Biochemical assays, involving cGAS enzymatic activity and STING protein binding assays, are used to identify the specific target of identified hits. To date, from an initial screen of ~100,000 compounds we have identified at least one novel highly tractable bona fide STING agonist scaffold Compound 164, Table 1, $EC_{50}$~1 μM, Table 1), which induces interferon-stimulated gene signature expression in relevant cell types and type I IFN protein expression in human PBMCs with efficacy that is comparable to that observed for 2'-3' cGAMP. The observed activity of Compound 164, Table 1, in wild-type and cGAS knockout cells, as well as the observed lack of activity in STING knockout cells, provides evidence that this compound series functions by directly acting as STING agonists.

Further evidence is provided by STING protein thermal shift data. A preliminary medicinal chemistry effort, involving the design, synthesis, and testing of ~100 analogs within the series, has identified key features of the molecule that are required for activity and has led to the identification of derivatives with ~10-fold improvements in cell-based potency (by for example modulating the substitution pattern on the aniline ring) and ~50-fold improvement in plasma stability (by modulating the size of the substituent of the ester).

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents, or provides prophylaxis for, the disorder or condition. In particular, a "therapeutically effective amount" refers to an amount that is effective, at dosages and for periods of time necessary, to achieve the desired therapeutic result. A therapeutically effective amount is also one in which any toxic or detrimental effects of compounds of the invention are outweighed by the therapeutically beneficial effects.

The expression "effective amount", when used to describe therapy to an individual suffering from a disorder, refers to the quantity or concentration of a compound of the invention that is effective to inhibit or otherwise act on STING in the individual's tissues wherein STING involved in the disorder, wherein such inhibition or other action occurs to an extent sufficient to produce a beneficial therapeutic effect.

The term "pharmaceutically acceptable salts" refers to nontoxic inorganic or organic acid and/or base addition salts, see, for example, Lit et al., Salt Selection for Basic Drugs (1986), *Int J. Pharm.,* 33, 201-217, incorporated by reference herein.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by the same or differing halogen atoms, such as fluorine and/or chlorine atoms. Examples of haloalkyl include trifluoromethyl, 1,1-dichloroethyl, 1,2-dichloroethyl, 1,3-dibromo-3,3-difluoropropyl, perfluorobutyl, and the like.

Aryl groups are cyclic aromatic hydrocarbons that do not contain heteroatoms in the ring. An aromatic compound, as is well-known in the art, is a multiply-unsaturated cyclic system that contains 4n+2 π electrons where n is an integer. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Heterocyclyl groups or the term "heterocyclyl" includes aromatic and non-aromatic ring compounds containing 3 or more ring members, of which one or more ring atom is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C2-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. Ring sizes can also be expressed by the total number of atoms in the ring, e.g., a 3- to 10-membered heterocyclyl group, counting both carbon and non-carbon ring atoms. A heterocyclyl ring can also include one or more double bonds. A heteroaryl ring is an embodiment of a heterocyclyl group. The term "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The term also includes polycyclic, e.g., bicyclo- and tricyclo-ring systems containing one or more heteroatom such as, but not limited to, quinuclidyl. Heterocyclyl groups can be unsubstituted, or can be substituted.

Heteroaryl groups are heterocyclic aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure, which is a multiply-unsaturated cyclic system that contains 4n+2 π electrons wherein n is an integer. A heteroaryl group designated as a $C_2$-heteroaryl can be a 5-ring (i.e., a 5-membered ring) with two carbon atoms and three heteroatoms, a 6-ring (i.e., a 6-membered ring) with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms.

Examples of heteroaryl ring systems described herein include structural unit of formula

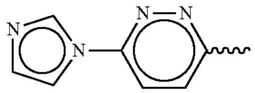

, an imidazolyl-pyridazine, which it is understand can also be portrayed as

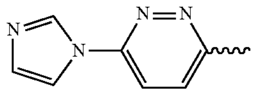

.

Another heteroaryl ring system described here is of formula

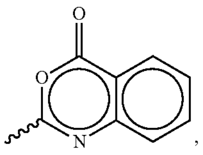

which it is understood can also be portrayed as

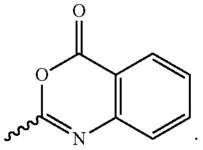

Similarly, other aryl (e.g., phenyl) and heteroaryl (e.g., pyridyl) ring systems described herein can be written either with the explicit double bonds, or with the aryl "circle" nomenclature, but the meanings are the same.

Cycloalkyl groups are groups containing one or more carbocyclic ring including, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

Heterocyclyl groups or the term "heterocyclyl" includes aromatic and non-aromatic ring compounds containing 3 or more ring members, of which one or more ring atom is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. Ring sizes can also be expressed by the total number of atoms in the ring, e.g., a 3- to 10-membered heterocyclyl group, counting both carbon and non-carbon ring atoms. A heterocyclyl ring can also include one or more double bonds. A heteroaryl ring is an embodiment of a heterocyclyl group. The term "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The term also includes polycyclic, e.g., bicyclo- and tricyclo-ring systems containing one or more heteroatom such as, but not limited to, quinuclidyl.

TABLE 1

Structures, bioactivities, and supporting structural data

| | Structure | ISG-LUC activation assay (EC50) [nM] | ISG-LUC activation assay (EC50) (Comment) | Analytical Data |
|---|---|---|---|---|
| 1 | 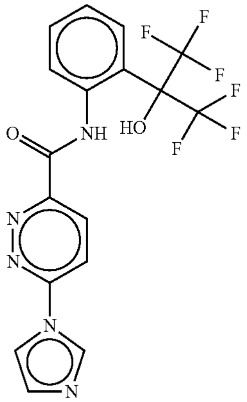 | 592.8 | ++++ | $^1H$ NMR (400 MHz, DMSO-$d_6$) δ 12.24 (s, 1H), 10.40 (s, 1H), 8.87 (s, 1H), 8.70 (d, J = 8.4 Hz, 1H), 8.59 (d, J = 9.2 Hz, 1H), 8.49 (d, J = 9.1 Hz, 1H), 8.23 (s, 1H), 7.75-7.48 (m, 2H), 7.39-7.28 (m, 2H). MS-ESI: m/z 432.3 observed $(M + H)^+$ |

TABLE 1-continued
| | Structures, bioactivities, and supporting structural data | | | |
|---|---|---|---|---|
| | Structure | ISG-LUC activation assay (EC50) [nM] | ISG-LUC activation assay (EC50) (Comment) | Analytical Data |
| 2 | 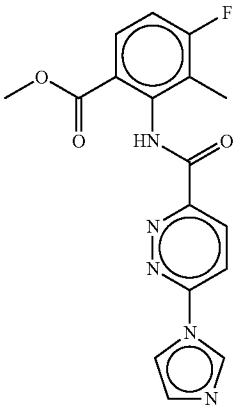 | 4686 | ++ | 1H NMR (400 MHz, DMSO-d6) δ 11.17 (s, 1H), 9.38 (s, 1H), 8.63-8.50 (m, 2H), 8.41 (s, 1H), 7.83 (dd, J = 8.8, 6.2 Hz, 1H), 7.60 (s, 1H), 7.39-7.24 (m, 1H), 3.72 (s, 5H), 2.20 (s, 3H). MS-ESI: m/z 356.32 observed $(M + H)^+$ |
| 3 | 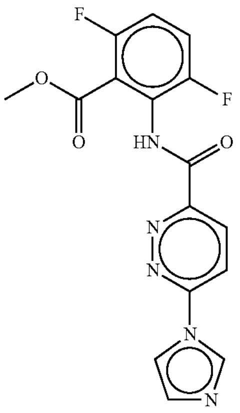 | 10187 | ++ | 1H NMR (400 MHz, DMSO-d6) δ 11.19 (s, 1H), 9.50 (s, 1H), 8.69-8.50 (m, 2H), 8.45 (d, J = 1.7 Hz, 1H), 7.74-7.58 (m, 2H), 7.58-7.32 (m, 1H), 3.78 (s, 3H). MS-ESI: m/z 360.27 observed $(M + H)^+$ |
| 4 | 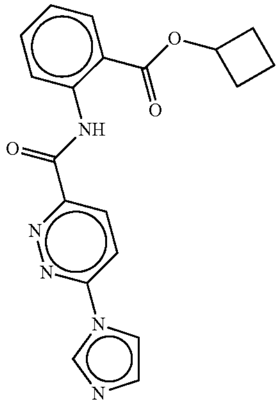 | 2067 | ++ | MS-ESI: m/z 364.29 observed $(M + H)^+$ |

TABLE 1-continued
Structures, bioactivities, and supporting structural data
| | Structure | ISG-LUC activation assay (EC50) [nM] | ISG-LUC activation assay (EC50) (Comment) | Analytical Data |
|---|---|---|---|---|
| 5 | 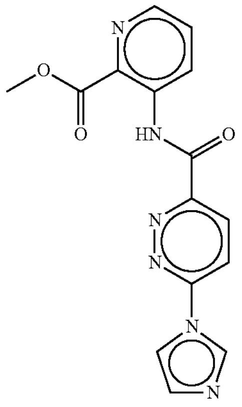 | 1243 | ++ | MS-ESI: m/z 325.3 observed $(M + H)^+$ |
| 6 | 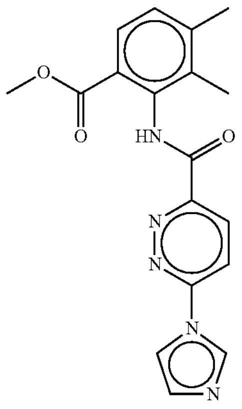 | ~2759 | ++ | MS-ESI: m/z 352.3 observed $(M + H)^+$ |
| 7 | 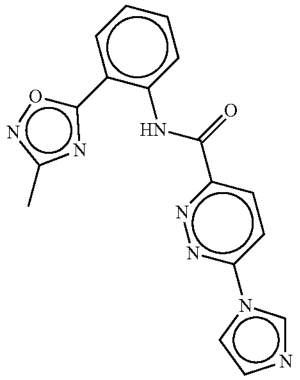 | >50000 | ++ | MS-ESI: m/z 348.41 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 8 | 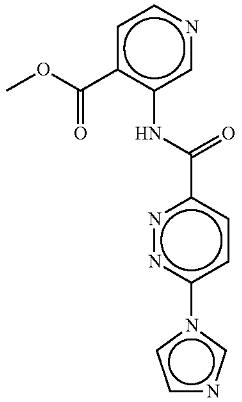 | 2571 | ++ | MS-ESI: m/z 325.36 observed $(M + H)^+$ |
| 9 | 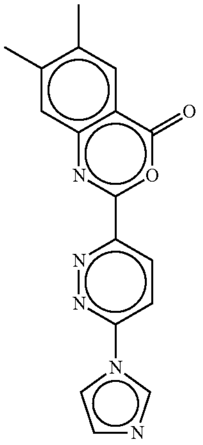 | 163.1 | ++++ | $^1H$ NMR (400 MHz, DMSO-$d_6$) δ 8.79 (s, 1H), 8.63 (d, J = 9.2 Hz, 1H), 8.42 (d, J = 9.2 Hz, 1H), 8.20 (s, 1H), 8.00 (s, 1H), 7.64 (s, 1H), 7.27 (s, 1H), 2.44 (s, 3H), 2.42 (s, 3H). MS-ESI: m/z 320.47 observed $(M + H)^+$ |
| 10 | 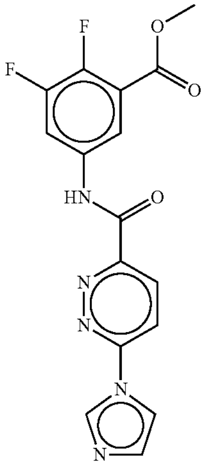 | 467.7 | ++++ | MS-ESI: m/z 360.04 observed $(M + H)^+$ |

TABLE 1-continued
Structures, bioactivities, and supporting structural data
| | Structure | ISG-LUC activation assay (EC50) [nM] | ISG-LUC activation assay (EC50) (Comment) | Analytical Data |
|---|---|---|---|---|
| 11 | 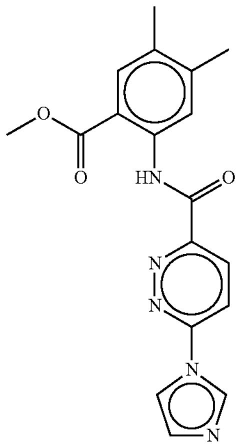 | 103.4 | ++++ | MS-ESI: m/z 352.3 observed $(M + H)^+$ |
| 12 | 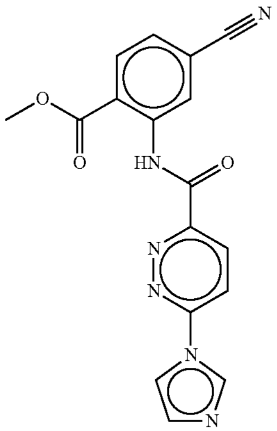 | 159 | ++++ | $^1H$ NMR (400 MHz, DMSO-d6) δ 13.05 (s, 1H), 9.33 (s, 1H), 9.14 (d, J = 1.6 Hz, 1H), 8.66 (d, J = 9.2 Hz, 1H), 8.55 (d, J = 9.2 Hz, 1H), 8.48-8.34 (m, 1H), 8.24 (d, J = 8.2 Hz, 1H), 7.77 (dd, J = 8.2, 1.7 Hz, 1H), 7.54 (s, 1H), 3.98 (s, 3H). MS-ESI: m/z 349.28 observed $(M + H)^+$ |
| 13 | 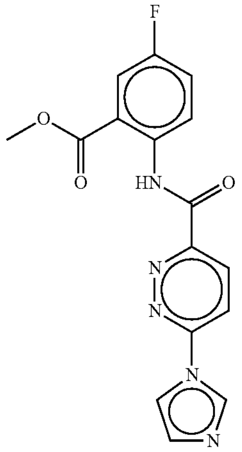 | 248.7 | ++++ | MS-ESI: m/z 342.25 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 14 | 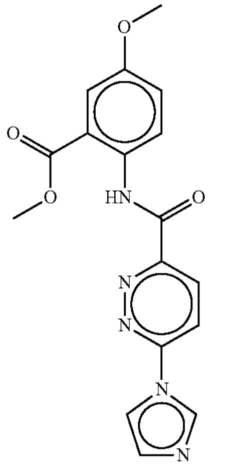 | 288.1 | ++++ | MS-ESI: m/z 354.31 observed $(M + H)^+$ |
| 15 | 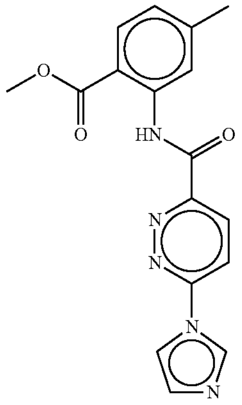 | 294.3 | ++++ | MS-ESI: m/z 338.36 observed $(M + H)^+$ |
| 16 | 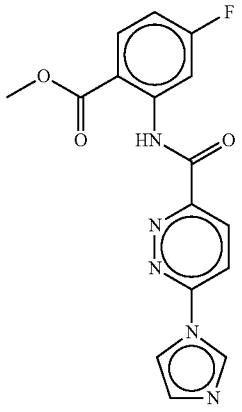 | 684.2 | ++++ | MS-ESI: m/z 342.25 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 17 | 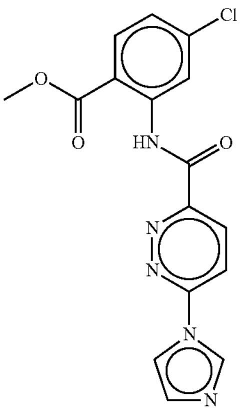 | 311.9 | ++++ | MS-ESI: m/z 358.2 observed (M + H)+ |
| 18 | 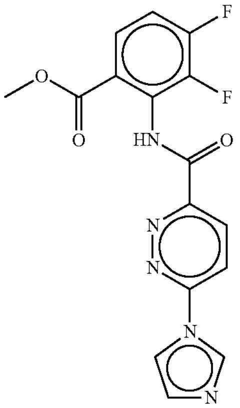 | 568.1 | ++++ | 1H NMR (400 MHz, DMSO-d6) δ 11.30 (s, 1H), 9.33 (s, 1H), 8.60 (d, J = 9.1 Hz, 1H), 8.53 (d, J = 9.1 Hz, 1H), 8.39 (s, 1H), 7.88-7.77 (m, 1H), 7.65-7.50 (m, 2H), 3.78 (s, 4H). MS-ESI: m/z 360.21 observed (M + H)+ |
| 19 | 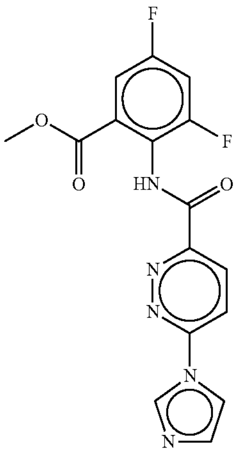 | 817.3 | ++++ | 1H NMR (400 MHz, DMSO-d6) δ 11.06 (s, 1H), 9.42 (s, 1H), 8.59 (d, J = 9.1 Hz, 1H), 8.53 (d, J = 9.1 Hz, 1H), 8.41 (s, 1H), 7.82-7.72 (m, 1H), 7.68-7.50 (m, 2H), 3.77 (s, 3H). MS-ESI: m/z 360.21 observed (M + H)+ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 20 | 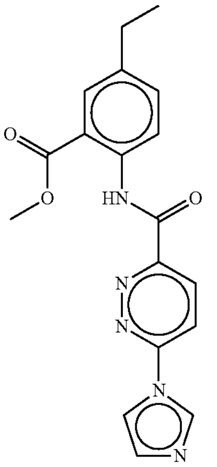 | 418.1 | ++++ | 1H NMR (400 MHz, DMSO-d6) δ 12.98 (s, 1H), 9.33 (s, 1H), 8.76 (d, J = 8.6 Hz, 1H), 8.62 (d, J = 9.1 Hz, 1H), 8.53 (d, J = 9.2 Hz, 1H), 8.41 (d, J = 1.6 Hz, 1H), 7.93 (d, J = 2.2 Hz, 1H), 7.61 (dd, J = 8.6, 2.2 Hz, 1H), 7.54 (s, 1H), 3.95 (s, 3H), 2.67 (q, J = 7.6 Hz, 2H), 1.21 (t, J = 7.6 Hz, 3H). MS-ESI: m/z 352.3 observed $(M + H)^+$ |
| 21 | 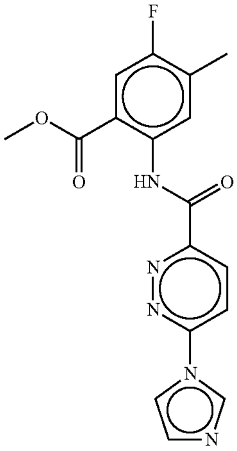 | 90.36 | ++++ | MS-ESI: m/z 356.25 observed $(M + H)^+$ |
| 22 | 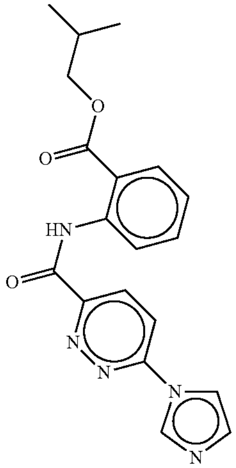 | 895.2 | ++++ | MS-ESI: m/z 366.3 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 23 | 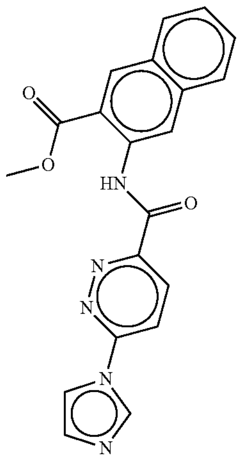 | 56.12 | ++++ | MS-ESI: m/z 374.28 observed $(M + H)^+$ |
| 24 | 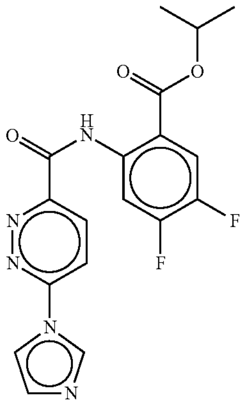 | 736.1 | ++++ | MS-ESI: m/z 388.28 observed $(M + H)^+$ |
| 25 | 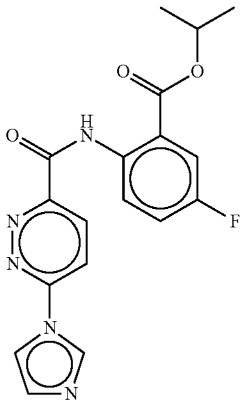 | 804.5 | ++++ | MS-ESI: m/z 370.26 observed $(M + H)^+$ |

TABLE 1-continued
Structures, bioactivities, and supporting structural data
| | Structure | ISG-LUC activation assay (EC50) [nM] | ISG-LUC activation assay (EC50) (Comment) | Analytical Data |
|---|---|---|---|---|
| 26 | 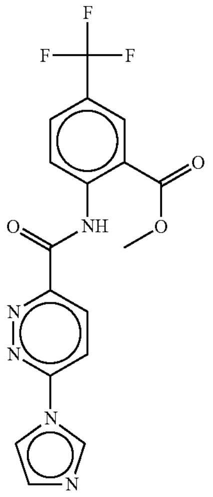 | 114 | ++++ | MS-ESI: m/z 392.37 observed $(M + H)^+$ |
| 27 | 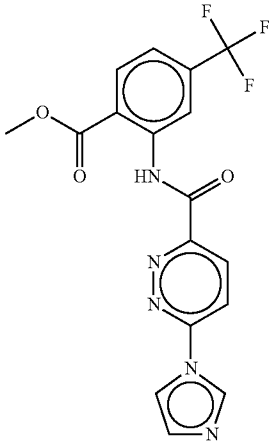 | 136.1 | ++++ | MS-ESI: m/z 392.37 observed $(M + H)^+$ |
| 28 | 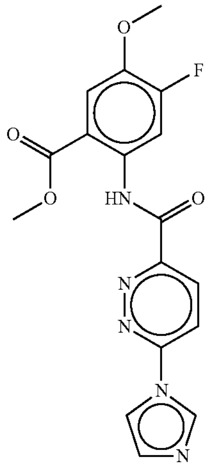 | 95.82 | ++++ | MS-ESI: m/z 372.33 observed $(M + H)^+$ |

TABLE 1-continued
Structures, bioactivities, and supporting structural data
| | Structure | ISG-LUC activation assay (EC50) [nM] | ISG-LUC activation assay (EC50) (Comment) | Analytical Data |
|---|---|---|---|---|
| 29 | 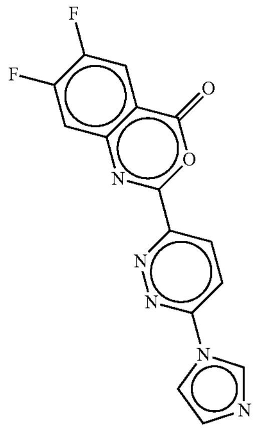 | 140 | ++++ | MS-ESI: m/z 328.45 observed $(M + H)^+$ |
| 30 | 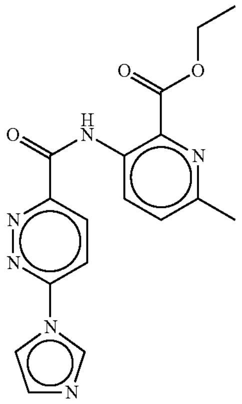 | 148.9 | ++++ | MS-ESI: m/z 353.44 observed $(M + H)^+$ |
| 31 | 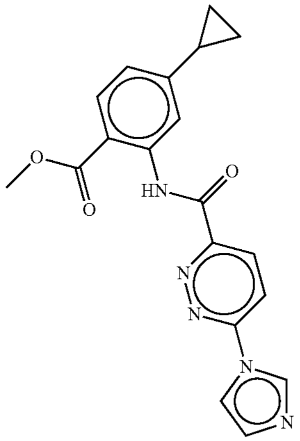 | 206.4 | ++++ | $^1H$ NMR (400 MHz, DMSO-$d_6$) δ 13.07 (s, 1H), 8.84 (t, J = 1.1 Hz, 1H), 8.62 (d, J =1.8 Hz, 1H), 8.55 (d, J = 9.1 Hz, 1H), 8.48 (d, J = 9.1 Hz, 1H), 8.27-8.21 (m, 1H), 7.97 (d, J = 8.3 Hz, 1H), 7.32-7.24 (m, 1H), 7.01 (dd, J = 8.3, 1.9 Hz, 1H), 3.93 (s, 3H), 2.11-2.01 (m, 1H), 1.18-1.07 (m, 2H), 0.85-0.77 (m, 2H). MS-ESI: m/z 364.49 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 32 | 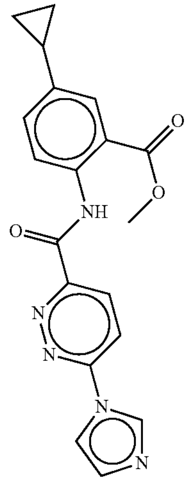 | 358.8 | ++++ | MS-ESI: m/z 364.49 observed $(M + H)^+$ |
| 33 | 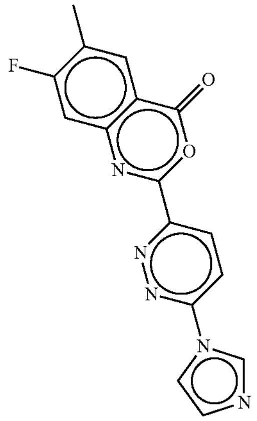 | <19.53 | ++++ | MS-ESI: m/z 324.49 observed $(M + H)^+$ |
| 34 | 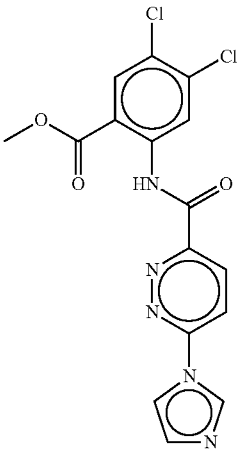 | 72.61 | ++++ | MS-ESI: m/z 392.43 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 35 | 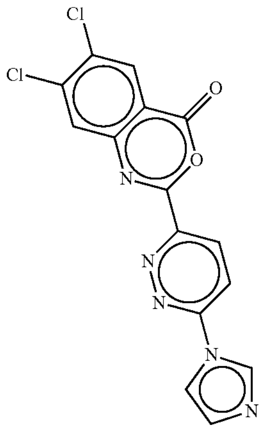 | 61.67 | ++++ | MS-ESI: m/z 360.47 observed $(M+H)^+$ |
| 36 | 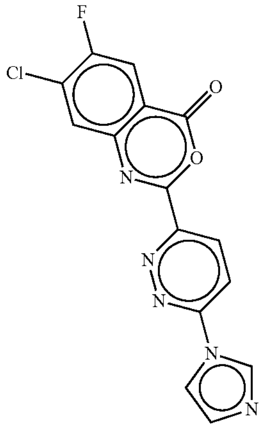 | 40.35 | ++++ | MS-ESI: m/z 344.46 observed $(M+H)^+$ |
| 37 | 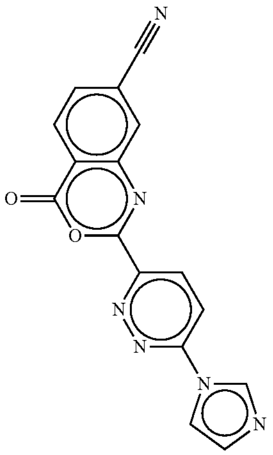 | 165.8 | ++++ | 1H NMR (400 MHz, DMSO-d6) δ 8.82 (s, 1H), 8.67 (d, J = 9.3 Hz, 1H), 8.47 (d, J = 9.2 Hz, 1H), 8.40-8.35 (m, 2H), 8.25-8.21 (m, 1H), 8.11 (dd, J = 8.2, 1.5 Hz, 1H), 7.28 (s, 1H). MS-ESI: m/z 317.46 observed $(M+H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 38 | 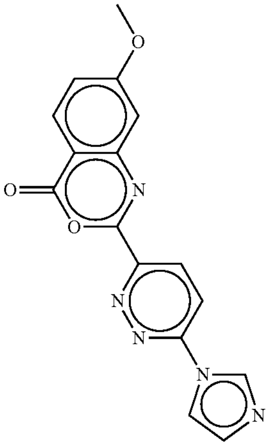 | 484.9 | ++++ | MS-ESI: m/z 322.11 observed $(M + H)^+$ |
| 39 | 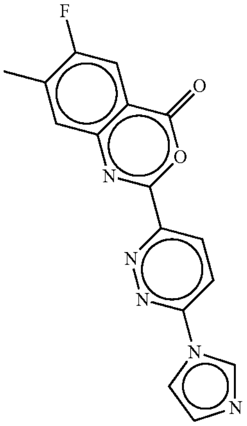 | 30.81 | ++++ | MS-ESI: m/z 324.12 observed $(M + H)^+$ |
| 40 | 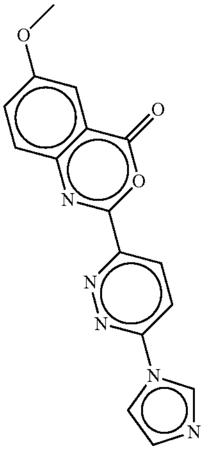 | 684.1 | ++++ | 1H NMR (400 MHz, DMSO-d6) δ 8.65 (d, J = 9.2 Hz, 1H), 8.42 (d, J = 9.3 Hz, 1H), 8.20 (t, J = 1.4 Hz, 1H), 7.80 (d, J = 8.4 Hz, 1H), 7.67-7.56 (m, 2H), 7.27 (dd, J = 1.5, 0.8 Hz, 1H), 3.95 (s, 3H). MS-ESI: m/z 322.11 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 41 | 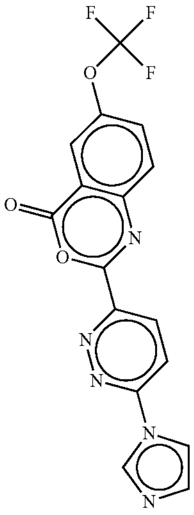 | 176.2 | ++++ | $^{1}H$ NMR (400 MHz, DMSO-$d_6$) δ 8.87-8.80 (m, 1H), 8.71 (d, J = 9.2 Hz, 1H), 8.46 (d, J = 9.3 Hz, 1H), 8.27-8.19 (m, 1H), 8.19-8.11 (m, 1H), 8.10-8.02 (m, 1H), 7.98 (d, J = 8.8 Hz, 1H), 7.34-7.24 (m, 1H). MS-ESI: m/z 376.05 observed $(M + H)^+$ |
| 42 | 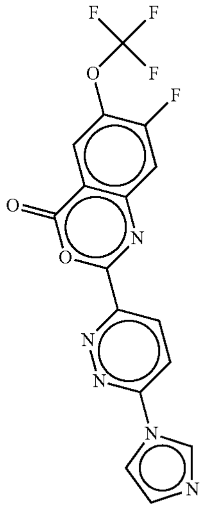 | 373.3 | ++++ | MS-ESI: m/z 394.07 observed $(M + H)^+$ |
| 43 | 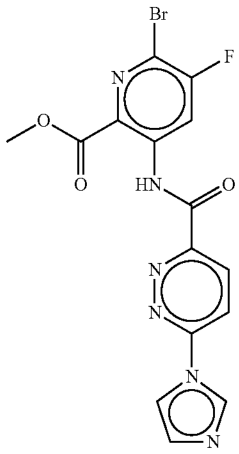 | 142.4 | ++++ | MS-ESI: m/z 423.01 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 44 | 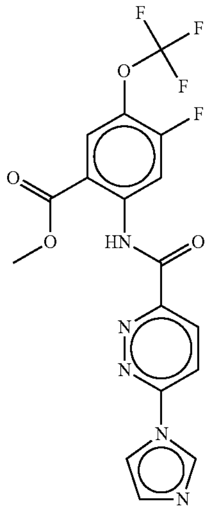 | 573.3 | ++++ | MS-ESI: m/z 426.09 observed $(M + H)^+$ |
| 45 | 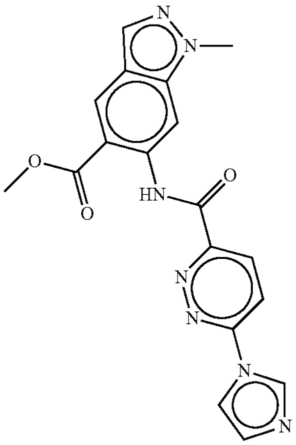 | 125.9 | ++++ | MS-ESI: m/z 378.12 observed $(M + H)^+$ |
| 46 | 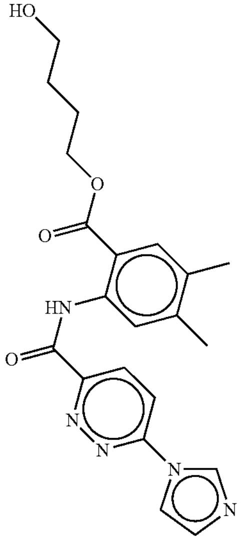 | 418.1 | ++++ | MS-ESI: m/z 410.15 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 47 | 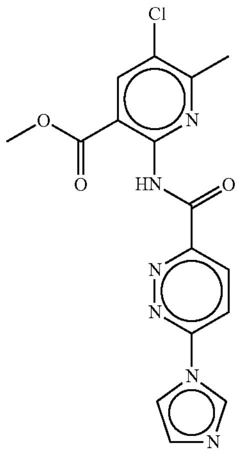 | 281.7 | ++++ | MS-ESI: m/z 373.1 observed $(M + H)^+$ |
| 48 | 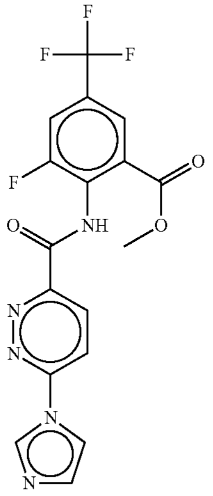 | 474.8 | ++++ | MS-ESI: m/z 410.15 observed $(M + H)^+$ |
| 49 | 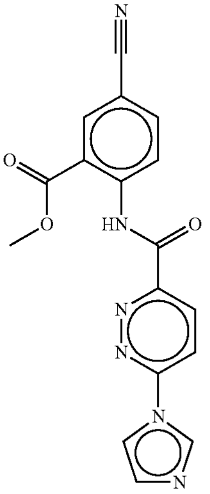 | 587.7 | ++++ | MS-ESI: m/z 349.11 observed $(M + H)^+$ |

TABLE 1-continued

Structures, bioactivities, and supporting structural data

| | Structure | ISG-LUC activation assay (EC50) [nM] | ISG-LUC activation assay (EC50) (Comment) | Analytical Data |
|---|---|---|---|---|
| 50 | 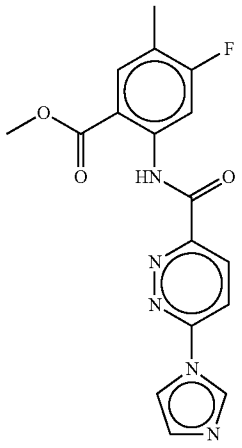 | 145 | ++++ | MS-ESI: m/z 356.15 observed $(M + H)^+$ |
| 51 | 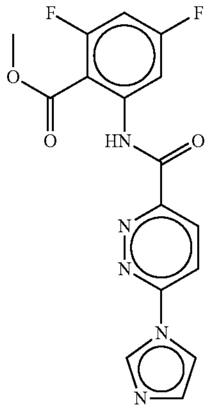 | 198.4 | ++++ | 1H NMR (400 MHz, DMSO-d6) δ 12.65 (s, 1H), 9.16 (s, 1H), 8.61 (d, J = 9.1 Hz, 1H), 8.52 (d, J = 9.2 Hz, 1H), 8.41-8.27 (m, 2H), 7.45 (s, 1H), 7.29 (ddd, J = 11.6, 9.0, 2.6 Hz, 1H), 3.94 (s, 3H). MS-ESI: m/z 360.17 observed $(M + H)^+$ |
| 52 | 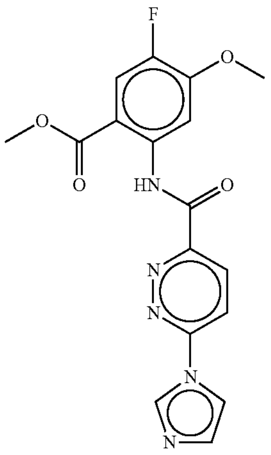 | 74.45 | ++++ | $^1$H NMR (400 MHz, DMSO-$d_6$) δ 13.16 (s, 1H), 8.83 (t, J = 1.1 Hz, 1H), 8.76 (d, J = 8.2 Hz, 1H), 8.55 (d, J = 9.0 Hz, 1H), 8.48 (d, J = 9.2 Hz, 1H), 8.23 (t, J = 1.5 Hz, 1H), 7.84 (d, J = 12.1 Hz, 1H), 7.30-7.25 (m, 1H), 3.99 (s, 3H), 3.92 (s, 3H). MS-ESI: m/z 372.1 observed $(M + H)^+$ |

TABLE 1-continued

| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 53 | 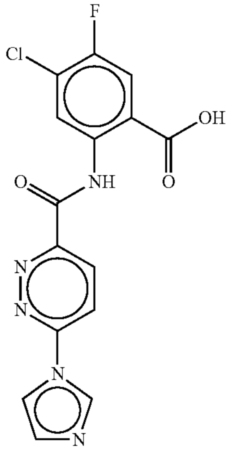 | ~624.6 | ++++ | $^1$H NMR (400 MHz, DMSO-$d_6$) δ 15.98 (s, 1H), 8.94 (d, J = 7.1 Hz, 1H), 8.80 (t, J = 1.1 Hz, 1H), 8.46 (d, J = 9.2 Hz, 1H), 8.41 (d, J = 9.2 Hz, 1H), 8.21 (t, J = 1.4 Hz, 1H), 7.88 (d, J = 10.3 Hz, 1H), 7.29-7.23 (m, 1H). MS-ESI: m/z 362.41 observed $(M + H)^+$ |
| 54 | 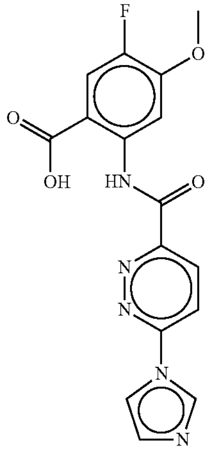 | 247.8 | ++++ | $^1$H NMR (400 MHz, DMSO-$d_6$) δ 13.34 (s, 1H), 8.82 (s, 1H), 8.77 (d, J = 8.1 Hz, 1H), 8.55 (d, J = 9.1 Hz, 1H), 8.47 (d, J = 9.1 Hz, 1H), 8.22 (t, J = 1.5 Hz, 1H), 7.82 (d, J = 12.1 Hz, 1H), 7.30-7.24 (m, 1H), 3.97 (s, 3H); (carboxylic acid proton not located) MS-ESI: m/z 358.47 observed $(M + H)^+$ |
| 55 | 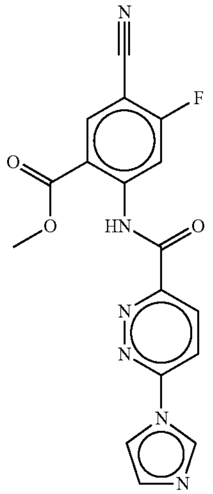 | 221.1 | ++++ | MS-ESI: m/z 367.5 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 56 | 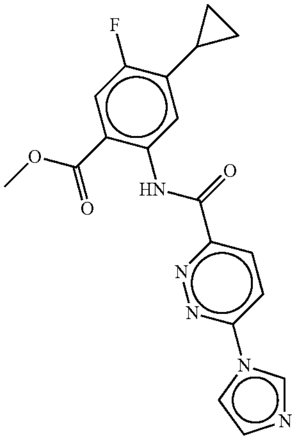 | 301.7 | ++++ | $^1$H NMR (400 MHz, DMSO-$d_6$) δ 12.90 (s, 1H), 8.83 (s, 1H), 8.55 (d, J = 9.1 Hz, 1H), 8.52-8.43 (m, 2H), 8.27-8.20 (m, 1H), 7.77 (d, J = 10.8 Hz, 1H), 7.28 (dd, J = 1.5, 0.9 Hz, 1H), 3.94 (s, 3H), 2.19 (td, J = 8.5, 4.4 Hz, 1H), 1.22-1.14 (m, 2H), 0.90-0.78 (m, 2H). MS-ESI: m/z 382.51 observed $(M + H)^+$ |
| 57 | 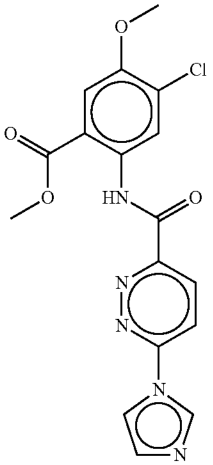 | <19.53 | ++++ | MS-ESI: m/z 388.41 observed $(M + H)^+$ |
| 58 | 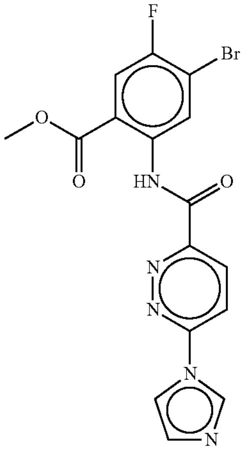 | 60.58 | ++++ | MS-ESI: m/z 422.25 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 59 | 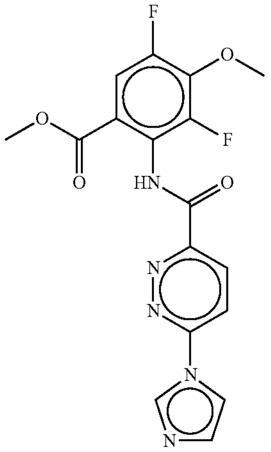 | 779.9 | ++++ | MS-ESI: m/z 390.42 observed $(M + H)^+$ |
| 60 | 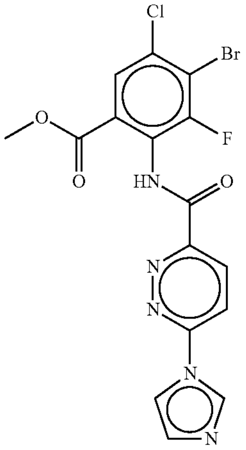 | 62.25 | ++++ | MS-ESI: m/z 456.22 observed $(M + H)^+$ |
| 61 | 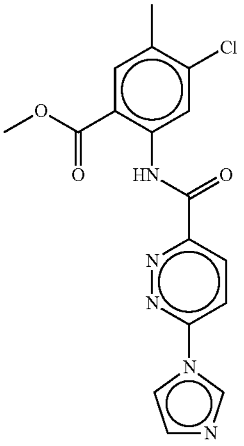 | 124 | ++++ | MS-ESI: m/z 372.42 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 62 | 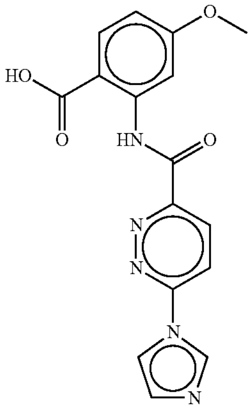 | 1457 | +++ | MS-ESI: m/z 340.14 observed $(M + H)^+$ |
| 63 | 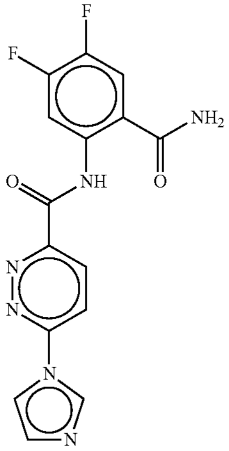 | 2638 | +++ | MS-ESI: m/z 345.47 observed $(M + H)^+$ |
| 64 | 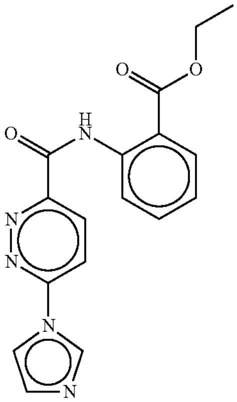 | 926.2 | +++ | MS-ESI: m/z 338.3 observed $(M + H)^+$ |

TABLE 1-continued
Structures, bioactivities, and supporting structural data
| | Structure | ISG-LUC activation assay (EC50) [nM] | ISG-LUC activation assay (EC50) (Comment) | Analytical Data |
|---|---|---|---|---|
| 65 | 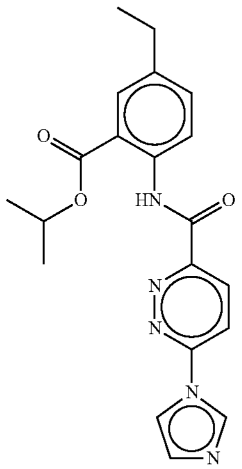 | 1156 | +++ | MS-ESI: m/z 380.31 observed $(M + H)^+$ |
| 66 | 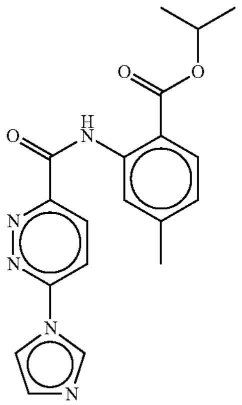 | 517.7 | +++ | MS-ESI: m/z 366.3 observed $(M + H)^+$ |
| 67 | 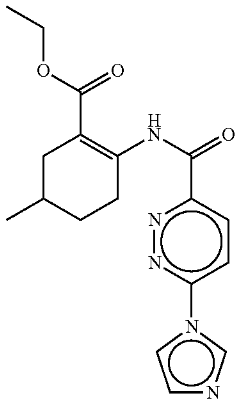 | 2953 | +++ | 1H NMR (400 MHz, Methanol-d4) δ 13.49 (s, 1H), 9.26 (s, 1H), 8.52 (d, J = 9.2 Hz, 1H), 8.38-8.27 (m, 2H), 7.52 (s, 1H), 4.27 (q, J = 7.2 Hz, 2H), 3.12-2.98 (m, 1H), 2.69-2.56 (m, 1H), 2.02- 1.83 (m, 2H), 1.78-1.64 (m, 1H), 1.40-1.25 (m, 5H), 1.06 (d, J = 6.5 Hz, 3H). MS-ESI: m/z 356.59 observed $(M + H)^+$ |

TABLE 1-continued
Structures, bioactivities, and supporting structural data
| | Structure | ISG-LUC activation assay (EC50) [nM] | ISG-LUC activation assay (EC50) (Comment) | Analytical Data |
|---|---|---|---|---|
| 68 | 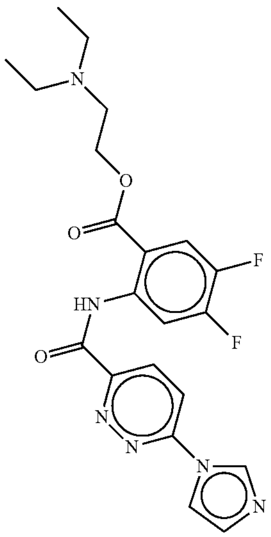 | 1808 | +++ | MS-ESI: m/z 445.43 observed $(M + H)^+$ |
| 69 | 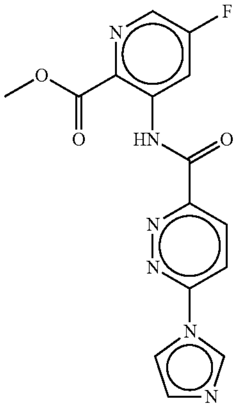 | 2786 | +++ | MS-ESI: m/z 343.52 observed $(M + H)^+$ |
| 70 | 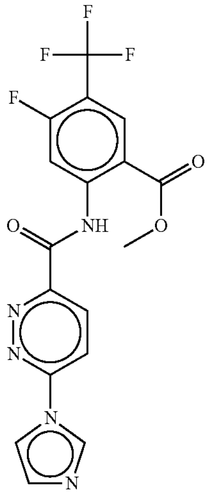 | 1719 | +++ | MS-ESI: m/z 410.09 observed $(M + H)^+$ |

TABLE 1-continued
Structures, bioactivities, and supporting structural data
| | Structure | ISG-LUC activation assay (EC50) [nM] | ISG-LUC activation assay (EC50) (Comment) | Analytical Data |
| --- | --- | --- | --- | --- |
| 71 | 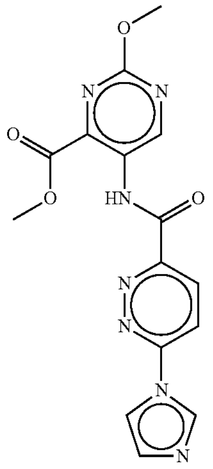 | 1658 | +++ | MS-ESI: m/z 356.15 observed $(M + H)^+$ |
| 72 | 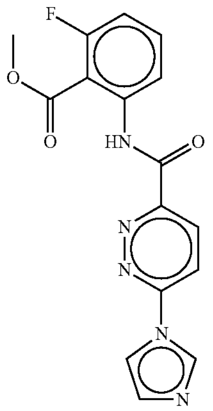 | 1670 | +++ | 1H NMR (400 MHz, DMSO-d6) δ 12.23 (s, 1H), 9.13 (s, 1H), 8.59 (d, J = 9.1 Hz, 1H), 8.51 (d, J = 9.2 Hz, 1H), 8.40-8.26 (m, 2H), 7.73 (td, J = 8.4, 6.2 Hz, 1H), 7.44 (s, 1H), 7.26-7.17 (m, 1H), 3.92 (s, 3H). MS-ESI: m/z 342.15 observed $(M + H)^+$ |
| 73 | 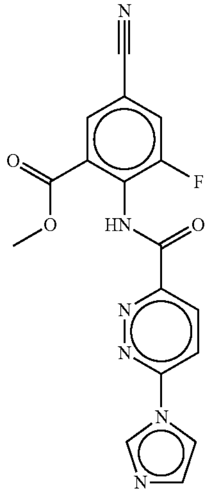 | 2370 | +++ | MS-ESI: m/z 367.1 observed $(M + H)^+$ |

TABLE 1-continued

Structures, bioactivities, and supporting structural data

| | Structure | ISG-LUC activation assay (EC50) [nM] | ISG-LUC activation assay (EC50) (Comment) | Analytical Data |
|---|---|---|---|---|
| 74 | 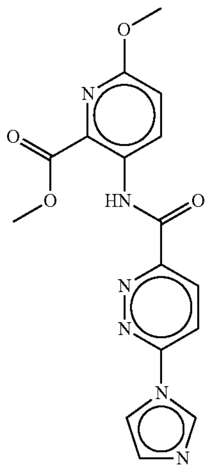 | 1355 | +++ | 1H NMR (400 MHz, DMSO-d6) δ 12.67 (s, 1H), 9.04 (d, J = 9.2 Hz, 1H), 8.88-8.79 (m, 1H), 8.55 (d, J = 9.1 Hz, 1H), 8.47 (d, J = 9.2 Hz, 1H), 8.27-8.19 (m, 1H), 7.30-7.23 (m, 2H), 5.76 (s, 1H), 3.95 (s, 3H), 3.91 (s, 3H). MS-ESI: m/z 355.14 observed $(M + H)^+$ |
| 75 | 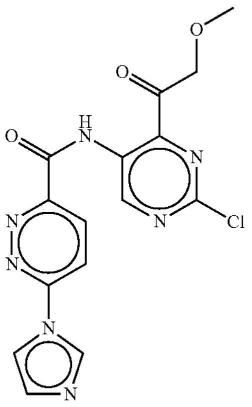 | 1261 | +++ | $^1H$ NMR (400 MHz, DMSO-$d_6$) δ 12.47 (s, 1H), 9.94 (s, 1H), 8.91-8.80 (m, 1H), 8.60 (d, J = 9.1 Hz, 1H), 8.50 (d, J = 9.1 Hz, 1H), 8.30-8.18 (m, 1H), 7.33-7.19 (m, 1H), 4.46 (q, J = 7.1 Hz, 2H), 1.37 (t, J = 7.1 Hz, 3H). MS-ESI: m/z 374.1 observed $(M + H)^+$ |
| 76 | 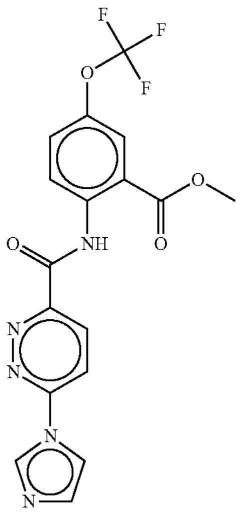 | 572.9 | +++ | MS-ESI: m/z 408.38 observed $(M + H)^+$ |

TABLE 1-continued
| Structures, bioactivities, and supporting structural data | | | | |
| --- | --- | --- | --- | --- |
| | Structure | ISG-LUC activation assay (EC50) [nM] | ISG-LUC activation assay (EC50) (Comment) | Analytical Data |
| 77 | 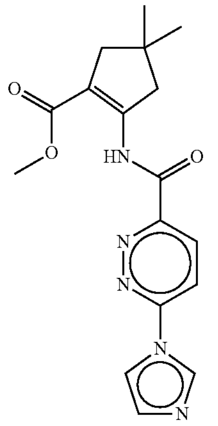 | >50000 | ++ | MS-ESI: m/z 342.21 observed $(M + H)^+$ |
| 78 | 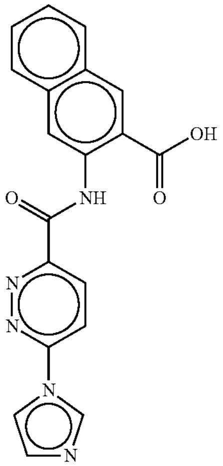 | 4440 | ++ | MS-ESI: m/z 360.33 observed $(M + H)^+$ |
| 79 | 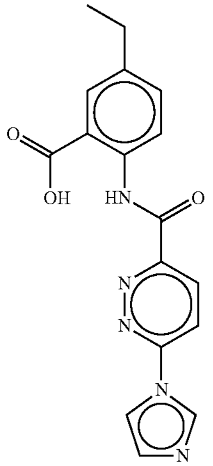 | >20000 | ++ | MS-ESI: m/z 338.5 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 80 | 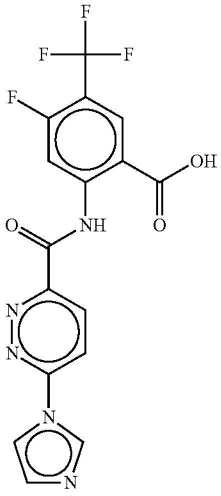 | 3974 | ++ | MS-ESI: m/z 396.08 observed $(M + H)^+$ |
| 81 | 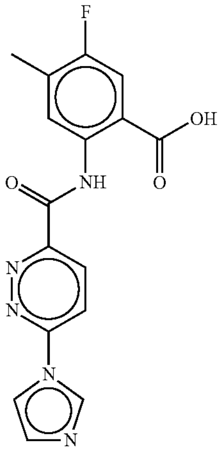 | 2736 | ++ | MS-ESI: m/z 342.15 observed $(M + H)^+$ |
| 82 | 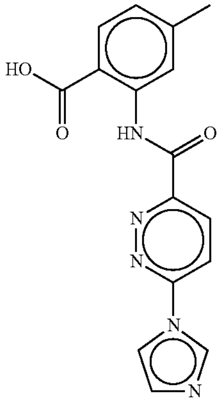 | 6390 | ++ | MS-ESI: m/z 324.12 observed $(M + H)^+$ |

TABLE 1-continued
| | Structures, bioactivities, and supporting structural data | | | |
|---|---|---|---|---|
| | Structure | ISG-LUC activation assay (EC50) [nM] | ISG-LUC activation assay (EC50) (Comment) | Analytical Data |
| 83 | 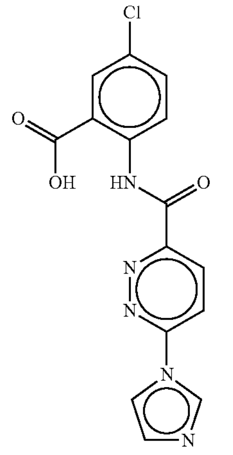 | >20000 | ++ | MS-ESI: m/z 344.02 observed $(M + H)^+$ |
| 84 | 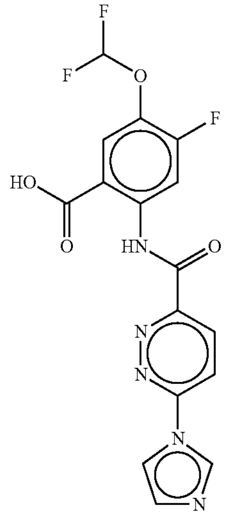 | 8593 | ++ | MS-ESI: m/z 394.07 observed $(M + H)^+$ |
| 85 | 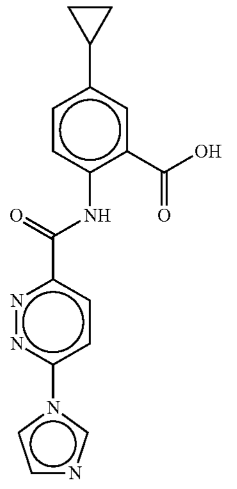 | ~16556 | ++ | $^1H$ NMR (400 MHz, DMSO-$d_6$) δ 15.90 (s, 1H), 8.79 (app t, J = 1.1 Hz, 1H), 8.60 (d, J = 8.5 Hz, 1H), 8.45 (d, J = 9.1 Hz, 1H), 8.39 (d, J = 9.1 Hz, 1H), 8.21 (appt, J = 1.5 Hz, 1H), 7.74 (d, J = 2.4 Hz, 1H), 7.26 (s, 1H), 7.06 (dd, J = 8.4, 2.4 Hz, 1H), 1.96- 1.79 (m, 1H), 0.97-0.88 (m, 2H), 0.66-0.59 (m, 2H). MS-ESI: m/z 350.5 observed $(M + H)^+$ |

TABLE 1-continued
| | Structures, bioactivities, and supporting structural data | | | |
|---|---|---|---|---|
| | Structure | ISG-LUC activation assay (EC50) [nM] | ISG-LUC activation assay (EC50) (Comment) | Analytical Data |
| 86 | 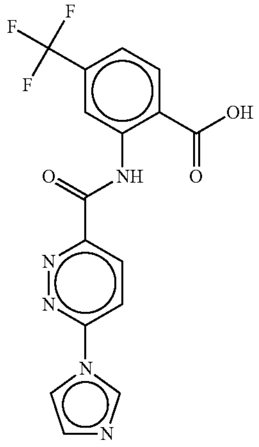 | 10341 | ++ | MS-ESI: m/z 378.12 observed $(M + H)^+$ |
| 87 | 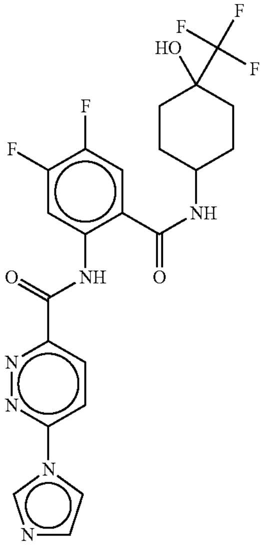 | >20000 | ++ | MS-ESI: m/z 511.23 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 88 | 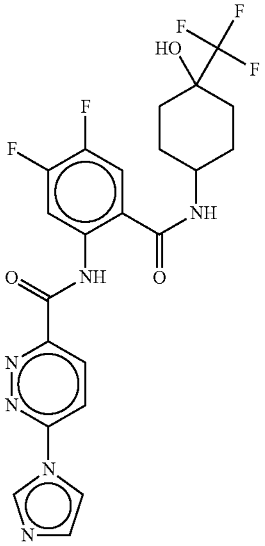 | 5244 | ++ | MS-ESI: m/z 511.23 observed $(M + H)^+$ |
| 89 | 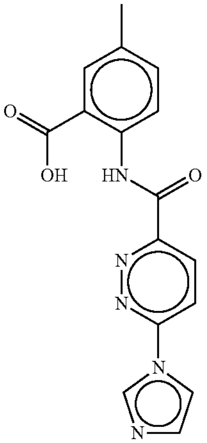 | >20000 | ++ | MS-ESI: m/z 324.12 observed $(M + H)^+$ |
| 90 | 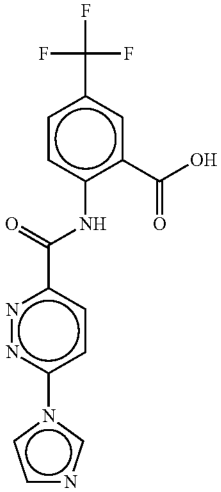 | >20000 | ++ | MS-ESI: m/z 378.06 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 91 | 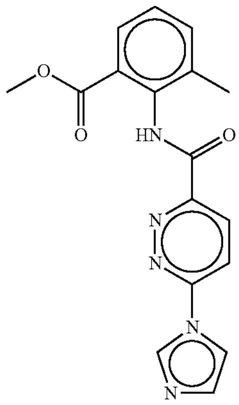 | ~5073 | ++ | MS-ESI: m/z 338.3 observed $(M + H)^+$ |
| 92 | 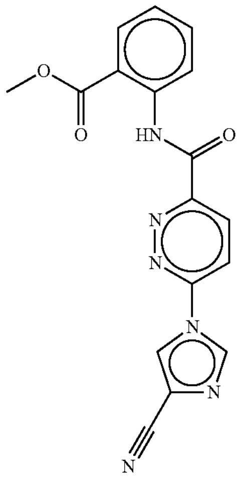 | ~5256 | ++ | MS-ESI: m/z 349.1 observed $(M + H)^+$ |
| 93 | 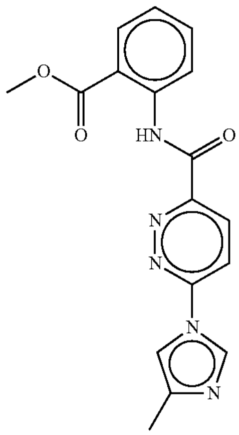 | >20000 | ++ | MS-ESI: m/z 338.3 observed $(M + H)^+$ |

TABLE 1-continued

| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 95 | 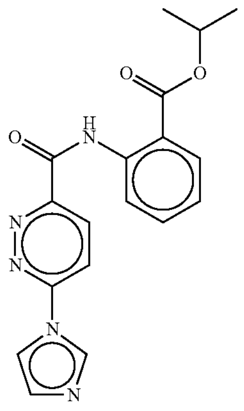 | 1701 | ++ | $^1$H NMR (400 MHz, DMSO-$d_6$) δ 13.04 (s, 1H), 9.16 (s, 1H), 8.84 (d, J = 8.4 Hz, 1H), 8.61 (d, J = 9.1 Hz, 1H), 8.51 (d, J = 9.1 Hz, 1H), 8.35 (d, J = 1.5 Hz, 1H), 8.10 (dd, J = 8.0, 1.6 Hz, 1H), 7.78-7.71 (m, 1H), 7.46 (s, 1H), 7.37-7.26 (m, 1H), 5.27 (p, J = 6.2 Hz, 1H), 1.39 (d, J = 6.2 Hz, 7H).6 MS-ESI: m/z 352.3 observed $(M + H)^+$ |
| 96 | 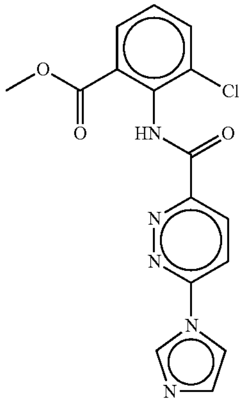 | 21070 | ++ | 1H NMR (400 MHz, DMSO-d6) δ 11.07 (s, 1H), 9.49 (s, 1H), 8.60 (d, J = 9.1 Hz, 1H), 8.54 (d, J = 9.1 Hz, 1H), 8.44 (s, 1H), 7.86 (dd, J = 8.0, 2.6 Hz, 2H), 7.66 (s, 1H), 7.59-7.47 (m, 1H), 3.73 (s, 3H). MS-ESI: m/z 358.2 observed $(M + H)^+$ |
| 97 | 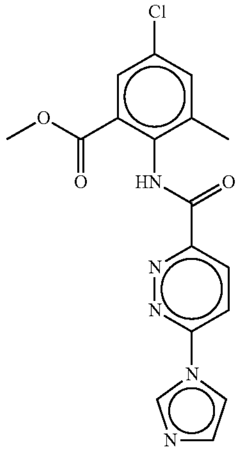 | ~2485 | ++ | 1H NMR (400 MHz, DMSO-d6) δ 10.97 (s, 1H), 9.31 (s, 1H), 8.59-8.46 (m, 2H), 8.38 (s, 1H), 7.71 (s, 2H), 7.56 (s, 1H), 3.72 (s, 5H), 2.32 (s, 4H). MS-ESI: m/z 372.27 observed $(M + H)^+$ |

TABLE 1-continued

| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 98 | 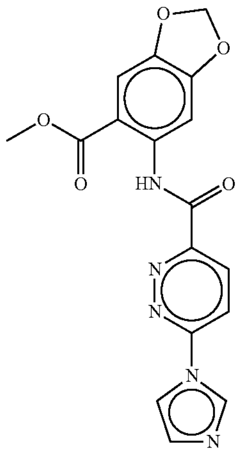 | 2678 | ++ | 1H NMR (400 MHz, DMSO-d6) δ 13.26 (s, 1H), 9.33 (s, 1H), 8.62 (d, J = 9.2 Hz, 1H), 8.53 (d, J = 9.1 Hz, 1H), 8.46 (s, 1H), 8.42 (s, 1H), 7.57-7.50 (m, 2H), 6.20 (s, 2H), 3.91 (s, 3H). MS-ESI: m/z 368.25 observed $(M + H)^+$ |
| 99 | 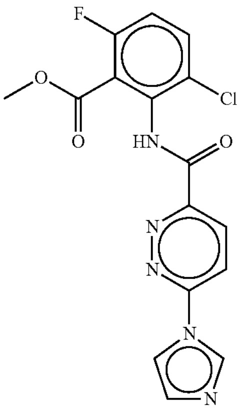 | 11919 | ++ | $^1H$ NMR (400 MHz, DMSO-$d_6$) δ 11.19 (s, 1H), 9.44 (s, 1H), 8.63-8.52 (m, 2H), 8.43 (s, 1H), 7.87 (dd, J = 9.2, 5.4 Hz, 1H), 7.63 (s, 1H), 7.47 (t, J = 9.1 Hz, 1H), 3.76 (s, 4H). MS-ESI: m/z 376.22 observed $(M + H)^+$ |
| 100 | 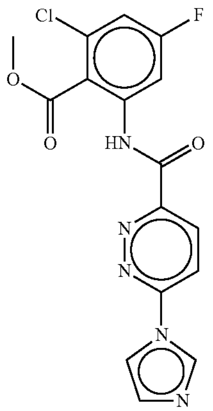 | 10199 | ++ | 1H NMR (400 MHz, DMSO-d6) δ 11.45 (s, 1H), 9.06 (s, 1H), 8.56 (d, J = 9.2 Hz, 1H), 8.49 (d, J = 9.1 Hz, 1H), 8.30 (s, 1H), 8.01-7.97 (m, 1H), 7.52 (dd, J = 8.4, 2.5 Hz, 1H), 7.41 (s, 1H), 3.90 (s, 3H). MS-ESI: m/z 376.22 observed $(M + H)^+$ |

TABLE 1-continued

Structures, bioactivities, and supporting structural data

| | Structure | ISG-LUC activation assay (EC50) [nM] | ISG-LUC activation assay (EC50) (Comment) | Analytical Data |
|---|---|---|---|---|
| 101 | 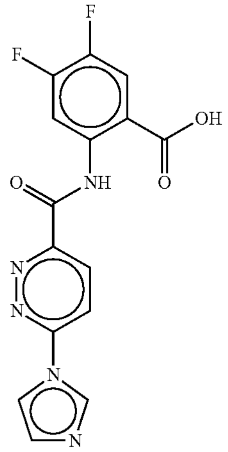 | 731.3 | ++++ | $^1$H NMR (400 MHz, DMSO-$d_6$) δ 16.11 (s, 1H), 8.79 (s, 1H), 8.74 (dd, J = 13.8, 7.7 Hz, 1H), 8.47 (d, J = 9.1 Hz, 1H), 8.40 (d, J = 9.2 Hz, 1H), 8.21 (t, J = 1.5 Hz, 1H), 7.92 (dd, J = 11.9, 9.8 Hz, 1H), 7.26 (d, J = 1.4 Hz, 1H). MS-ESI: m/z 346.1 observed $(M + H)^+$ |
| 102 | 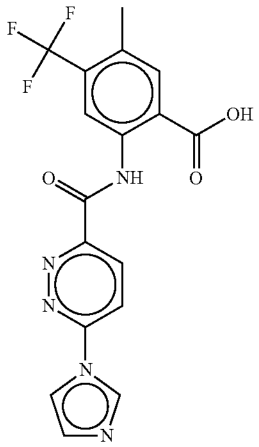 | 12059 | ++ | $^1$H NMR (400 MHz, DMSO-$d_6$) δ 15.91 (s, 1H), 9.13 (s, 1H), 8.80 (s, 1H), 8.46 (d, J = 9.2 Hz, 1H), 8.41 (d, J = 9.2 Hz, 1H), 8.25-8.16 (m, 1H), 8.03 (s, 1H), 7.26 (s, 1H), 2.44-2.37 (m, 3H). MS-ESI: m/z 392.44 observed $(M + H)^+$ |
| 103 | 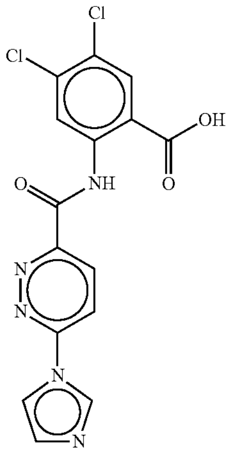 | 451.3 | ++++ | MS-ESI: m/z 378.06 observed $(M + H)^+$ |

TABLE 1-continued

| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 104 | 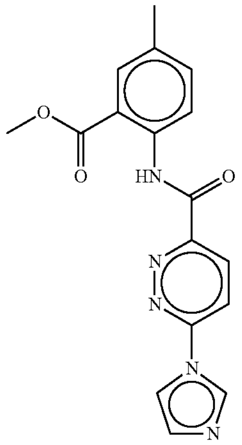 | 425.8 | ++++ | MS-ESI: m/z 338.3 observed $(M + H)^+$ |
| 105 | 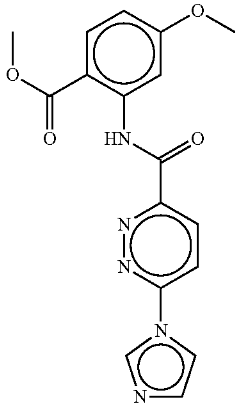 | 192.5 | ++++ | $^1H$ NMR (400 MHz, DMSO-$d_6$) δ 13.26 (s, 1H), 9.39 (s, 1H), 8.63 (d, J = 9.1 Hz, 1H), 8.58-8.48 (m, 2H), 8.43 (d, J = 1.6 Hz, 1H), 8.07 (d, J = 8.9 Hz, 1H), 7.58 (s, 1H), 6.88 (dd, J = 8.9, 2.6 Hz, 1H), 3.92 (s, 3H), 3.89 (s, 3H). MS-ESI: m/z 354.24 observed $(M + H)^+$ |
| 106 | 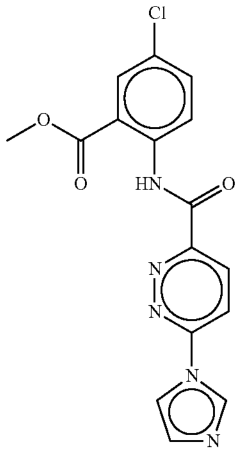 | 345.9 | ++++ | $^1H$ NMR (400 MHz, DMSO-$d_6$) δ 13.00 (s, 1H), 9.51 (s, 1H), 8.84 (d, J = 9.0 Hz, 1H), 8.65 (d, J = 9.2 Hz, 1H), 8.56 (d, J = 9.2 Hz, 1H), 8.47 (d, J = 1.7 Hz, 1H), 8.04 (d, J = 2.7 Hz, 1H), 7.83 (dd, J = 9.0, 2.7 Hz, 1H), 7.63 (d, J = 1.7 Hz, 1H), 3.96 (s, 4H). MS-ESI: m/z 358.2 observed $(M + H)^+$ |

TABLE 1-continued
| | Structures, bioactivities, and supporting structural data | | | |
|---|---|---|---|---|
| | Structure | ISG-LUC activation assay (EC50) [nM] | ISG-LUC activation assay (EC50) (Comment) | Analytical Data |
| 107 | 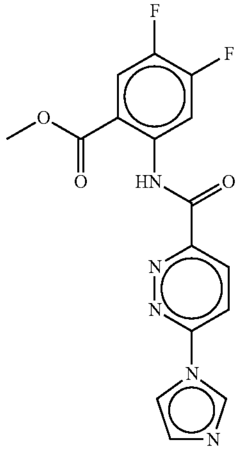 | 414.8 | ++++ | $^1H$ NMR (400 MHz, DMSO-$d_6$) δ 13.08 (s, 1H), 9.26 (s, 1H), 8.83 (dd, J = 13.5, 7.5 Hz, 1H), 8.61 (d, J = 9.2 Hz, 1H), 8.52 (d, J = 9.2 Hz, 1H), 8.39-8.36 (m, 1H), 8.09 (dd, J = 11.2, 9.0 Hz, 1H), 7.50 (s, 1H), 3.95 (s, 3H). MS-ESI: m/z 360.21 observed $(M + H)^+$ |
| 108 | 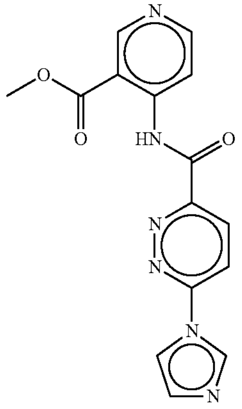 | 3346 | ++ | MS-ESI: m/z 325.36 observed $(M + H)^+$ |
| 109 | 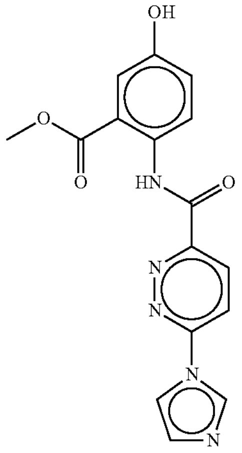 | 8945 | ++ | MS-ESI: m/z 340.44 observed $(M + H)^+$ |

TABLE 1-continued

Structures, bioactivities, and supporting structural data

| | Structure | ISG-LUC activation assay (EC50) [nM] | ISG-LUC activation assay (EC50) (Comment) | Analytical Data |
|---|---|---|---|---|
| 110 | 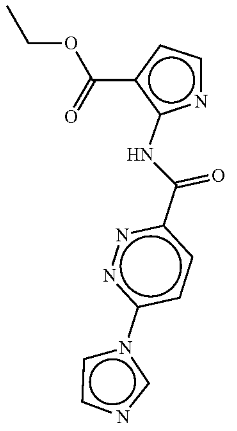 | 16896 | ++ | MS-ESI: m/z 327.44 observed $(M + H)^+$ |
| 111 | 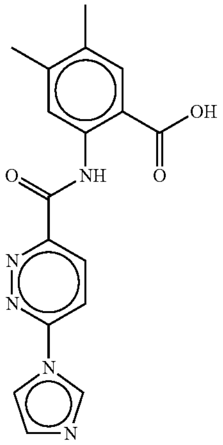 | 7248 | ++ | 1H NMR (400 MHz, DMSO-d6) δ 8.79 (d, J = 1.1 Hz, 1H), 8.57 (s, 1H), 8.45 (d, J = 9.1 Hz, 1H), 8.40 (d, J = 9.2 Hz, 1H), 8.20 (t, J = 1.4 Hz, 1H), 7.80 (s, 1H), 7.26 (t, J = 1.3 Hz, 1H), 2.26 (s, 3H), 2.21 (s, 3H). MS-ESI: m/z 338.19 observed $(M + H)^+$ |
| 112 | 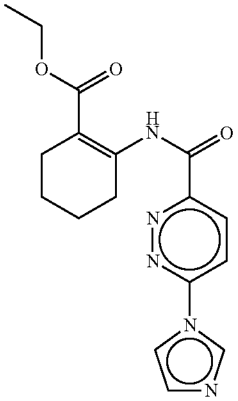 | 1504 | ++ | 1H NMR (400 MHz, Methanol-d4) δ 13.48 (s, 1H), 9.23 (s, 1H), 8.52 (d, J = 9.2 Hz, 1H), 8.37-8.24 (m, 2H), 7.51 (s, 1H), 4.27 (q, J = 7.1 Hz, 2H), 3.21-3.11 (m, 2H), 2.51-2.39 (m, 2H), 1.82-1.64 (m, 4H), 1.34 (t, J = 7.1 Hz, 4H). MS-ESI: m/z 342.45 observed $(M + H)^+$ |

TABLE 1-continued
Structures, bioactivities, and supporting structural data
| | Structure | ISG-LUC activation assay (EC50) [nM] | ISG-LUC activation assay (EC50) (Comment) | Analytical Data |
|---|---|---|---|---|
| 113 | 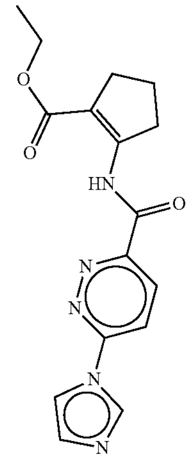 | 18734 | ++ | MS-ESI: m/z 328.51 observed $(M + H)^+$ |
| 114 | 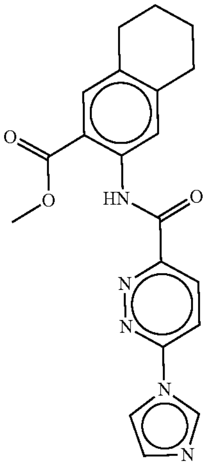 | 4345 | ++ | 1H NMR (400 MHz, Methanol-d4) δ 13.11 (s, 1H), 9.75 (s, 1H), 8.66 (d, J = 9.2 Hz, 1H), 8.61 (s, 1H), 8.49 (s, 1H), 8.44 (d, J = 9.1 Hz, 1H), 7.85 (s, 1H), 7.76 (s, 1H), 3.97 (s, 3H), 2.88 (s, 2H), 2.79 (s, 2H), 1.92-1.81 (m, 4H). MS-ESI: m/z 378.56 observed $(M + H)^+$ |
| 115 | 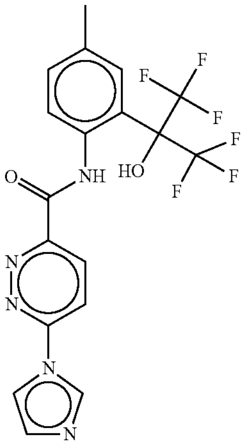 | 7363 | ++ | MS-ESI: m/z 446.37 observed $(M + H)^+$ |

TABLE 1-continued

| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 116 | 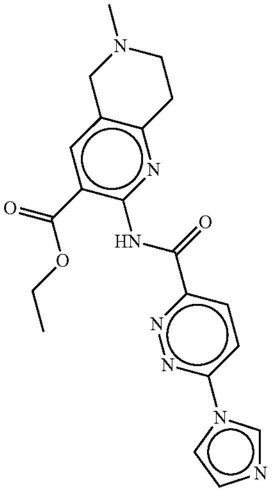 | 3464 | ++ | 1H NMR (400 MHz, Methanol-d4) δ 9.27 (s, 1H), 8.66 (d, J = 9.1 Hz, 1H), 8.44-8.37 (m, 2H), 8.32 (s, 1H), 7.53 (s, 1H), 4.69-4.37 (m, 4H), 3.92-3.64 (m, 2H), 3.41 (t, J = 6.4 Hz, 2H), 3.13 (s, 3H), 1.46 (t, J = 7.1 Hz, 3H). MS-ESI: m/z 408.45 observed $(M + H)^+$ |
| 117 | 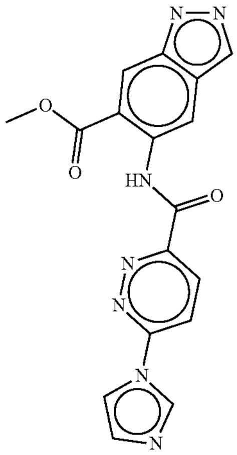 | ~2574 | ++ | MS-ESI: m/z 364.43 observed $(M + H)^+$ |
| 118 | 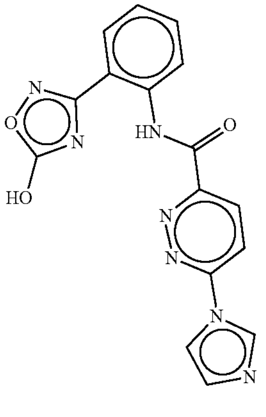 | 3967 | ++ | 1H NMR (400 MHz, Methanol-d4) δ 13.51 (s, 1H), 10.06 (s, 1H), 8.95 (d, J = 7.9 Hz, 1H), 8.73 (d, J = 9.1 Hz, 1H), 8.63-8.58 (m, 1H), 8.50 (d, J = 9.1 Hz, 1H), 8.20 (dd, J = 7.9, 1.6 Hz, 1H), 7.92 (dd, J = 2.2, 1.3 Hz, 1H), 7.73-7.64 (m, 1H), 7.31-7.23 (m, 1H). MS-ESI: m/z 350.49 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 119 | 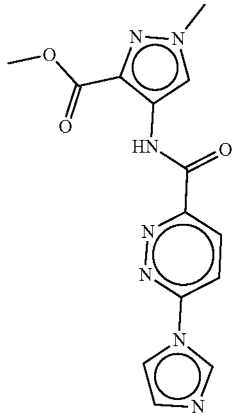 | 5892 | ++ | MS-ESI: m/z 328.51 observed $(M + H)^+$ |
| 120 | 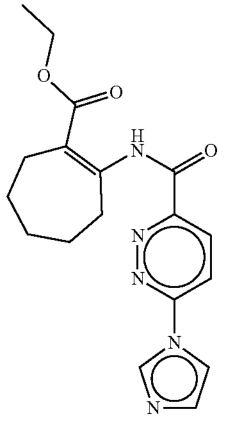 | >50000 | ++ | MS-ESI: m/z 356.59 observed $(M + H)^+$ |
| 121 | 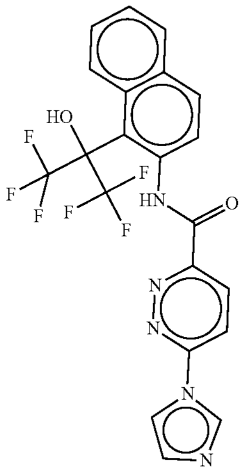 | 1832 | ++ | MS-ESI: m/z 482.49 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 122 | 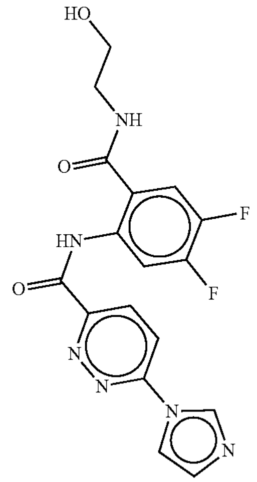 | 7955 | ++ | MS-ESI: m/z 389.49 observed $(M + H)^+$ |
| 123 | 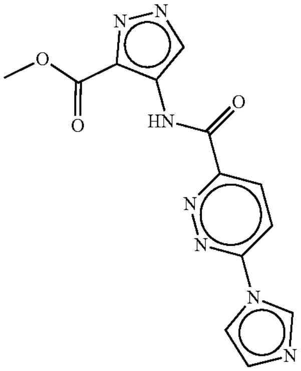 | 2993 | ++ | MS-ESI: m/z 314.44 observed $(M + H)^+$ |
| 124 | 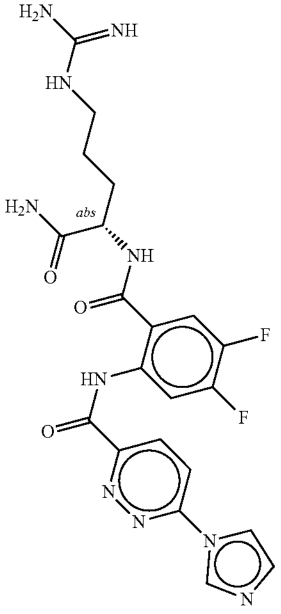 | 8078 | ++ | MS-ESI: m/z 501.58 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 125 | 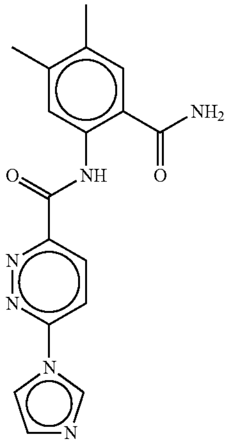 | 9617 | ++ | MS-ESI: m/z 337.49 observed $(M + H)^+$ |
| 126 | 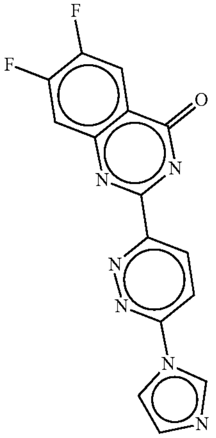 | 1120 | ++ | $^1$H NMR (400 MHz, DMSO-$d_6$) δ 12.96 (s, 1H), 9.00 (s, 1H), 8.73 (dd, J = 9.3, 1.1 Hz, 1H), 8.50 (d, J = 9.3 Hz, 1H), 8.26 (d, J = 1.9 Hz, 1H), 8.15 (dd, J = 10.3, 8.6 Hz, 1H), 7.93 (dd, J = 11.2, 7.2 Hz, 1H), 7.39 (s, 1H). MS-ESI: m/z 327.44 observed $(M + H)^+$ |
| 127 | 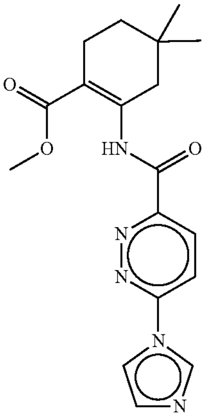 | 7299 | ++ | MS-ESI: m/z 356.59 observed $(M + H)^+$ |

TABLE 1-continued
Structures, bioactivities, and supporting structural data
| | Structure | ISG-LUC activation assay (EC50) [nM] | ISG-LUC activation assay (EC50) (Comment) | Analytical Data |
|---|---|---|---|---|
| 128 | 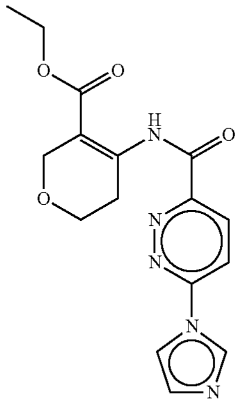 | 4349 | ++ | MS-ESI: m/z 344.53 observed $(M + H)^+$ |
| 129 | 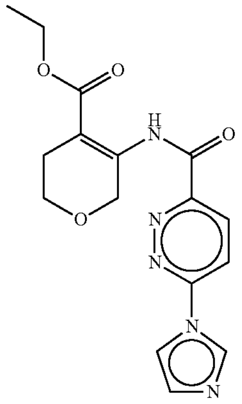 | 10683 | ++ | MS-ESI: m/z 344.53 observed $(M + H)^+$ |
| 130 | 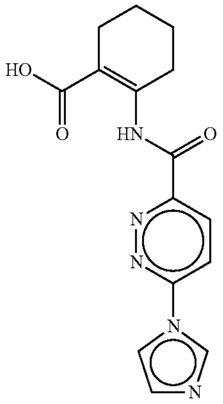 | 14770 | ++ | MS-ESI: m/z 314.51 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 131 | 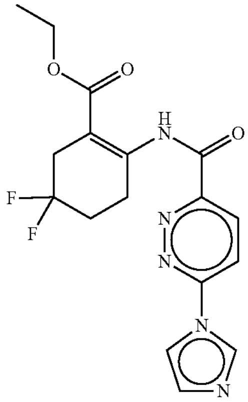 | 3479 | ++ | MS-ESI: m/z 378.5 observed $(M + H)^+$ |
| 132 | 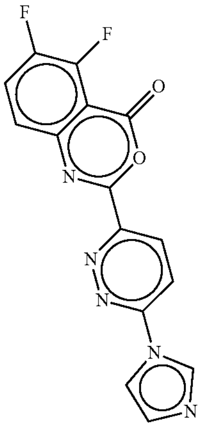 | 4284 | ++ | MS-ESI: m/z 328.45 observed $(M + H)^+$ |
| 133 | 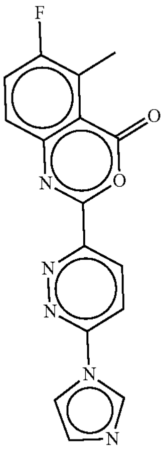 | 4173 | ++ | MS-ESI: m/z 324.49 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 134 | 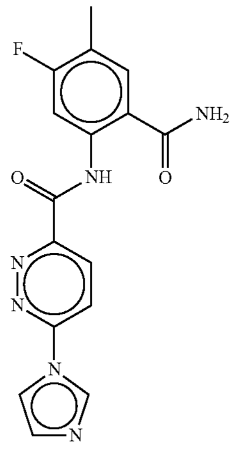 | >50000 | ++ | MS-ESI: m/z 341.51 observed $(M + H)^+$ |
| 135 | 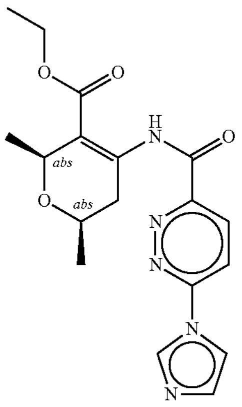 | 12331 | ++ | MS-ESI: m/z 372.53 observed $(M + H)^+$ |
| 136 | 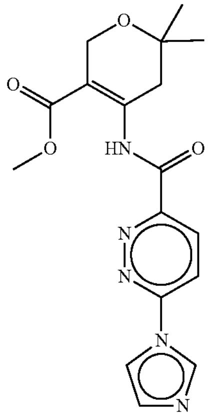 | 8844 | ++ | MS-ESI: m/z 358.6 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 137 | 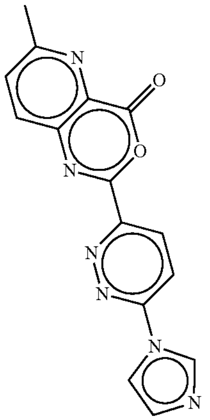 | 9328 | ++ | MS-ESI: m/z 307.54 observed $(M + H)^+$ |
| 138 | 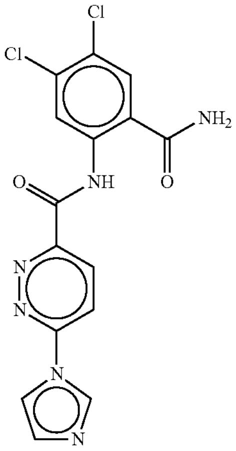 | >50000 | ++ | MS-ESI: m/z 377.49 observed $(M + H)^+$ |
| 139 | 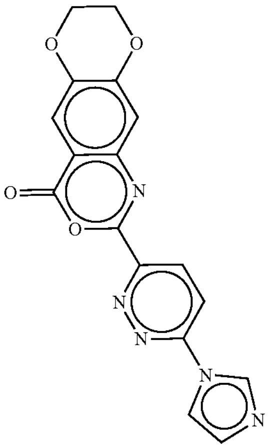 | 2518 | ++ | MS-ESI: m/z 350.56 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 140 | 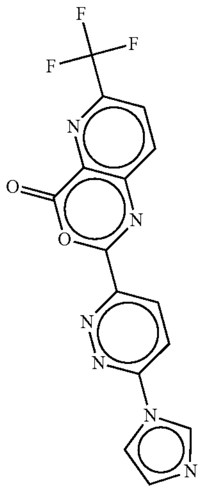 | ~25059 | ++ | MS-ESI: m/z 361.5 observed $(M+H)^+$ |
| 141 | 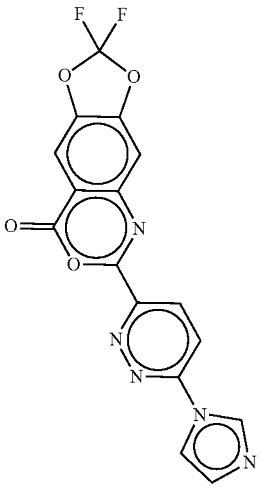 | >50000 | ++ | MS-ESI: m/z 372.1 observed $(M+H)^+$ |
| 142 | 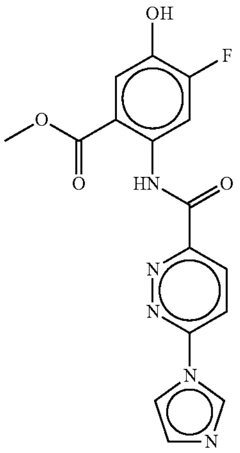 | >50000 | ++ | MS-ESI: m/z 358.16 observed $(M+H)^+$ |

TABLE 1-continued
| | Structures, bioactivities, and supporting structural data | | | |
|---|---|---|---|---|
| | Structure | ISG-LUC activation assay (EC50) [nM] | ISG-LUC activation assay (EC50) (Comment) | Analytical Data |
| 143 | 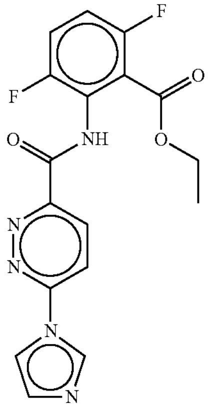 | 9714 | ++ | MS-ESI: m/z 374.1 observed $(M + H)^+$ |
| 144 | 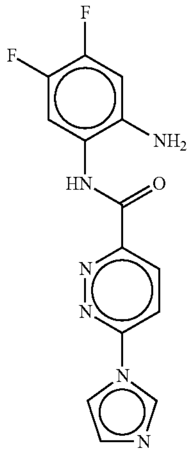 | >50000 | ++ | MS-ESI: m/z 317.16 observed $(M + H)^+$ |
| 145 | 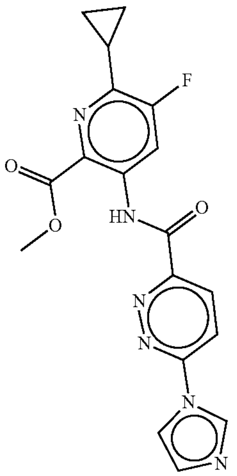 | 1583 | ++ | MS-ESI: m/z 383.15 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 146 | 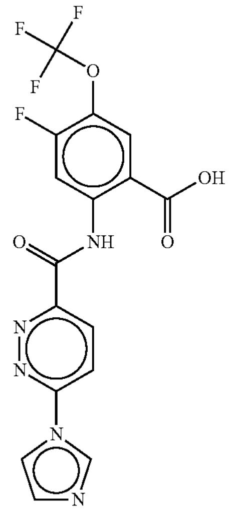 | 2178 | ++ | MS-ESI: m/z 412.09 observed $(M + H)^+$ |
| 147 | 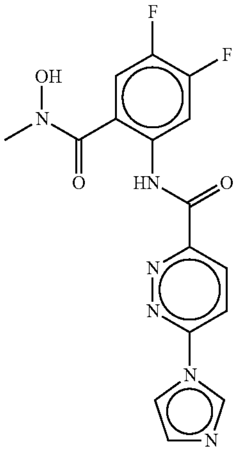 | 5245 | ++ | MS-ESI: m/z 375.11 observed $(M + H)^+$ |
| 148 | 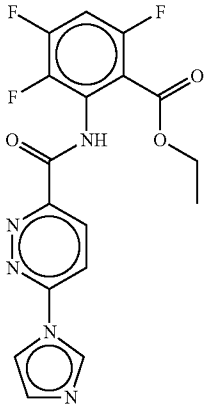 | 3677 | ++ | MS-ESI: m/z 392.19 observed $(M + H)^+$ |

TABLE 1-continued
| | Structures, bioactivities, and supporting structural data | | | |
|---|---|---|---|---|
| | Structure | ISG-LUC activation assay (EC50) [nM] | ISG-LUC activation assay (EC50) (Comment) | Analytical Data |
| 149 | 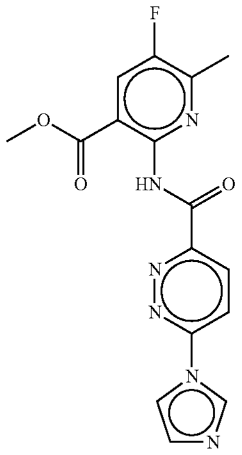 | 30053 | ++ | MS-ESI: m/z 357.15 observed $(M + H)^+$ |
| 150 | 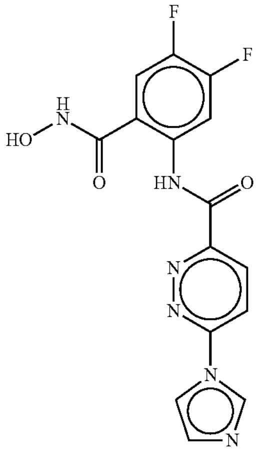 | 12167 | ++ | MS-ESI: m/z 361.11 observed $(M + H)^+$ |
| 151 | 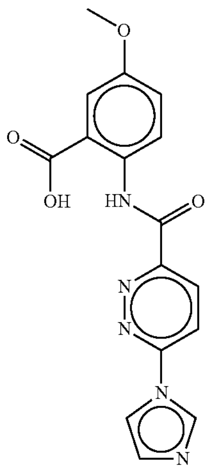 | 7761 | ++ | $^1H$ NMR (400 MHz, DMSO-$d_6$) δ 15.68 (s, 1H), 8.78 (t, J = 1.1 Hz, 1H), 8.66 (d, J = 8.9 Hz, 1H), 8.44 (d, J = 9.1 Hz, 1H), 8.39 (d, J = 9.2 Hz, 1H), 8.20 (app t, J = 1.5 Hz, 1H), 7.61 (d, J = 3.2 Hz, 1H), 7.26 (dd, J = 1.5, 0.9 Hz, 1H), 6.92 (dd, J = 9.0, 3.2 Hz, 1H), 3.75 (s, 3H). MS-ESI: m/z 340.4 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 152 | 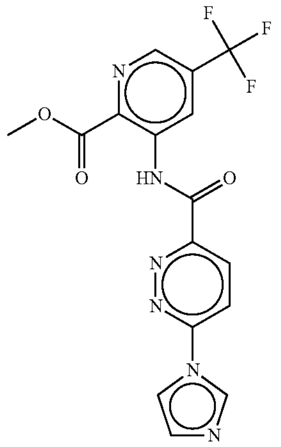 | ~1266 | ++ | 1H NMR (400 MHz, Methanol-d4) δ 9.71 (s, 1H), 9.28 (s, 1H), 8.74 (s, 1H), 8.67 (d, J = 9.1 Hz, 1H), 8.41 (d, J = 9.1 Hz, 1H), 8.33 (s, 1H), 7.53 (s, 1H), 4.11 (s, 3H). MS-ESI: m/z 393.13 observed $(M + H)^+$ |
| 153 | 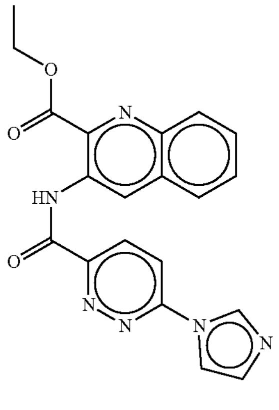 | 42.99 | +++ | MS-ESI: m/z 389.18 observed $(M + H)^+$ |
| 154 | 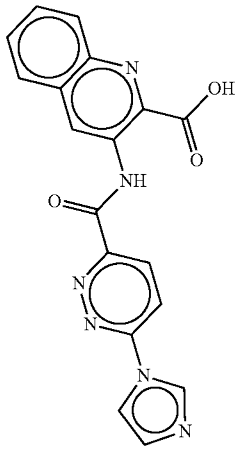 | ~10383 | ++ | MS-ESI: m/z 361 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 155 | 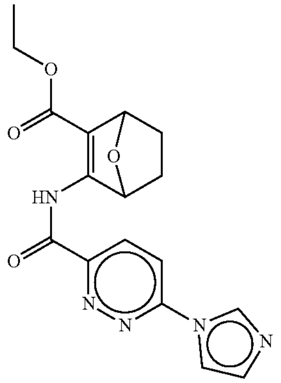 | >50000 | ++ | MS-ESI: m/z 356.15 observed $(M + H)^+$ |
| 156 | 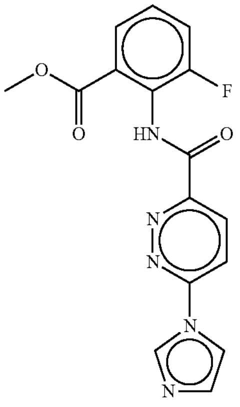 | >50000 | ++ | MS-ESI: m/z 342.15 observed $(M + H)^+$ |
| 157 | 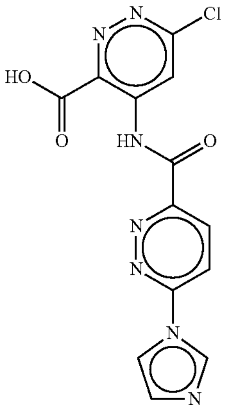 | >50000 | ++ | MS-ESI: m/z 346.17 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 158 | 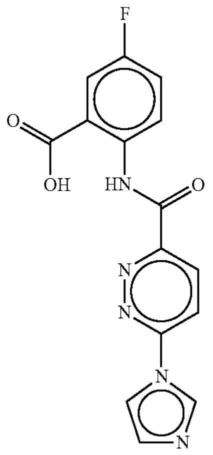 | >20000 | ++ | MS-ESI: m/z 328.08 observed $(M + H)^+$ |
| 159 | 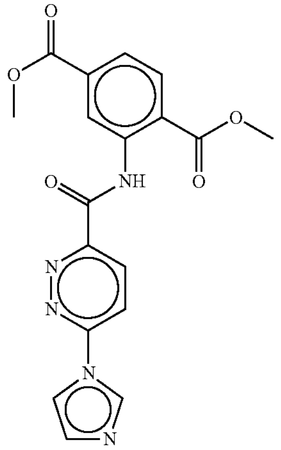 | >20000 | ++ | MS-ESI: m/z 382.14 observed $(M + H)^+$ |
| 160 | 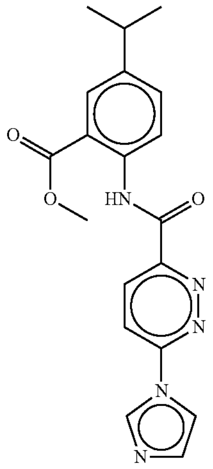 | 3842 | ++ | 1H NMR (400 MHz, DMSO-d6) δ 12.96 (s, 1H), 8.85-8.82 (m, 1H), 8.77 (d, J = 8.6 Hz, 1H), 8.55 (d, J = 9.1 Hz, 1H), 8.47 (d, J = 9.2 Hz, 1H), 8.28-8.18 (m, 1H), 7.94 (d, J = 2.3 Hz, 1H), 7.66 (dd, J = 8.7, 2.3 Hz, 1H), 7.27 (t, J = 1.2 Hz, 1H), 3.95 (s, 3H), 2.97 (dt, J = 13.3, 6.6 Hz, 1H), 1.24 (d, J = 6.9 Hz, 6H). MS-ESI: m/z 366.2 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 161 | 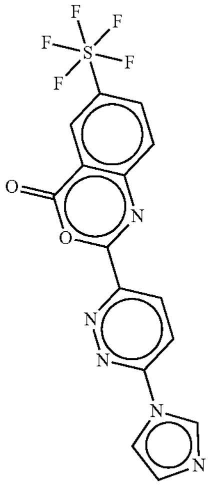 | >20000 | ++ | MS-ESI: m/z 418.05 observed $(M + H)^+$ |
| 162 | 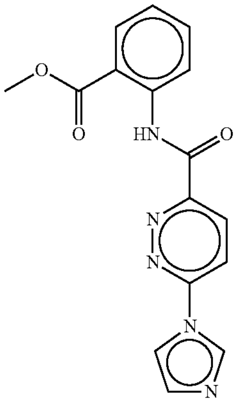 | 956.4 | +++ | $^1H$ NMR (400 MHz, DMSO-$d_6$) δ 13.08 (s, 1H), 9.39 (s, 1H), 8.86 (d, J = 8.4 Hz, 1H), 8.65 (d, J = 9.1 Hz, 1H), 8.55 (d, J = 9.1 Hz, 1H), 8.44 (s, 1H), 8.11 (d, J = 7.9 Hz, 1H), 7.77 (app t, J = 7.9 Hz, 1H), 7.58 (s, 1H), 7.32 (appt, J = 7.6 Hz, 1H), 3.96 (s, 3H). MS-ESI: m/z 324.27 observed $(M + H)^+$ |
| 163 | 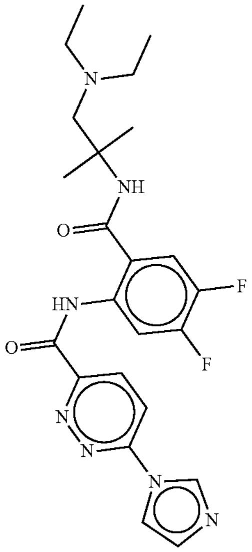 | 16559 | ++ | MS-ESI: m/z 472.18 observed $(M + H)^+$ |

TABLE 1-continued
Structures, bioactivities, and supporting structural data
| | Structure | ISG-LUC activation assay (EC50) [nM] | ISG-LUC activation assay (EC50) (Comment) | Analytical Data |
|---|---|---|---|---|
| 164 | 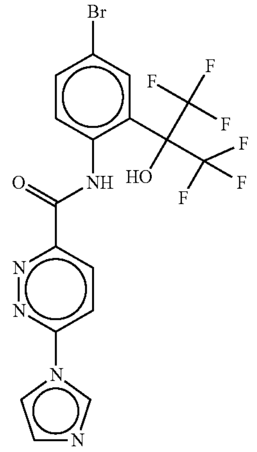 | >20000 | ++ | 1H NMR (400 MHz, DMSO-d6) δ 12.27 (s, 1H), 10.77 (s, 1H), 9.01 (s, 1H), 8.71 (d, J = 9.0 Hz, 1H), 8.61 (d, J = 9.1 Hz, 1H), 8.51 (d, J = 9.1 Hz, 1H), 8.27 (d, J = 1.5 Hz, 1H), 7.89 (dd, J = 9.0, 2.2 Hz, 1H), 7.61 (d, J = 2.2 Hz, 1H), 7.39 (s, 1H). MS-ESI: m/z 511.97 observed $(M + H)^+$ |
| 165 | 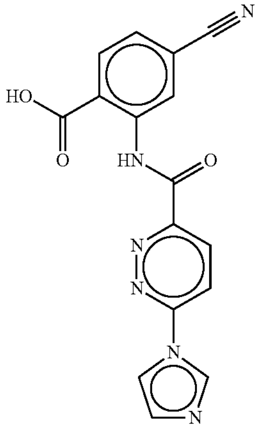 | 4086 | ++ | MS-ESI: m/z 335.11 observed $(M + H)^+$ |
| 166 | 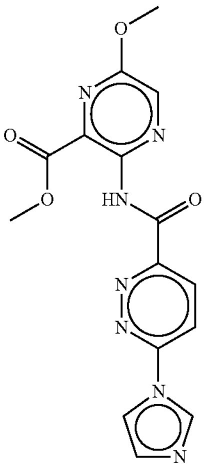 | 12093 | ++ | MS-ESI: m/z 356.08 observed $(M + H)^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 167 | 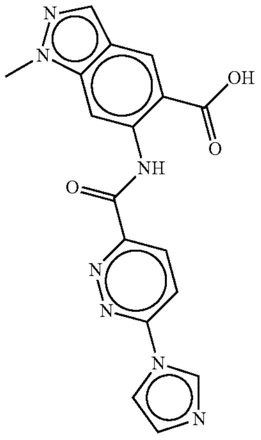 | 14939 | ++ | MS-ESI: m/z 364.12 observed $(M + H)^+$ |
| 168 | 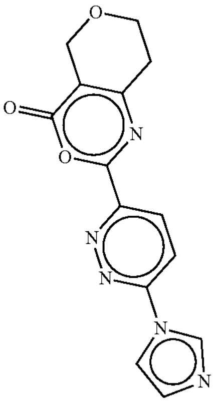 | 11265 | ++ | MS-ESI: m/z 298.2 observed $(M + H)^+$ |
| 169 | 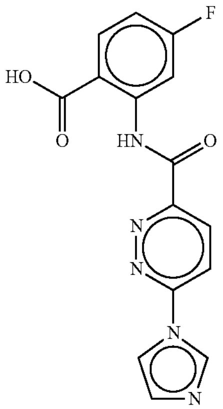 | 12637 | ++ | MS-ESI: m/z 328.47 observed $(M + H)^+$ |

TABLE 1-continued

Structures, bioactivities, and supporting structural data

| | Structure | ISG-LUC activation assay (EC50) [nM] | ISG-LUC activation assay (EC50) (Comment) | Analytical Data |
|---|---|---|---|---|
| 170 | 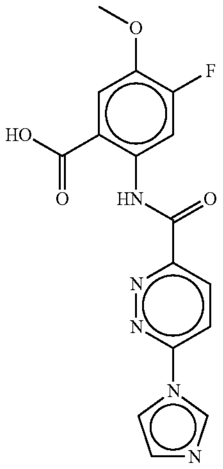 | 10950 | ++ | $^1$H NMR (400 MHz, DMSO-$d_6$) δ 13.18 (s, 1H), 9.05 (s, 1H), 8.74 (d, J = 14.1 Hz, 1H), 8.58 (d, J = 9.1 Hz, 1H), 8.49 (d, J = 9.2 Hz, 1H), 8.30 (s, 1H), 7.77 (d, J = 9.6 Hz, 1H), 7.40 (s, 1H), 3.91 (s, 3H); (carboxylic acid proton not located) MS-ESI: m/z 358.48 observed (M + H)$^+$ |
| 171 | 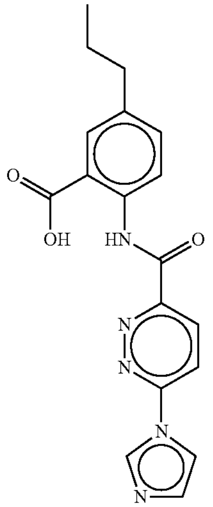 | >20000 | ++ | $^1$H NMR (400 MHz, DMSO-$d_6$) δ 15.92 (s, 1H), 8.79 (app t, J = 1.1 Hz, 1H), 8.62 (d, J = 8.3 Hz, 1H), 8.45 (d, J = 9.2 Hz, 1H), 8.40 (d, J = 9.2 Hz, 1H), 8.21 (appt, J = 1.4 Hz, 1H), 7.86 (d, J = 2.3 Hz, 1H), 7.26 (dd, J = 1.5, 0.9 Hz, 1H), 7.15 (dd, J = 8.4, 2.3 Hz, 1H), 2.57-2.52 (m, 2H), 1.60 (h, J = 7.2 Hz, 2H), 0.91 (t, J = 7.3 Hz, 3H) MS-ESI: m/z 352.5 observed (M + H)$^+$ |
| 172 | 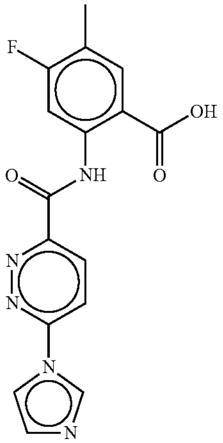 | 1010 | ++ | $^1$H NMR (400 MHz, DMSO-$d_6$) δ 16.22 (s, 1H), 8.80 (app t, J = 1.1 Hz, 1H), 8.53-8.43 (m, 2H), 8.40 (d, J = 9.1 Hz, 1H), 8.21 (app t, J = 1.4 Hz, 1H), 7.94 (d, J = 9.8 Hz, 1H), 7.26 (s, 1H), 2.21 (s, 3H). MS-ESI: m/z 342.11 (M + H)$^+$ |

TABLE 1-continued
| Structures, bioactivities, and supporting structural data | | | | |
|---|---|---|---|---|
| | Structure | ISG-LUC activation assay (EC50) [nM] | ISG-LUC activation assay (EC50) (Comment) | Analytical Data |
| 173 | 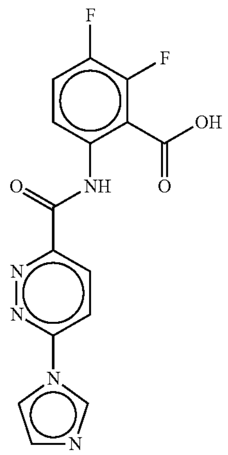 | >20000 | ++ | MS-ESI: m/z 346.45 observed $(M + H)^+$ |
| 174 | 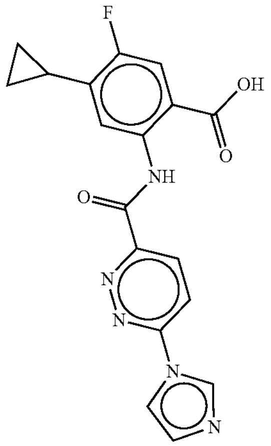 | 10042 | ++ | 1H NMR (400 MHz, DMSO-d6) δ 15.84 (s, 1H), 8.83-8.76 (m, 1H), 8.50-8.37 (m, 3H), 8.24-8.18 (m, 1H), 7.66 (d, J = 11.4 Hz, 1H), 7.26 (dd, J = 1.6, 0.9 Hz, 1H), 2.08 (td, J = 8.4, 4.3 Hz, 1H), 1.10-0.97 (m, 2H), 0.80-0.68 (m, 2H). MS-ESI: m/z 368.51 observed $(M + H)^+$ |
| 175 | 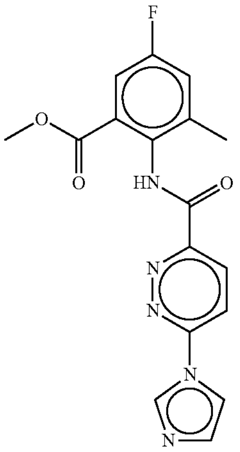 | ~2811 | ++ | MS-ESI: m/z 356.46 observed $(M + H)^+$ |

TABLE 1-continued

| | Structures, bioactivities, and supporting structural data | | | |
|---|---|---|---|---|
| | Structure | ISG-LUC activation assay (EC50) [nM] | ISG-LUC activation assay (EC50) (Comment) | Analytical Data |
| 176 | 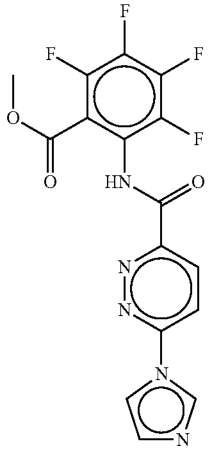 | ~2484 | ++ | MS-ESI: m/z 396.36 observed $(M + H)^+$ |
| 177 | 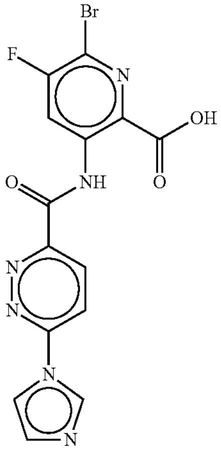 | >20000 | + | MS-ESI: m/z 409.01 mCLF203 observed $(M + H)^+$ |

Activity score based on potency and efficacy data

| Score | Interpretation |
|---|---|
| ++ | Active but less potent & efficacious than reference compound; EC50 > 1000 nM |
| +++ | Comparable activity to reference compound; EC50 < 3000 nM |
| ++++ | More potent and/or efficacious than reference compound; EC50 < 900 nM |

RELATED DOCUMENTS

[1] Corrales L, Glickman L H, McWhirter S M, Kanne D B, Sivick K E, Katibah G E, Woo S R, Lemmens E, Banda T, Leong J J, Metchette K, Dubensky T W Jr, Gajewski T F. (2015) Direct Activation of STING in the Tumor Microenvironment Leads to Potent and Systemic Tumor Regression and Immunity. *Cell Rep.* 11: 1018-30.

[2] Deng, L. et al. (2014) STING-Dependent Cytosolic DNA Sensing Promotes Radiation-Induced Type I Interferon-Dependent Antitumor Immunity in Immunogenic Tumors, *Immunity.* 41: 843.

[3] Corrales L, Matson V, Flood B, Spranger S, Gajewski T F. (2017) Innate immune signaling and regulation in cancer immunotherapy. *Cell Res.* 27: 96-108.

[4] Corrales L, McWhirter S M, Dubensky T W Jr, Gajewski T F. (2016) The host STING pathway at the interface of cancer and immunity. *J Clin Invest.* 126: 2404-11.

With respect to combination therapies comprising administration of a compound of the invention and an immune-checkpoint targeting drug, or as combination therapies for the potentiation of ionizing radiation-based and existing chemotherapies therapeutic approaches, such as DNA-damage-based chemotherapies, we believe that the STING agonists of the invention can complement and potentiate the effects of these known therapeutic approaches. This is based on recent papers indicating the critical role of STING-dependent micronuclei-mediated tumor clearance using these approaches, see for example:

[5] Mackenzie, K. F., et all, (2017), cGAS surveillance of micronuclei links genome instability to innate immunity, *Nature,* 548, 461.

[6] Wang, W. et al., (2016), Effector T Cells Abrogate Stroma-Mediated Chemoresistance in Ovarian Cancer, *Cell,* 165, 1092-1105.

[7] Charlotte E. Ariyan, et al., Jan. 16, 2018; DOI: 10.1158/2326-6066, Robust antitumor responses result from local chemotherapy and CTLA-4 blockade, cancerimmunolres.aacrjournals.org on Jan. 31, 2018.

[8] Chung Kil Song, et al., www.moleculartherapy.org vol. 15 no. 8 Aug. 2007, Chemotherapy Enhances CD8+ T Cell-mediated Antitumor Immunity Induced by Vaccination With Vaccinia Virus.

Compounds of the invention can be used in therapeutic combinations with administration of an effective dose of an immune-checkpoint targeting drug. For example, the immune-checkpoint targeting drug can be an anti-PD-L1 antibody, anti-PD-1 antibody, anti-CTLA-4 antibody, or an anti-4-1BB antibody. See, for example:

[9] Ager, C R, et al., (2017) Cancer Immunol Res; 5(8), 676.

[10] Fu, J. et al. (2015) *Sci Transl Med.* 2015 Apr. 15; 7(283): 283ra52. doi:10.1126/scitranslmed.aaa4306.

[11] Wang, H., et al. (2017) PNAS|Feb. 14, 2017|vol. 114|no. 7|1637-1642.

EXAMPLES

Tissue Culture

Wild-type (cat. no. thpl-isg) and STING KO (cat. no. thpd-kostg) THP-1-Lucia ISG cells were purchased from Invivogen and maintained in growth media consisting of RPMI 1640, 2 mM L-glutamine, 25 mM HEPES, 10% heat-inactivated fetal bovine serum (FBS), 1,000 units/ml penicillin, 1,000 μg/ml streptomycin, 0.25 μg/ml Amphotericin B, and 100 μg/ml zeocin unless otherwise stated.

Type 1 Interferon Stimuli

Poly(dA:dT) and 2'3'-cGAMP were purchased from invivogen and resuspended according to manufacturer's instructions.

ISRE-Luciferase Assay

THP-1 Lucia ISG cells were resuspended in low-serum growth media (2% FBS) at a density of $5\times10^5$ cells/ml and treated with test article or vehicle (DMSO). 50 μL of cells were seeded into each well of a 384-well white greiner plates and incubated for 24 hours. To evaluate expression of the luciferase reporter, 30 μl of Quanti-luc (Invivogen) detection reagent was added to each well and luminescence was read using an Envision plate reader (Perkin Elmer) set with an integration time of 0.1 seconds.

Viability Assay

Cells were resuspended in low-serum growth media at a density of $5\times10^5$ cells/ml and treated with test article or vehicle (DMSO). 50 μL of cells were seeded into each well of a 384-well white greiner plates and incubated for 24 hours. To evaluate expression of the luciferase reporter, 30 μl of CellTiter-Glo (Promega) detection reagent was added to each well and luminescence was detected \using an Envision Plate Reader set with an integration time of 0.1 seconds.

Western Blot

Cells were solubilized in 1× protein lysis buffer (25 mM HEPES, pH 7.4, 300 mM NaCl, 1.5 mM $MgCl_2$, 1 mM EGTA, 1% P-40, 1% sodium deoxycholate, 2.5 mM sodium pyrophosphate, 1 mM glycerophosphate) with freshly added protease and phosphatase inhibitors (Cell Signaling). Western blotting was performed using Bolt™ 4-12% Bis-Tris gels and Bolt™ mini transfer system following the manufacturer's instructions (ThermoFisher Scientific). STING and γ-tubulin antibodies were purchased from Cell Signaling diluted in 5% BSA, 1×TBS-T buffer (Table 3). Anti-rabbit HRP antibody was diluted in 5% non-fat dried milk, 1×TBS-T buffer and luminescence signal was imaged using a ChemiDoc Imager (BioRad).

Semi-Quantitative Real-Time PCR (qPCR)

THP-1 cells were resuspended in low-serum growth media at a density of $5\times10^5$ cells/ml and treated with test article or vehicle (DMSO). 2.5 mL of cells were seeded into each well of a 6-well plate and incubated for 24 hours. RNA was isolated using an RNeasy Plus Mini Kit (Qiagen) and 1 μg of purified RNA was reverse-transcribed into cDNA (VILO, cat. no. 11755050, ThermoFisher Scientific). Gene expression was assessed using Taqman primers and probes listed in Table 4 with the Taqman Universal Mix II (cat. no. 4440038, ThermoFisher) following manufacturer's instructions. Gene expression was normalized using the double delta Ct method and was reported as fold change in expression.

STING Thermal Shift Assay (TSA)

The c-terminal domains (CTD) of human and mouse STING were expressed and purified as detailed previously (Ouyang et al., 2012). Test article or vehicle controls were added to diluted STING protein (0.22 mg/ml) in 1× Protein Thermal Shift Buffer provided in the Protein Thermal Shift Dye Kit (cat #4461146, ThermoFisher Scientific). Thermal Shift dye was added and mixed prior to performing a melt curve following parameters outlined for the Dye kit. Melt temperatures (Tm) were calculated using the Derivative method using Protein Thermal Shift Software v1.3 (cat #4466038, ThermoFisher Scientific).

TABLE 2

Cell Signaling Antibodies

| Protein target | Cat. No. | Dilution |
|---|---|---|
| STING | 13647 | 1:1000 |
| γ-tubulin | 5886 | 1:3000 |
| Rabbit IgG | 7074 | 1:3000 |

TABLE 3

ThermoFisher Scientific Taqman Primers/Probe

| Gene Symbol | Species | Cat. No. | Dye |
|---|---|---|---|
| IFNB1 | human | Hs01077958_s1 | FAM |
| CXCL10 | human | Hs00171042_m1 | FAM |
| IFIT3 | human | Hs01922752_s1 | FAM |
| B2M | human | Hs00187842_m1 | VIC |

Ouyang, S., Song, X., Wang, Y., Ru, H., Shaw, N., Jiang, Y., Niu, F., Zhu, Y., Qiu, W., Parvatiyar, K., et al. (2012). Structural analysis of the STING adaptor protein reveals a hydrophobic dimer interface and mode of cyclic di-GMP binding. Immunity 36, 1073-1086.

Compounds useful for carrying out a method of the invention can be prepared according to the following procedures in conjunction with ordinary knowledge and skill in organic synthesis, substituting appropriate reagents as apparent to the practitioner.

Experimental Procedures

Abbreviations

The following abbreviations are used: tetrahydrofuran (THF), dichloromethane (DCM), N,N-dimethylformamide (DMF), dimethylacetamide (DMA), dimethylsulfoxide (DMSO), trifluoroacetic acid (TFA), triethylamine (TEA), diisopropylethylamine (DIPEA), (1-Cyano-2-ethoxy-2-oxo-ethylidenaminooxy)dimethylamino-morpholino-carbenium hexafluorophosphate (COMU), 1-[bis(dimethylamino)methylene]-1H-1,2,3-triazolo[4,5-b]pyridinium 3-oxid hexafluorophosphate, N-[(dimethylamino)-1H-1,2,3-triazolo-[4,5-b]pyridin-1-ylmethylene]-N-methylmethanaminium hexafluorophosphate N-oxide (HATU).

General Examples for the Preparation of Compounds of the Invention

The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). Details of reagent and reaction options are also available by structure and reaction searches using commercial computer search engines such as Scifinder (www.cas.org) or Reaxys (www.reaxys.com).

Part I: Preparation of Intermediates

Scheme 1: Synthesis of intermediate-A

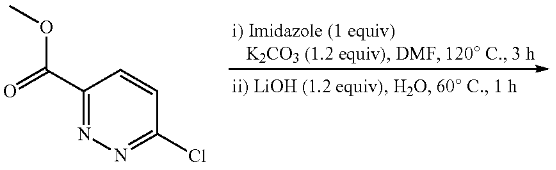

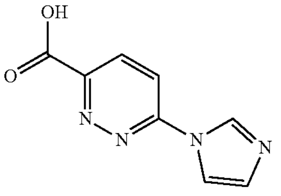

A 6-(1H-imidazol-1-yl)pyridazine-3-carboxylic acid, A: To a suspension of methyl 6-chloropyridazine-3-carboxylate (1 g, 5.8 mmol) and imidazole (400 mg, 5.8 mmol) in dry DMF (10 mL), was added $K_2CO_3$ (950 mg, 6.8 mmol) and the reaction mixture was stirred at 120° C. for 3 h. The reaction was monitored by LCMS. After complete conversion to methyl 6-(1H-imidazol-1-yl)pyridazine-3-carboxylate, 2.5 M aq. LiOH (2.8 mL, 6.96 mmol) was added to the reaction mixture and stirred at 60° C. for 1 h. The reaction was monitored by LCMS. After completion of the reaction, the reaction mixture was acidified with aq.1 M HCl and the resulting precipitate was filtered and washed with water, to obtain the acid A (720 mg) as an off-white solid which was used in the next step without further purification. LC-MS (ESI+): m/z 191.0 $[M+H]^+$.

Part II: Preparation of Example Compounds

All compounds were prepared using the procedures exemplified below.

Example 1

Scheme 2: Synthesis of Compound 1

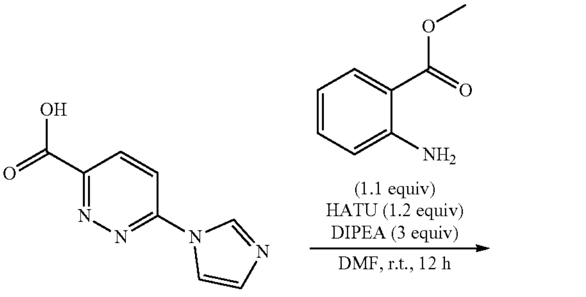

A

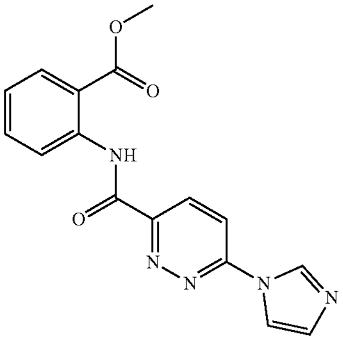

1 methyl 2-(6-(1H-imidazol-1-yl)pyridazine-3-carboxamido)benzoate, 1: Intermediate A (190 mg, 1 mmol), methyl 2-aminobenzoate (166 mg, 1.1 mmol), HATU (456 mg, 1.2 mmol) and DIPEA (0.52 mL, 3 mmol) were dissolved in DMF (5 mL) and stirred at room temperature overnight. After the completion of reaction, solvent was evaporated under reduced pressure and the resulting crude material was purified by silica-gel column chromatography using 2-5% MeOH in DCM to obtain the compound 1 as an off-white solid (226 mg). LC-MS (ESI+): m/z 324.27 $[M+H]^+$.

Scheme 3

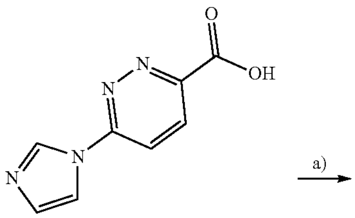

-continued

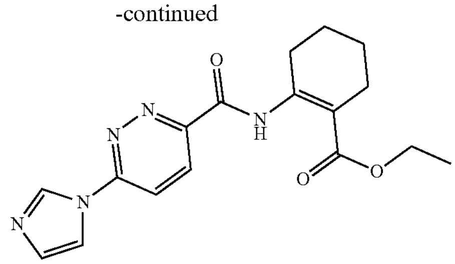

[a]Reagents and conditions:
a) thionyl choride, reflux, 3 h; ethyl 2-aminocyclohex-1-ene-1-carboxylate, DIPEA, acetonitrile, rt, 30 min Ethyl 2-(6-(1H-imidazol-1-yl)pyridazine-3-carboxamido)cyclohex-1-ene-1-carboxylate: 6-(1H-imidazol-1-yl)pyridazine-3-carboxylic acid (19 mg, 0.1 mmol) was dissolved in 0.3 mL of thionyl chloride and the mixture was heated under reflux for 3 h. Then, the excess thionyl was removed under vacuum. The solid was dissolved in 0.5 mL of anhydrous acetonitrile and a solution of ethyl 2-amino-cyclohex-1-ene-1-carboxylate (16.9 mg, 0.1 mmol) and DIPEA (26.1 μL, 0.15 mmol) in 0.5 mL of anhydrous acetonitrile was added at room temperature. After stirring for 30 minutes, the crude mixture was filtered and purified by prep-HPLC to give the product (6.8 mg, 20% yield).

Scheme 4: Synthesis of Compound 8

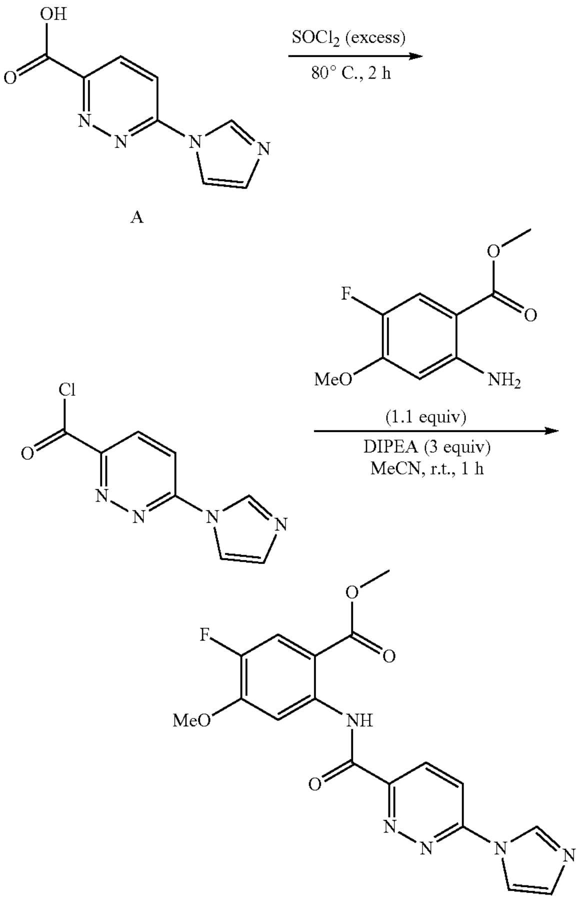

8 methyl 2-(6-(1H-imidazol-1-yl)pyridazine-3-carboxamido)-5-fluoro-4-methoxybenzoate, 8: Intermediate A (190 mg, 1 mmol) was stirred in the presence of $SOCl_2$ (5 mL) at 80° C. for 2 h. The volatiles were then removed followed by the addition of a solution of the methyl 2-amino-5-fluoro-4-methoxybenzoate (219 mg, 1.1 mmol) and DIPEA (0.52 mL, 3 mmol) in acetonitrile (5 mL). The resulting reaction mixture was stirred at room temperature for 1 h. The reaction was monitored by LCMS. After the completion of reaction, solvent was removed, and the resulting crude material was purified by silica-gel column chromatography using 2-5% MeOH in DCM to obtain the compound 8 as an off white solid (223 mg). LC-MS (ESI+): m/z 372.1 $[M+H]^+$.

Example 2-Li

Scheme 5: Synthesis of Compound 2-Li

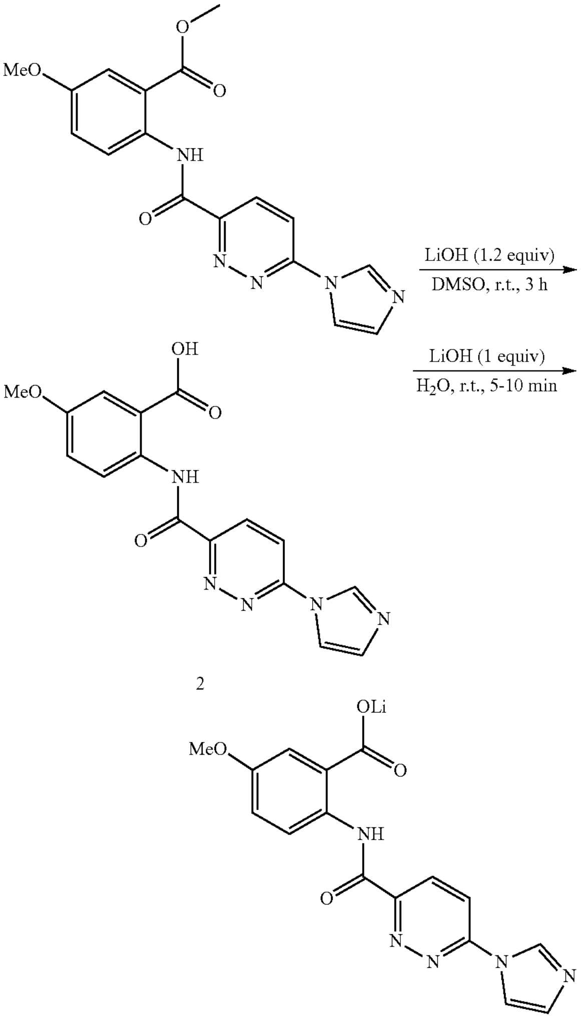

2-Li lithium 2-(6-(1H-imidazol-1-yl)pyridazine-3-carboxamido)-5-methoxybenzoate, 2-Li: methyl 2-(6-(1H-imidazol-1-yl)pyridazine-3-carboxamido)-5-methoxybenzoate was prepared by using the procedure followed for the compound 1 (Scheme C). The resulting ester (20 mg, 0.057 mmol) was dissolved in DMSO (0.8 mL) and then aq. 0.1M LiOH (0.68 mL, 1.2 mmol) was added followed by stirring at room temperature until completion of the reaction (~3 h). The reaction was monitored by LCMS. Then, the reaction mixture was acidified with 1M HCl via dropwise addition to generate the desired acid. The obtained precipitate was isolated and washed with water to give acid 2 as an off-white solid. LC-MS (ESI+): m/z 340.4 $[M+H]^+$. Acid 2 (10.2 mg, 0.03 mmol) was further suspended in 2.5 mL of water (0.25 mL/mg) and sonicated for 20 min to prepare a homogenous suspension. Thereafter, 1M LiOH (30 μL, 0.03 mmol) was added to obtain a clear solution of the lithium salt, which was then filtered to remove any insoluble particles. The resulting solution was lyophilized to obtain the corresponding lithium salt 2-Li. LC-MS (ESI+): m/z 340.4 $[M+H]^+$.

5

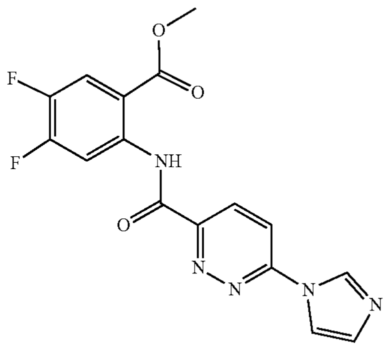

methyl 2-(6-(1H-imidazol-1-yl)pyridazine-3-carboxamido)-4,5-difluorobenzoate, 5: Compound 5 was prepared by using the procedure followed for the compound 1 (Scheme C). LC-MS (ESI+): m/z 360.21 $[M+H]^+$.

Example 6-Li

6-Li

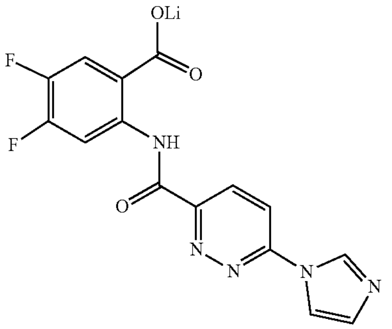

lithium 2-(6-(1H-imidazol-1-yl)pyridazine-3-carboxamido)-4,5-difluorobenzoate, 6-Li: Compound 6-Li was prepared by using the procedure followed for the compound 2-Li (Scheme D). LC-MS (ESI+): m/z 346.1 $[M+H]^+$.

Example 7-Li

7-Li

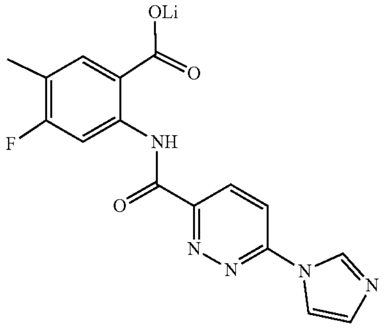

lithium 2-(6-(1H-imidazol-1-yl)pyridazine-3-carboxamido)-4-fluoro-5-methylbenzoate, 7-Li: Compound 7-Li was prepared by using the procedure followed for the compound 2-Li (Scheme D). LC-MS (ESI+): m/z 342.11 $[M+H]^+$.

Example 8

Scheme F: Synthesis of Compound 8

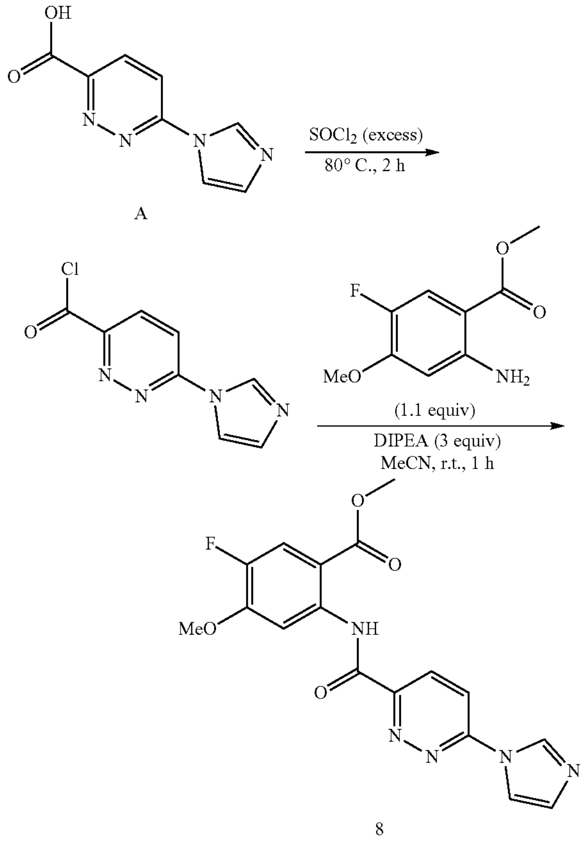

methyl 2-(6-(1H-imidazol-1-yl)pyridazine-3-carboxamido)-5-fluoro-4-methoxybenzoate, 8: Intermediate A (190 mg, 1 mmol) was stirred in the presence of $SOCl_2$ (5 mL) at 80° C. for 2 h. The volatiles were then removed followed by the addition of a solution of the methyl 2-amino-5-fluoro-4-methoxybenzoate (219 mg, 1.1 mmol) and DIPEA (0.52 mL, 3 mmol) in acetonitrile (5 mL). The resulting reaction mixture was stirred at room temperature for 1 h. The reaction was monitored by LCMS. After the completion of reaction, solvent was removed, and the resulting crude material was purified by silica-gel column chromatography using 2-5% MeOH in DCM to obtain the compound 8 as an off white solid (223 mg). LC-MS (ESI+): m/z 372.1 $[M+H]^+$.

Scheme G: Synthesis of Dimethyl Oxazinone Compound

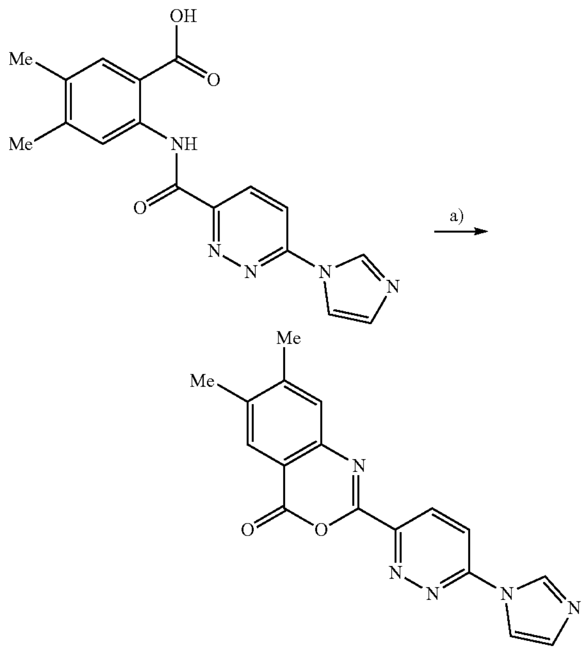

[a]Reagents and conditions:
a) thionyl chloride, reflux, 3 h; DIPEA, acetonitrile, rt, 30 min 2-(6-(1H-imidazol-1-yl)pyridazin-3-yl)-6,7-dimethyl-4H-benzo[d][1,3]oxazin-4-one: 2-(6-(1H-imidazol-1-yl)pyridazine-3-carboxamido)-4,5-dimethylbenzoic acid (33.7 mg, 0.1 mmol) was dissolved in 0.3 mL of thionyl chloride and the mixture was heated under reflux for 3 h. Then, the excess thionyl was removed under vacuum. The solid was dissolved in 0.5 mL of anhydrous acetonitrile and a solution of DIPEA (26.1 μL, 0.15 mmol) in 0.5 mL of anhydrous acetonitrile was added at room temperature. After stirring for 30 minutes, the obtained precipitate was isolated and washed with acetonitrile to give the product (26.2 mg, 82 yield).

Scheme H: Synthesis of Difluoro Oxazinone Compound

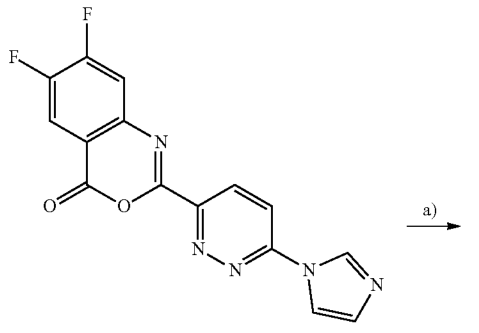

-continued

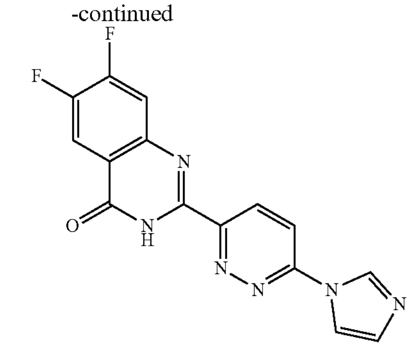

[a]Reagents and conditions: a) formamide, microwave, 200° C.

2-(6-(1H-imidazol-1-yl)pyridazin-3-yl)-6,7-difluoroquinazolin-4(3H)-one: A solution of 2-(6-(1H-imidazol-1-yl)pyridazin-3-yl)-6,7-difluoro-4H-benzo[d][1,3]oxazin-4-one (32.7 mg, 0.1 mmol) in 2 mL of formamide was placed in 10 mL microwave vial which was sealed and irradiated at a temperature of 200° C. for 15 min. The reaction was monitored by LCMS. After the completion of reaction, 4 mL of methanol was added and the crude mixture was filtered and purified by prep-HPLC to give the product (13.0 mg, 40% yield).

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

What is claimed is:

1. A method of stimulating expression of interferon genes, comprising administering to a patient an effective dose of a compound of any one of the following formulae:

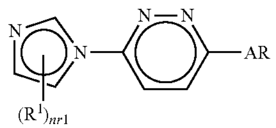

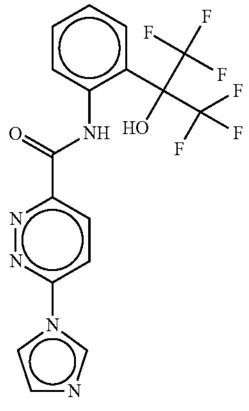

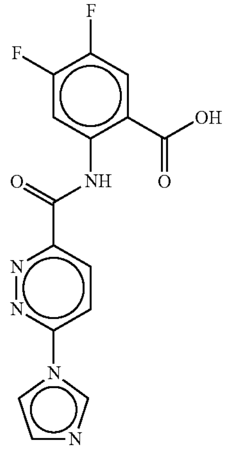

-continued
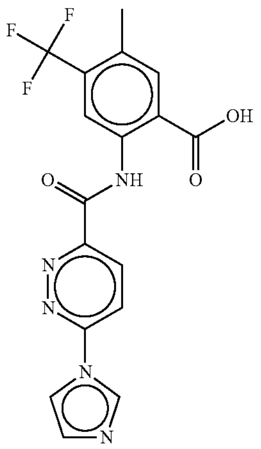
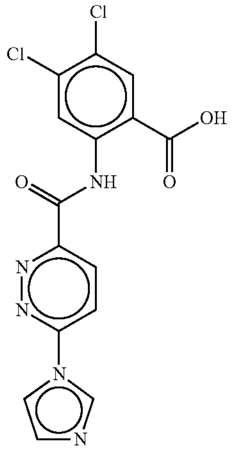
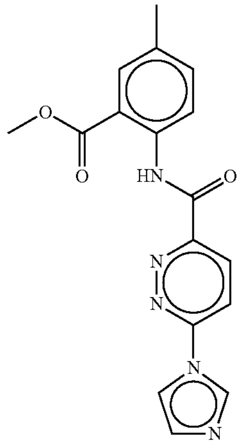
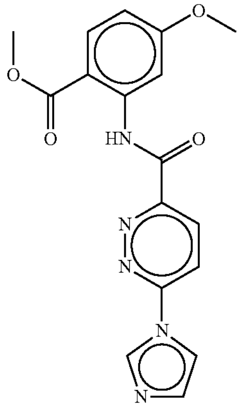
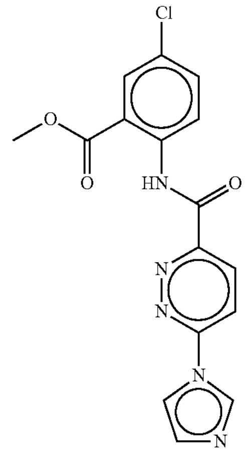
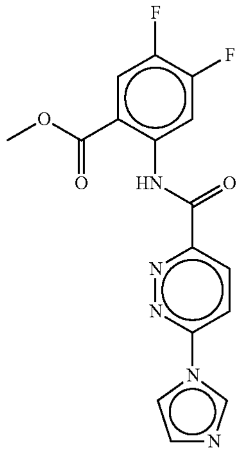
-continued
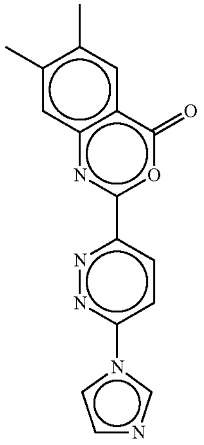
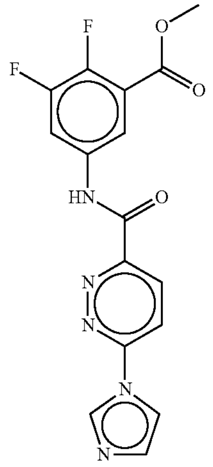
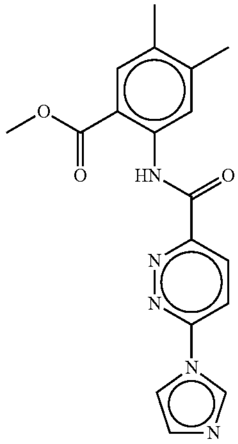
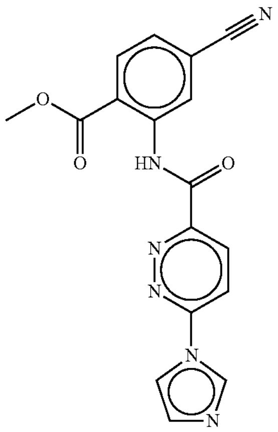
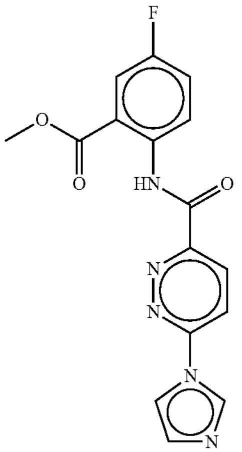
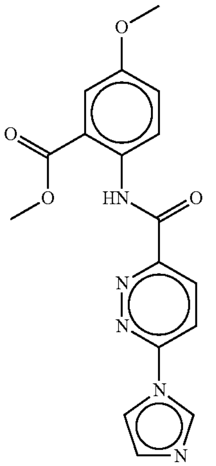

-continued
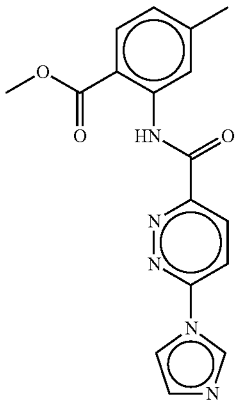
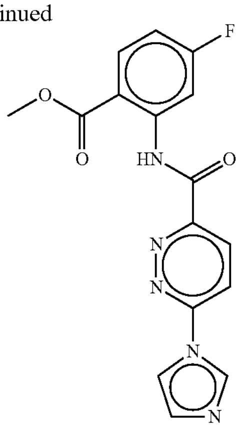
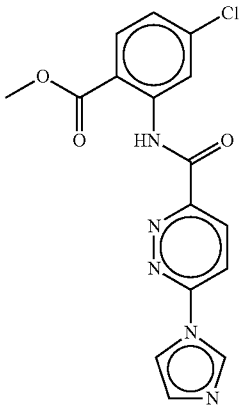
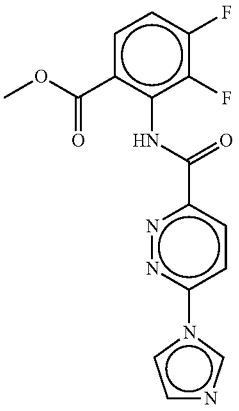
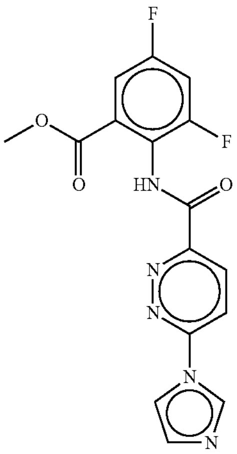
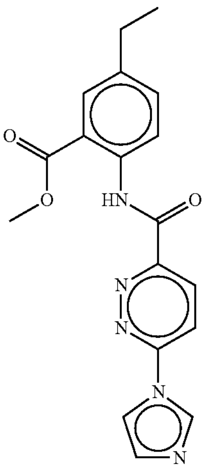
-continued
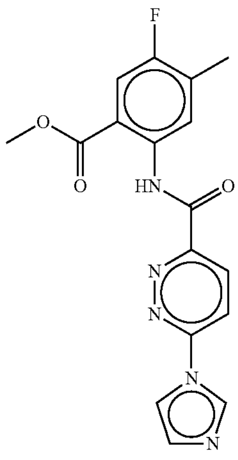
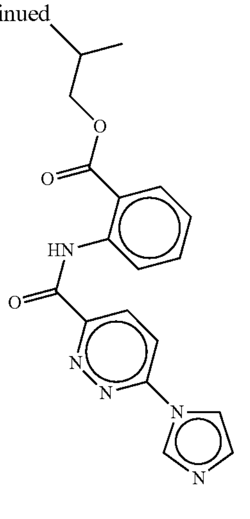
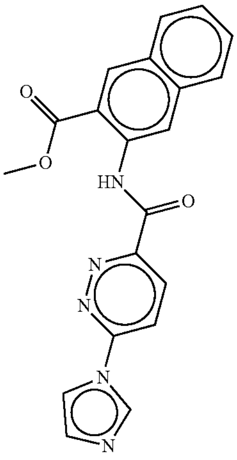
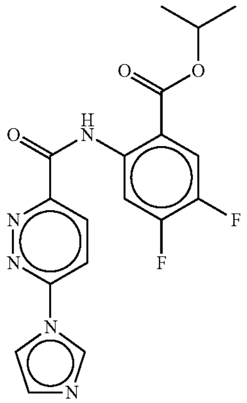
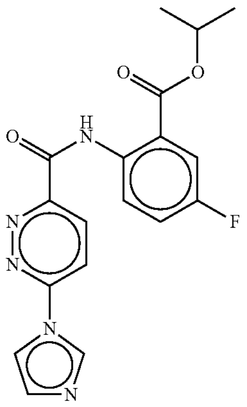
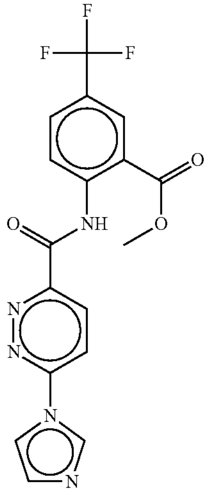

-continued
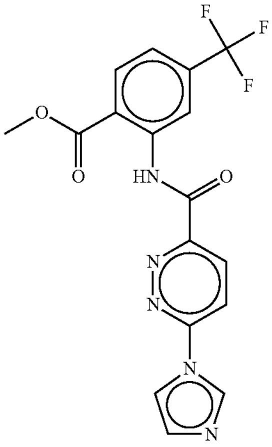
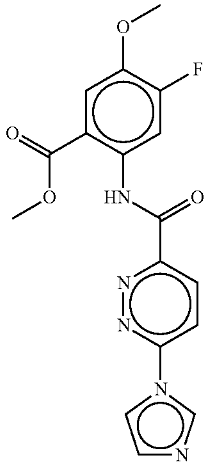
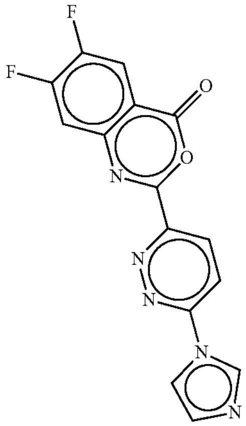
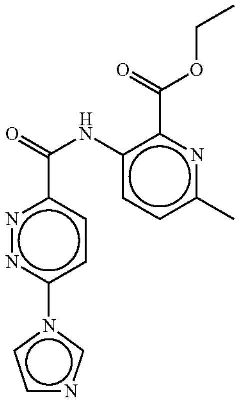
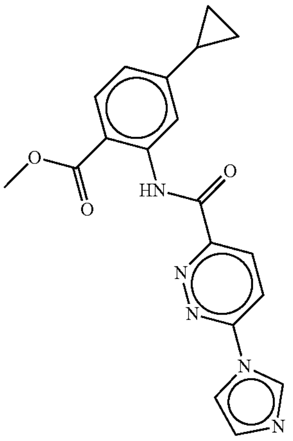
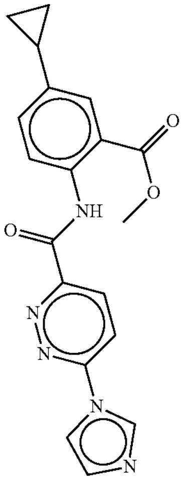
-continued
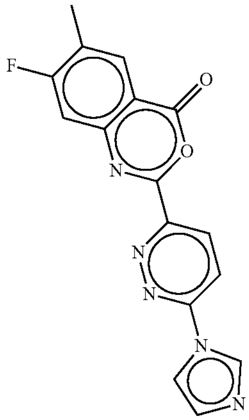
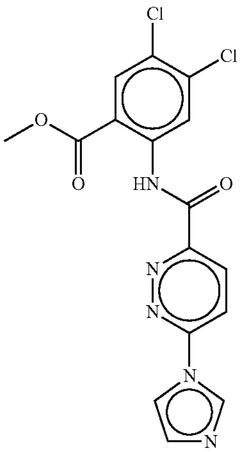
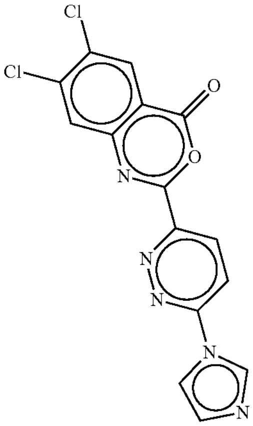
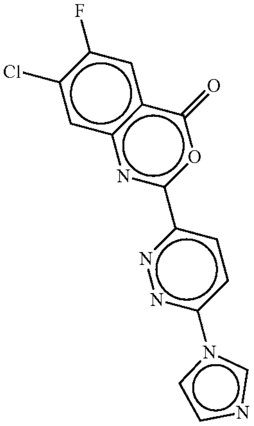
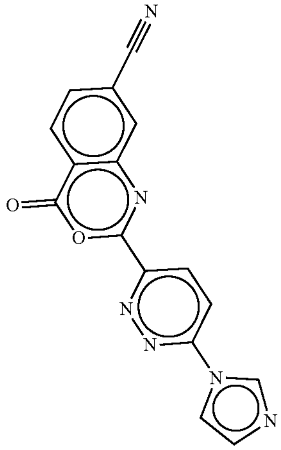
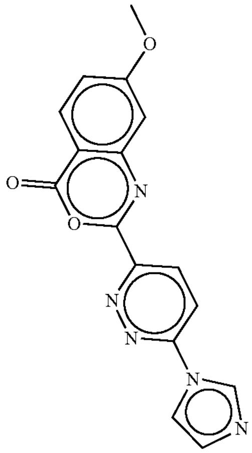

-continued
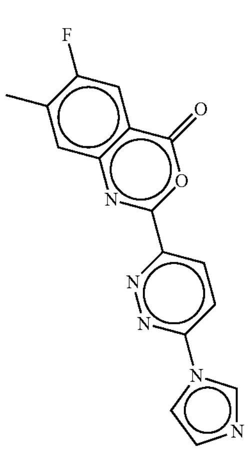
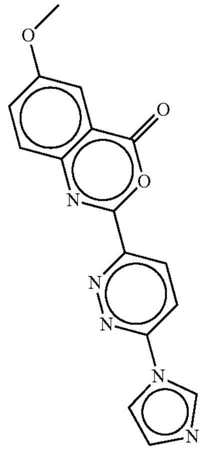
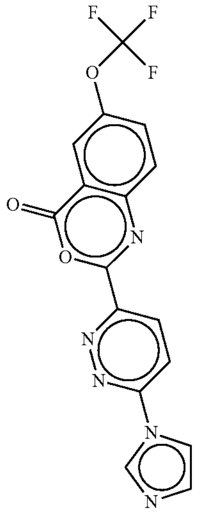
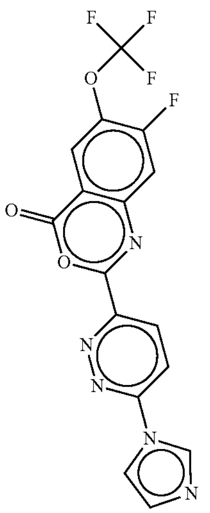
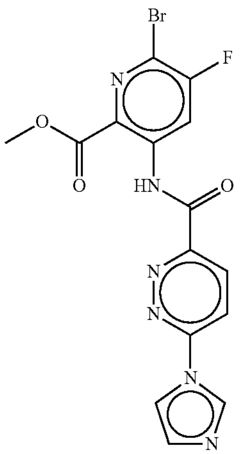
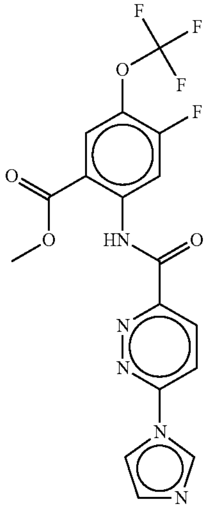
-continued
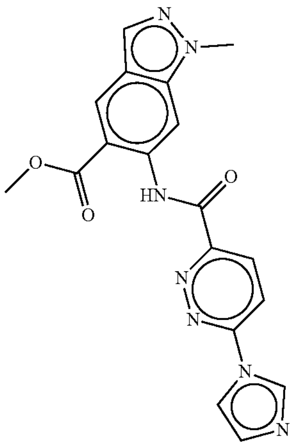
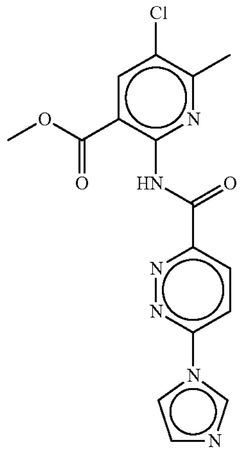
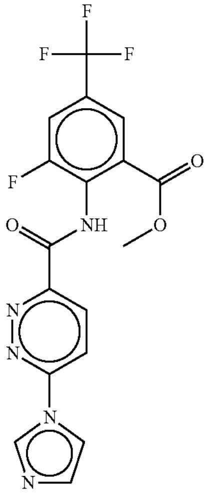
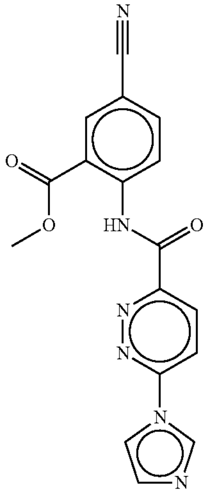
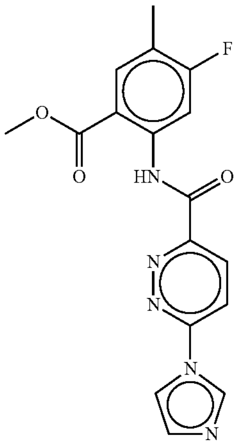
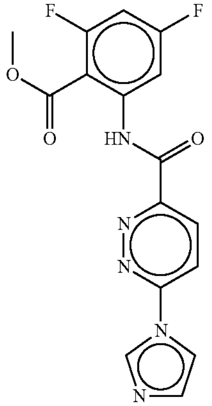

-continued
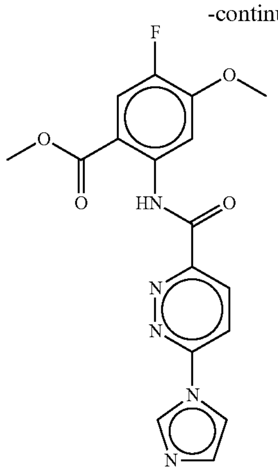
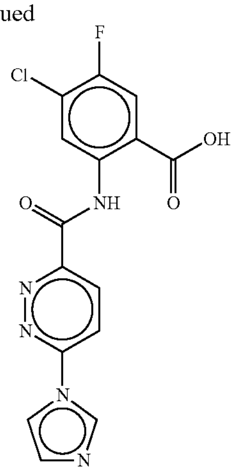
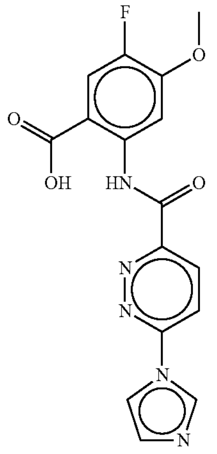
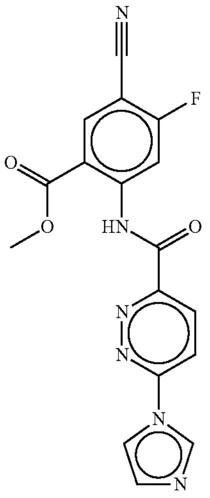
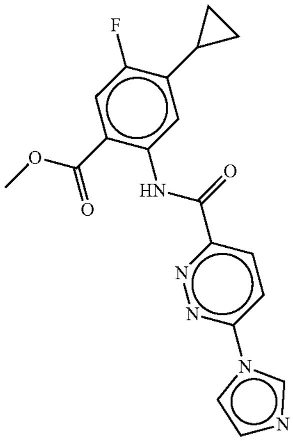
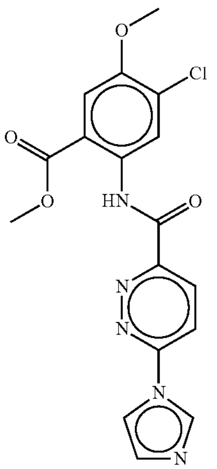
-continued
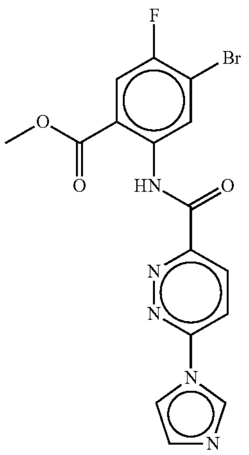
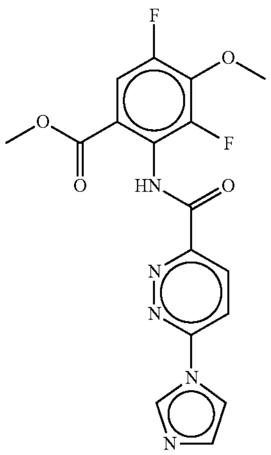
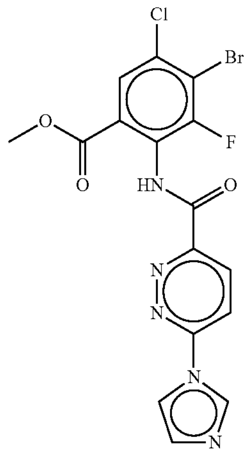
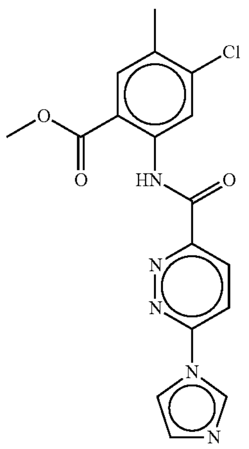
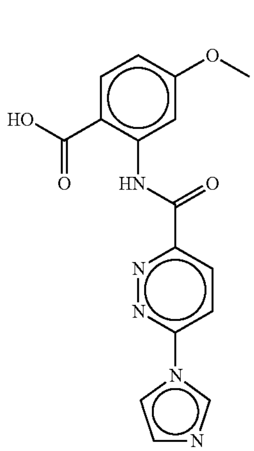
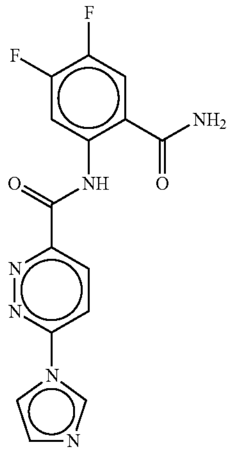

147
-continued
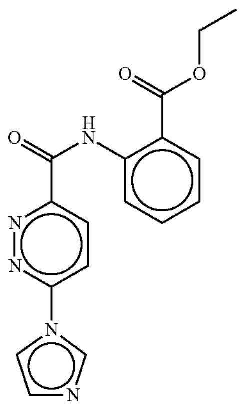
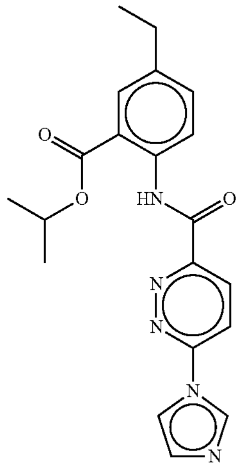
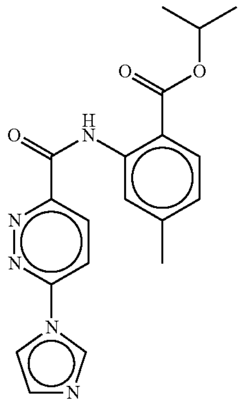
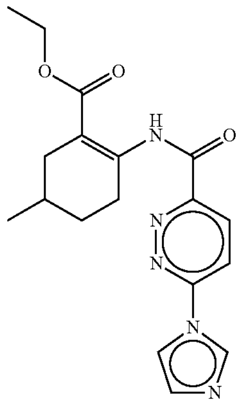
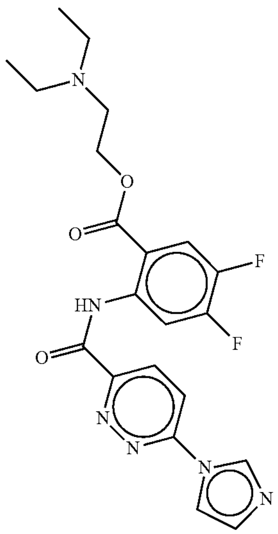
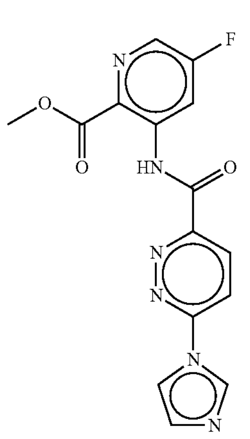
148
-continued
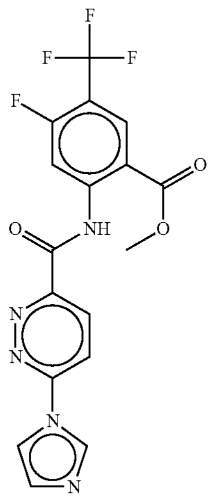
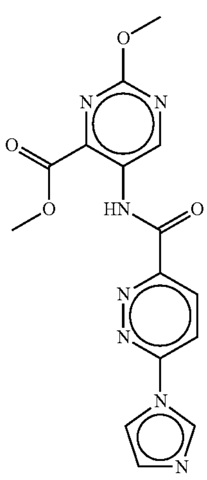
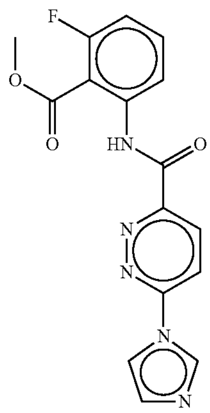
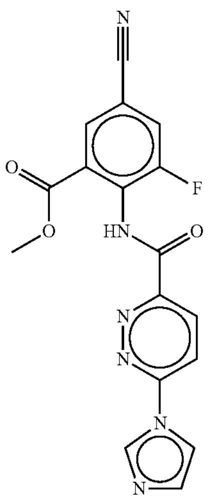
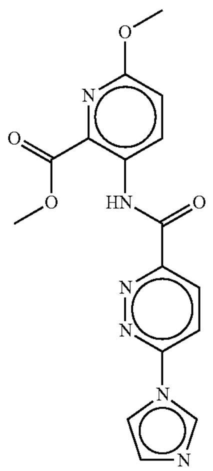
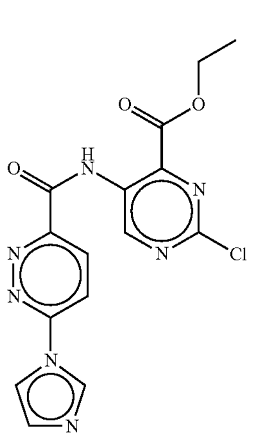

-continued
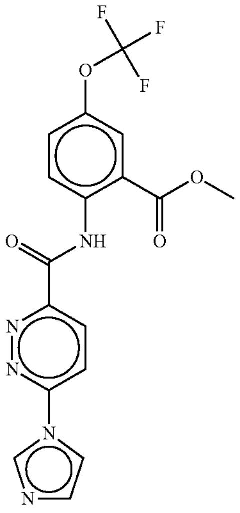
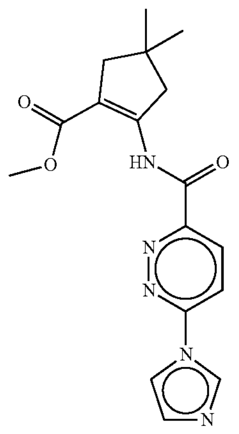
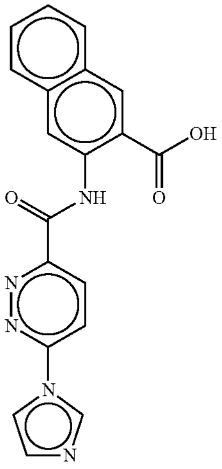
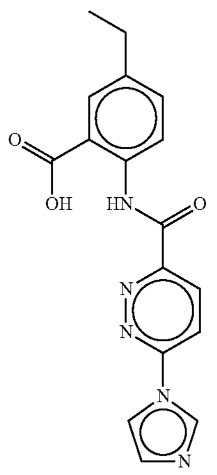
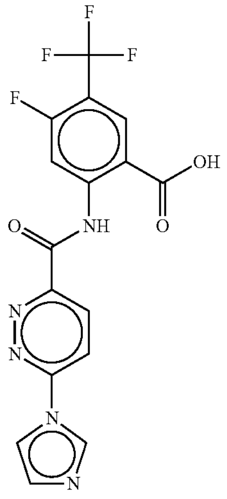
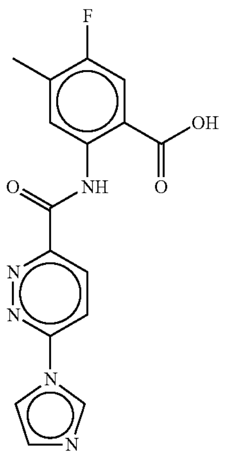
-continued
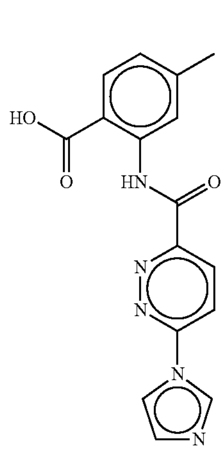
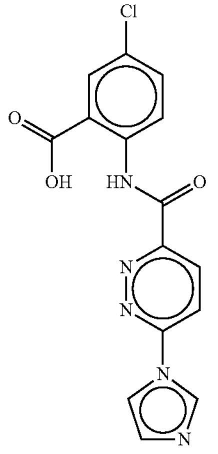
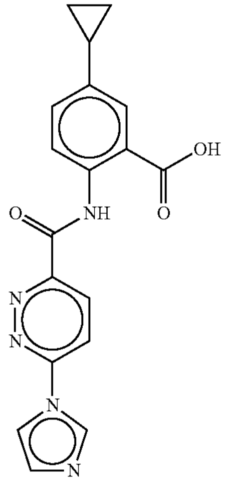
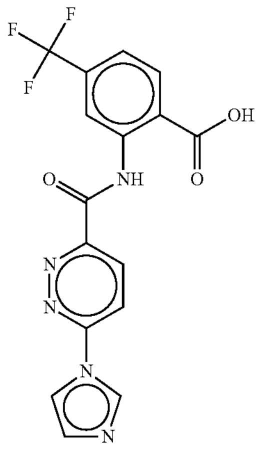
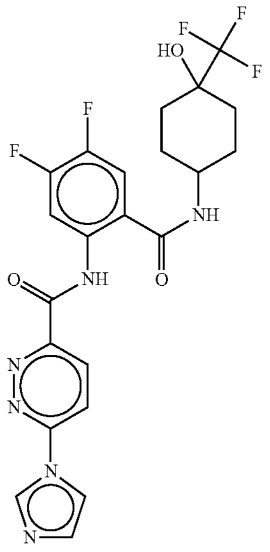
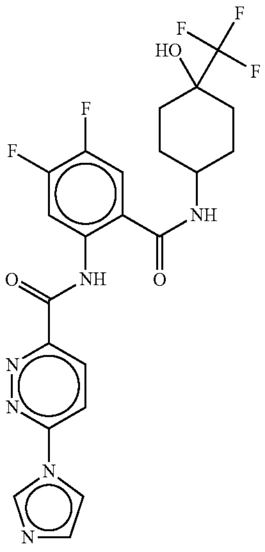

-continued
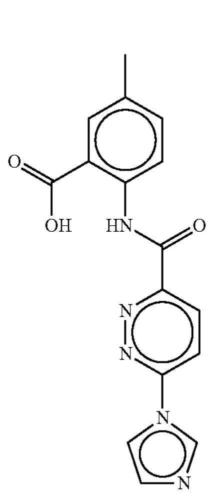
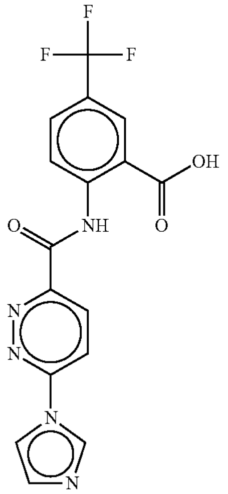
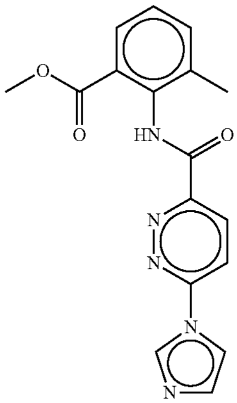
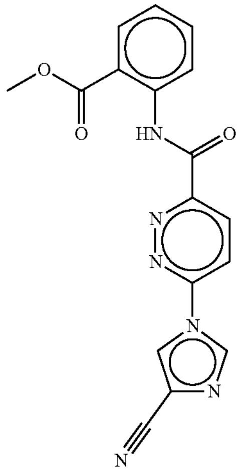
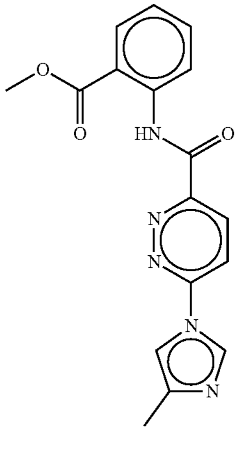
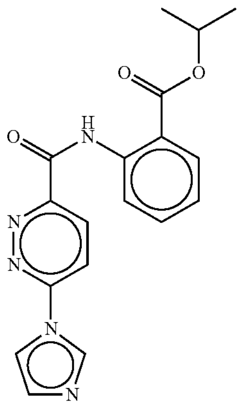
-continued
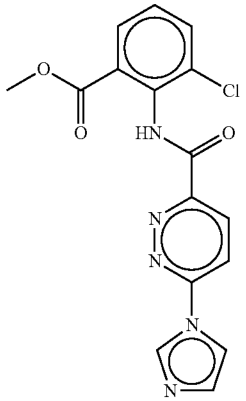
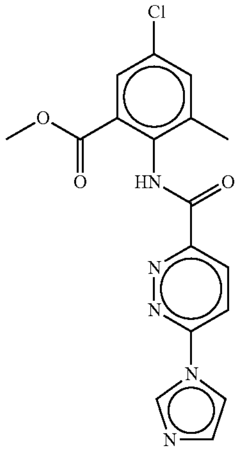
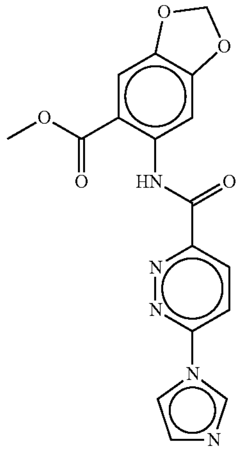
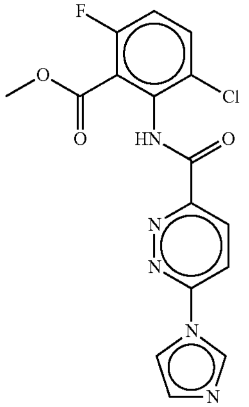
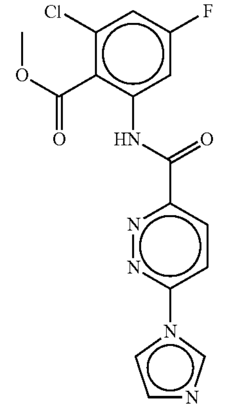
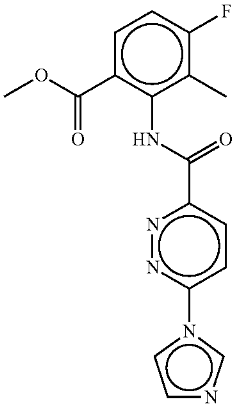
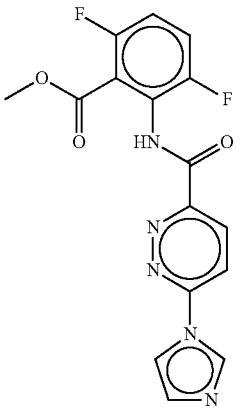
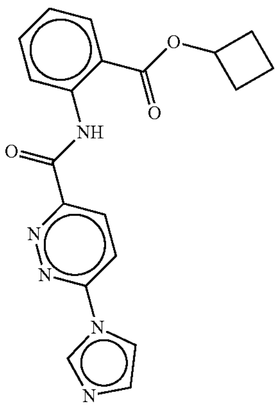

-continued
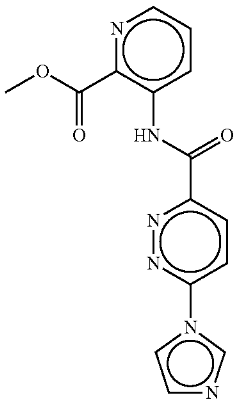
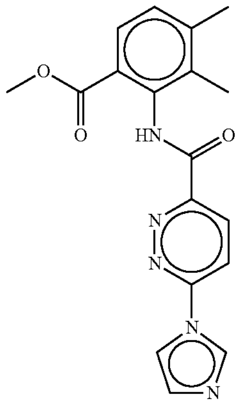
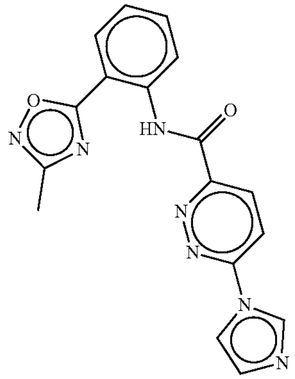
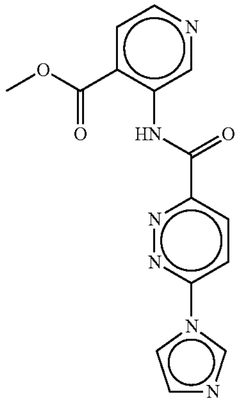
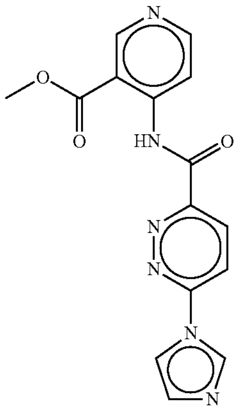
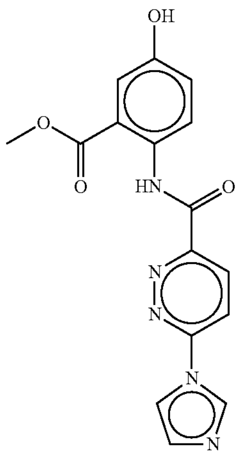
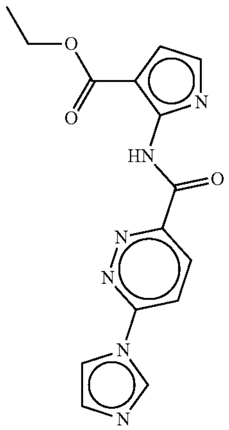
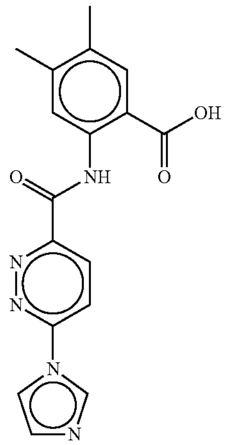
-continued
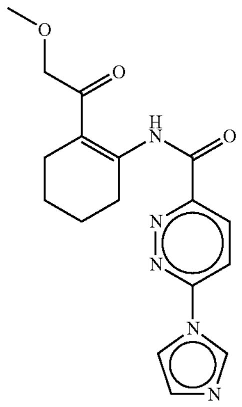
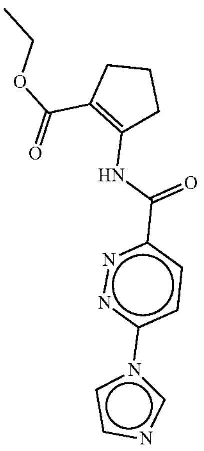
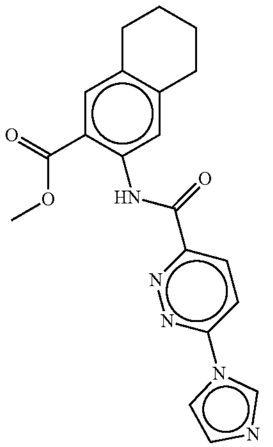
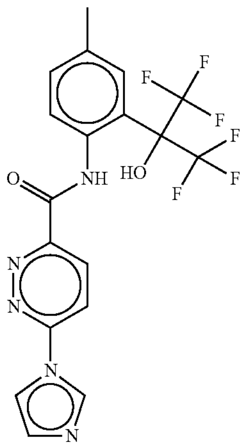
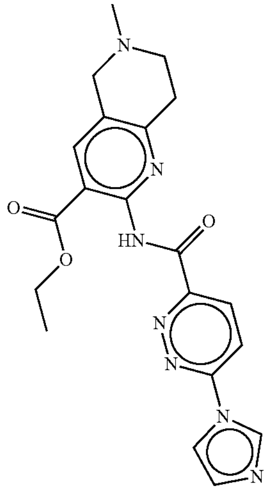
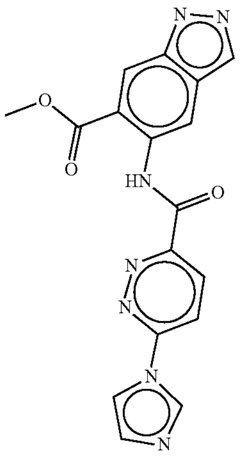

-continued
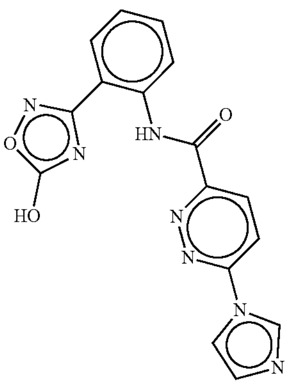
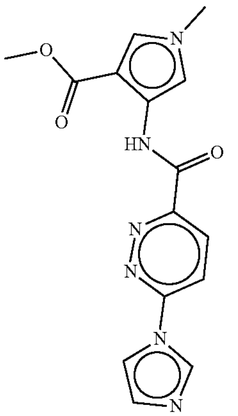
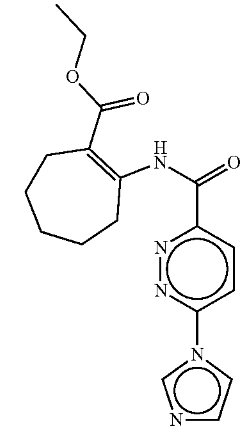
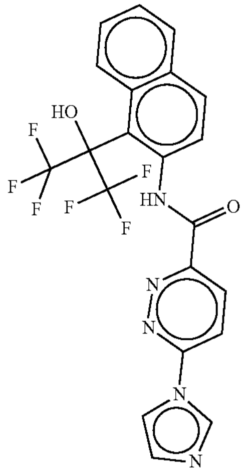
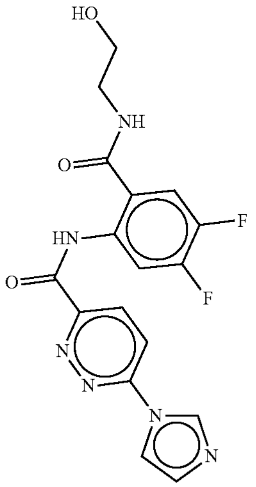
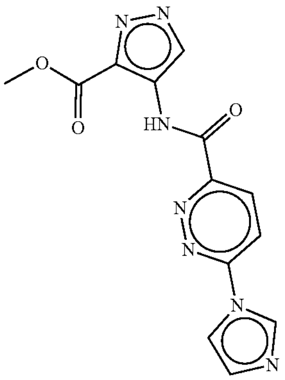
-continued
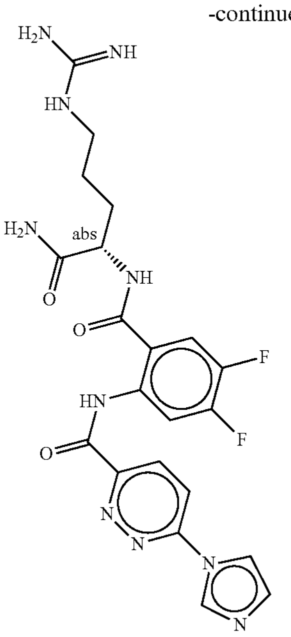
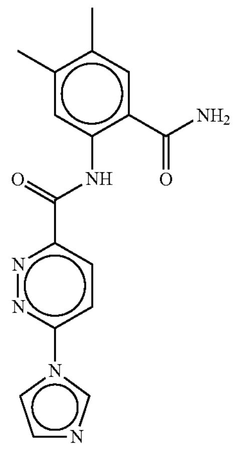
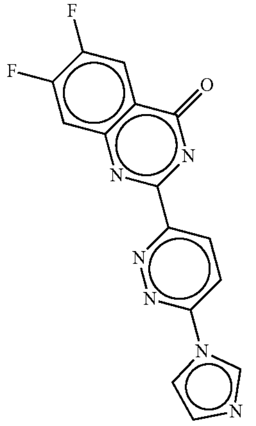
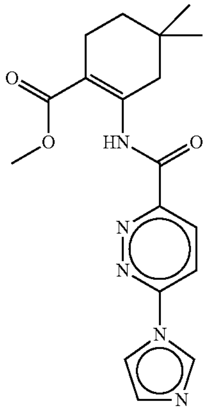
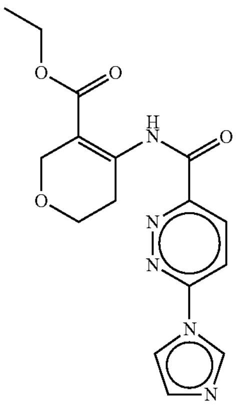
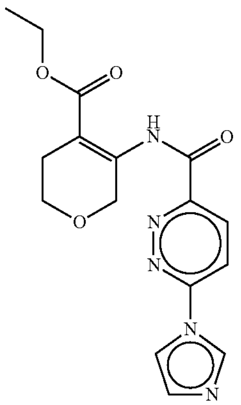

-continued
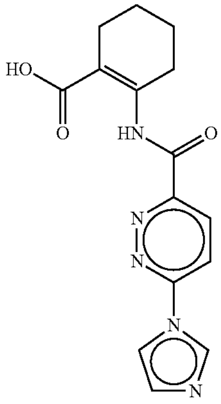
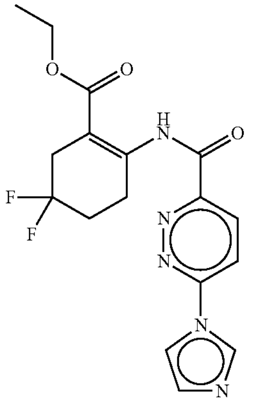
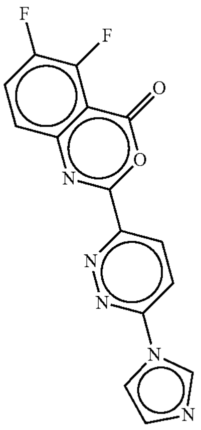
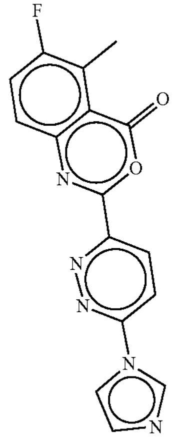
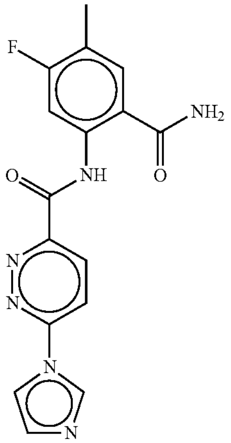
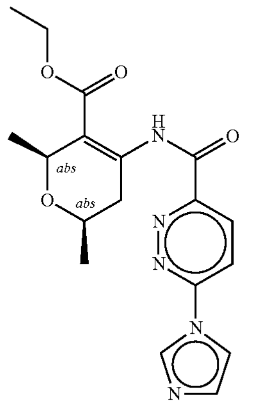
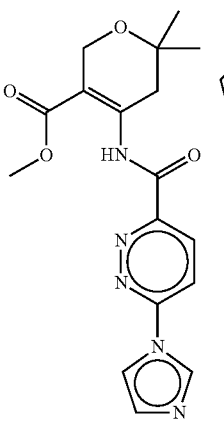
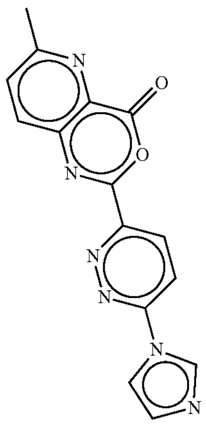
-continued
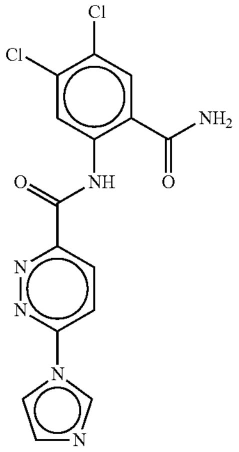
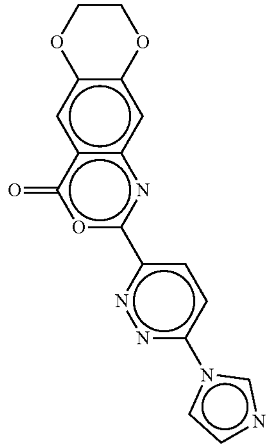
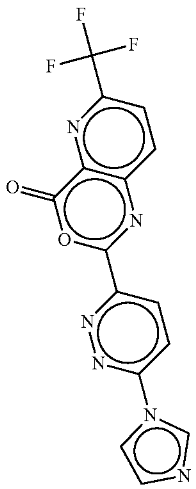
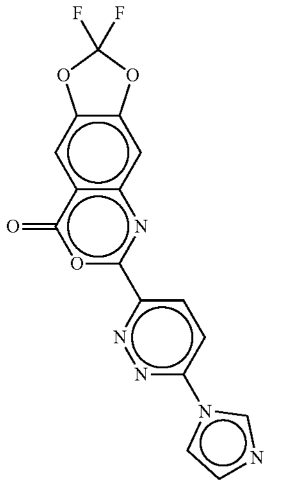
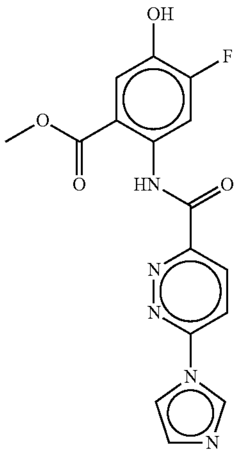
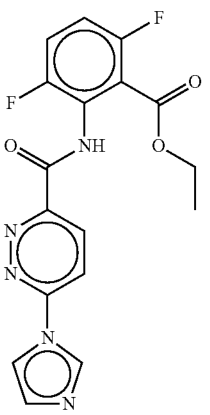

-continued
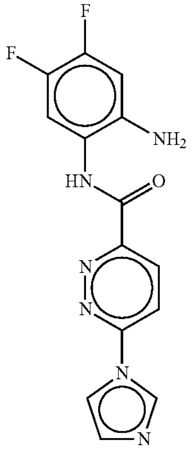
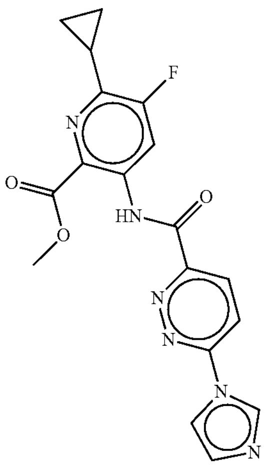
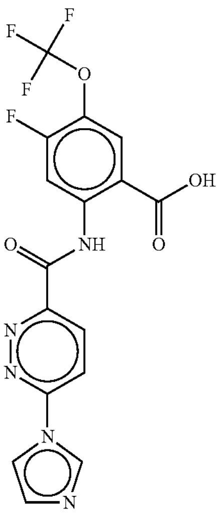
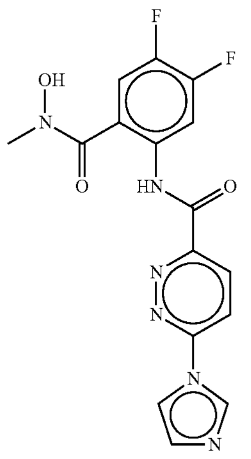
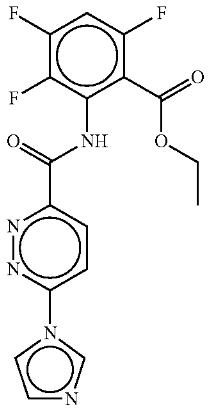
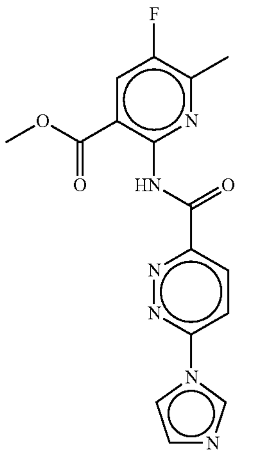
-continued
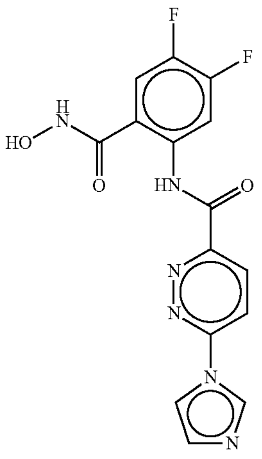
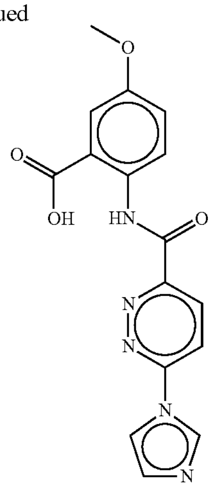
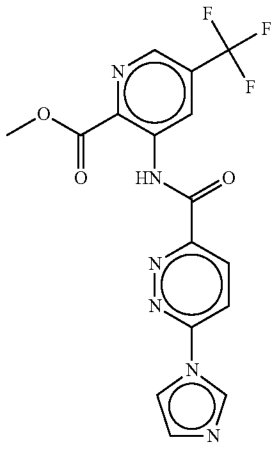
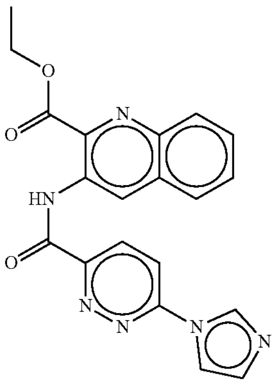
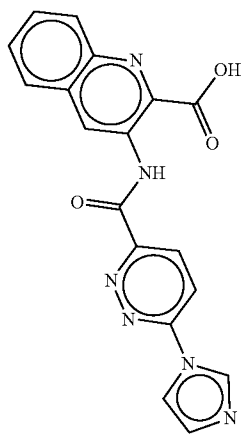
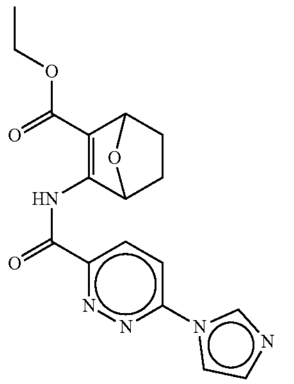

-continued
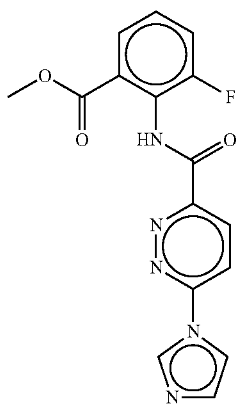
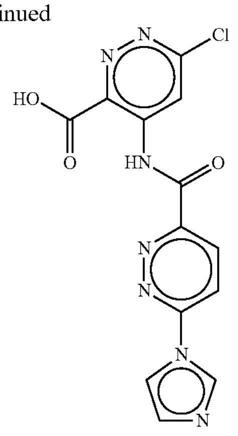
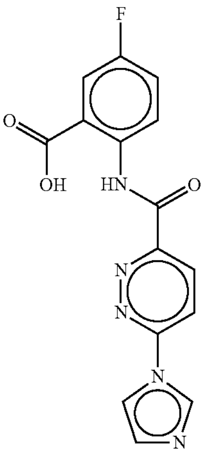
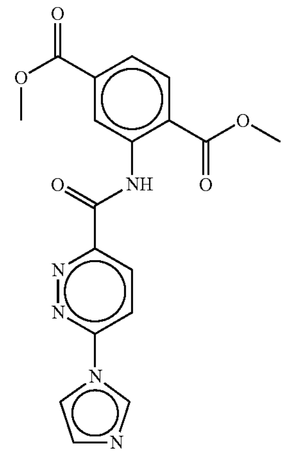
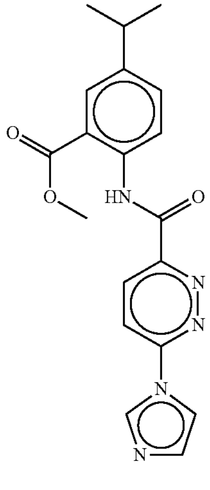
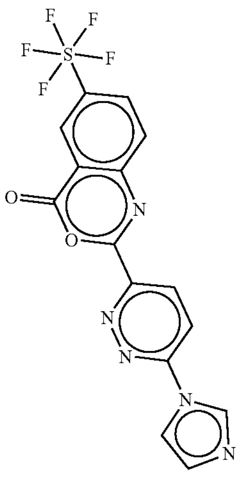
-continued
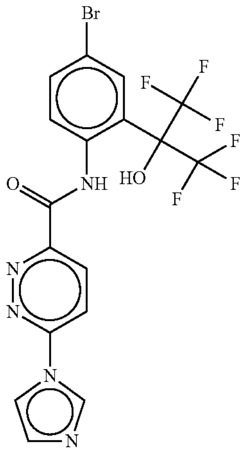
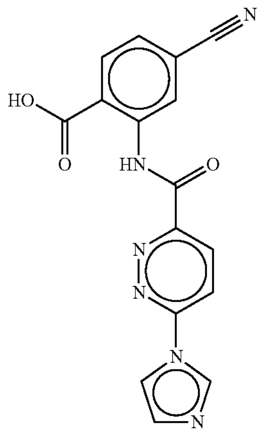
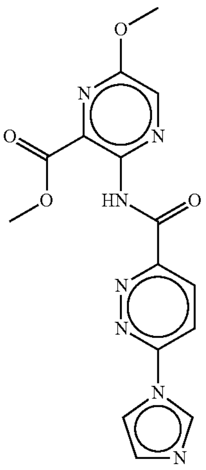
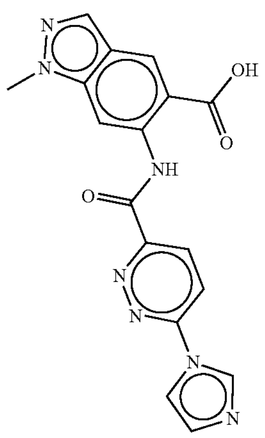
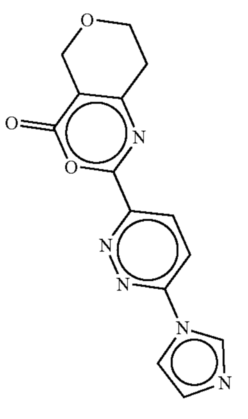
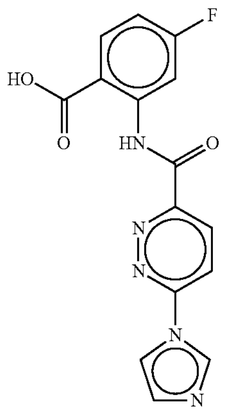

-continued

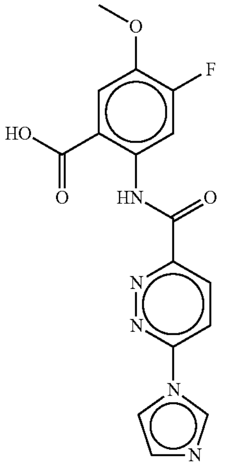

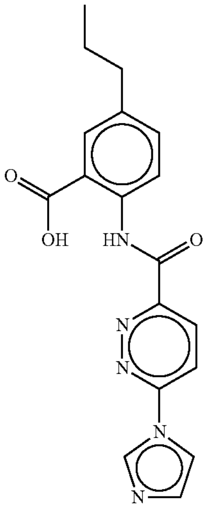

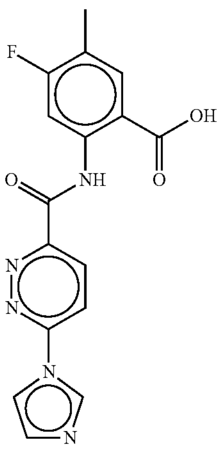

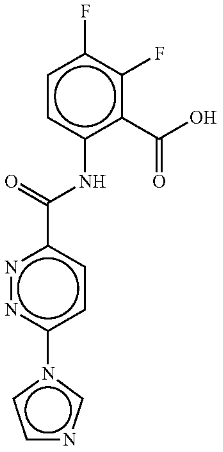

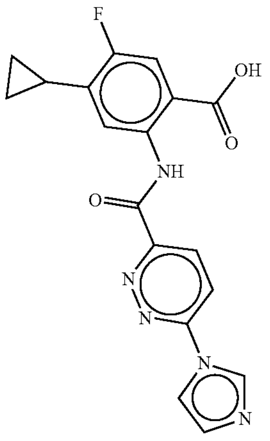

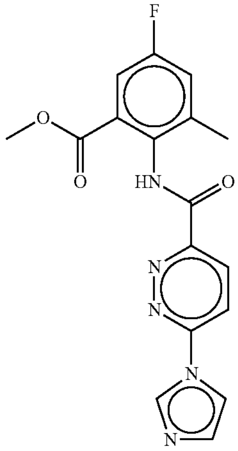

-continued

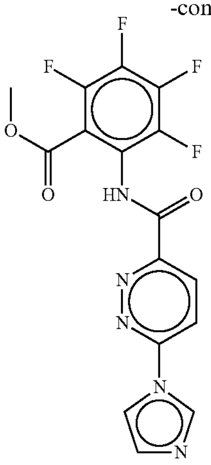

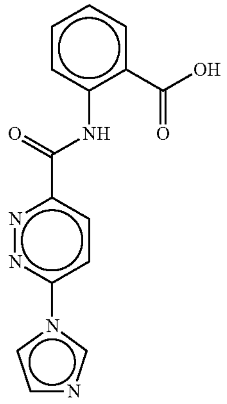

or a pharmaceutically acceptable salt thereof.

2. The method of claim 1, wherein administering comprises oral or intratumoral administration, or both.

3. The method of claim 1, wherein administering comprises administering to the patient as an antibody-drug conjugate, or in a liposomal formulation.

4. The method of claim 1, further comprising administration of an effective dose of an immune-checkpoint targeting drug.

5. The method of claim 4, wherein the immune-checkpoint targeting drug comprises an anti-PD-L1 antibody, anti-PD-1 antibody, anti-CTLA-4 antibody, or an anti-4-1BB antibody.

6. The method of claim 1, further comprising administration of ionizing radiation or anticancer drugs.

7. A method of treating a tumor in a patient, comprising administering to the patient an effective dose of an agonist of the Stimulator of Interferon Genes (STING), comprising a compound of formula (I)

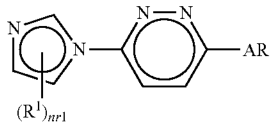

(I)

wherein each $R^1$ is independently (C1-C4)alkyl, or CN, nr1 is 0, 1, 2, or 3, provided that each $R^1$ is bonded to a carbon atom; and, AR is a group of formula —C(═O)N(R)$Ar^1$; R is H or (C1-C4)alkyl;

wherein $Ar^1$ is chosen from the group consisting of:

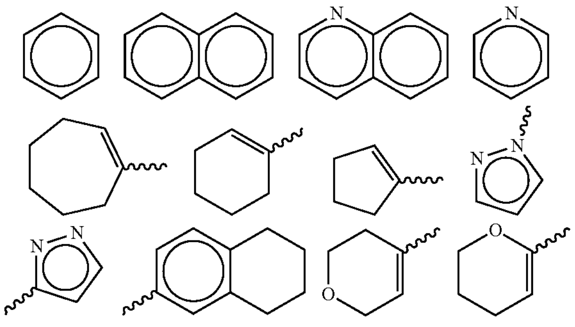

-continued

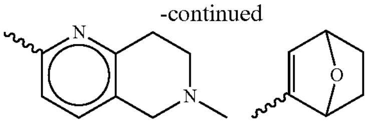

and

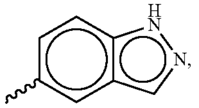

wherein a wavy line indicates a position of bonding; wherein any $Ar^1$ is substituted with nr2 independently selected $R^2$ groups chosen from the group consisting of: —(C1-C4)-alkyl, —(C1-C4)-alkylO, —(C1-C4)-alkylOC(O), —CN, -halo, —(C3-C7)cycloalkyl, —(C1-C4)-alkOC(O), —COOH, (C3-C7)-cycloalkylOC(O), —$SF_5$, -methylenedioxy, -difluoromethylenedioxy, -ethylenedioxy, —$CF_3$, —$OCF_3$, —C(O)$NH_2$, —C(O)NH$(CH_2)_2$OH, —$CH_2$OH, —$NR_2$, —CONH-arginine, —C(O)O$(CH_2)_2NR_2$,

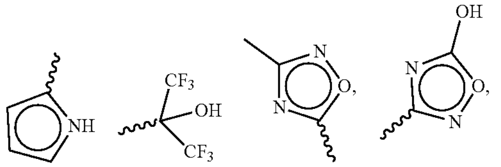

and

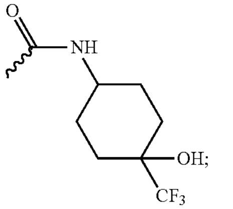

wherein a wavy line indicates a position of bonding; and, nr2=0, 1, 2, or 3;

or,

AR is a group of formula

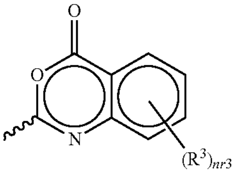

wherein $R^3$ is selected from the group consisting of (C1-C4)-alkyl, (C1-C4)-alkylO, (C1-C4)-alkylOC(O), CN, halo, (C3-C7)cycloalkyl, (C1-C4)-alkOC(O), COOH, (C3-C7)-cycloalkylOC(O), —$SF_5$, methylenedioxy, difluoromethylenedioxy, ethylenedioxy, $CF_3$, —$OCF_3$, $CONH_2$, CONH$(CH_2)_2$OH, $CH_2$OH, $NR_2$, CONH-arginine, and C(O)O$(CH_2)_2NR_2$; and nr3=0, 1, 2, or 3;

or a pharmaceutically acceptable salt thereof.

8. The method of claim 7, wherein administering comprises oral or intratumoral administration, or both.

9. The method of claim 7, wherein administering comprises administering to the patient as an antibody-drug conjugate, or in a liposomal formulation.

10. The method of claim 7, further comprising administration of an effective dose of an immune-checkpoint targeting drug.

11. The method of claim 10, wherein the immune-checkpoint targeting drug comprises an anti-PD-L1 antibody, anti-PD-1 antibody, anti-CTLA-4 antibody, or an anti-4-1BB antibody.

12. The method of claim 7, further comprising administration of ionizing radiation or anticancer drugs.

13. The method of claim 7, wherein the compound of any one of the following formulas:

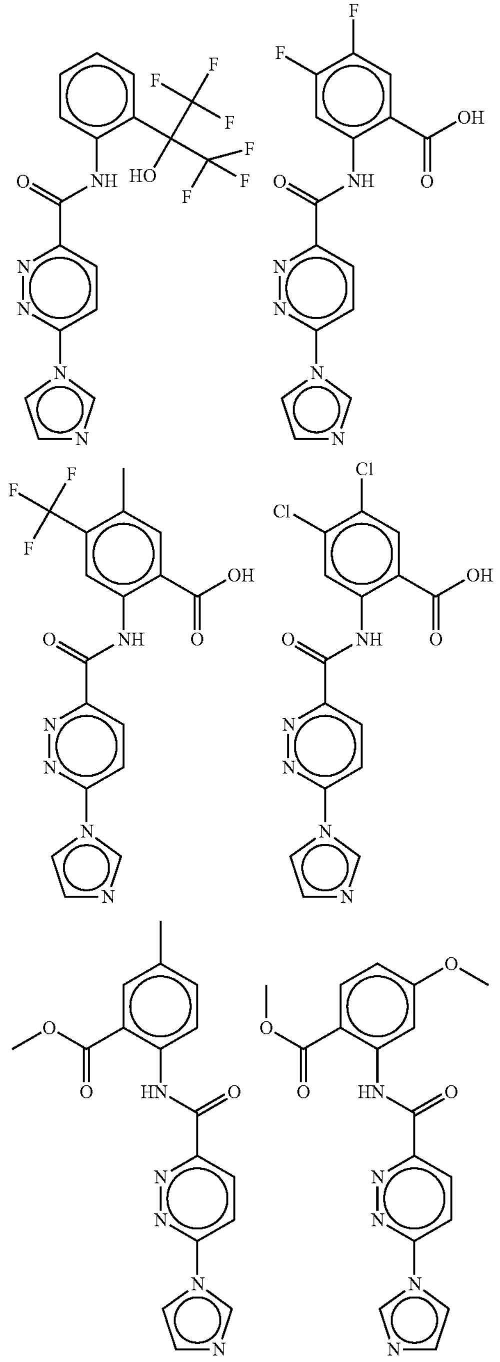

-continued
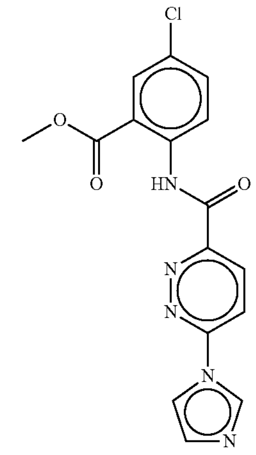
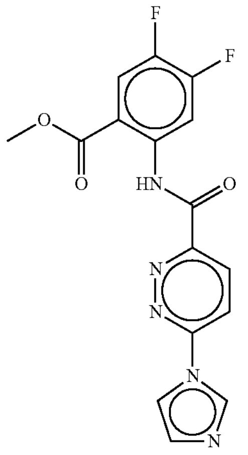
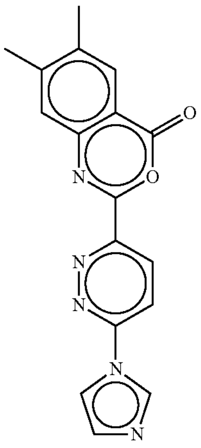
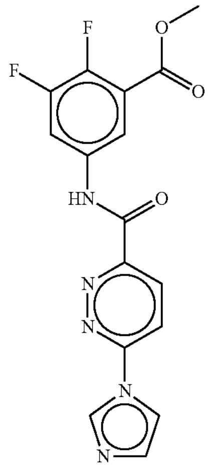
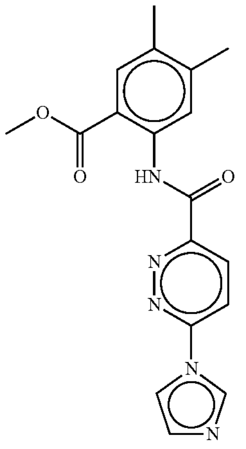
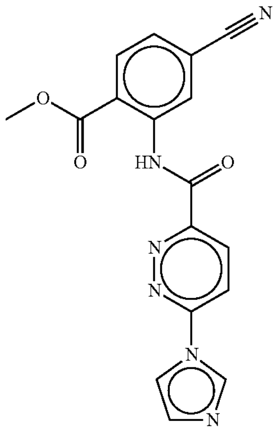
-continued
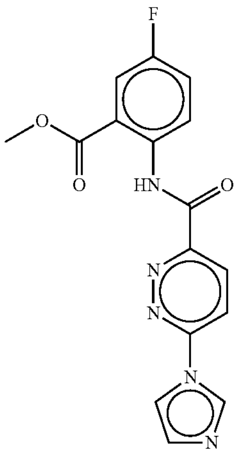
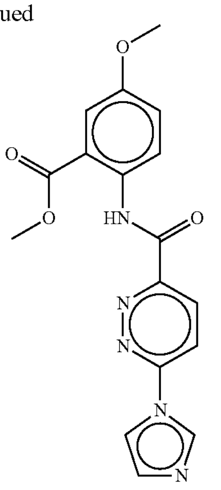
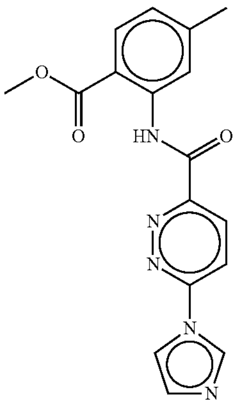
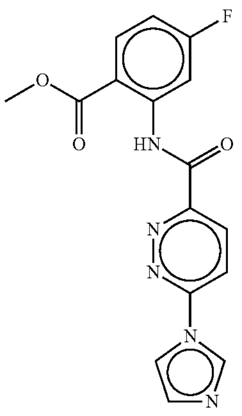
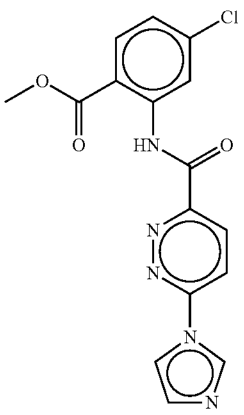
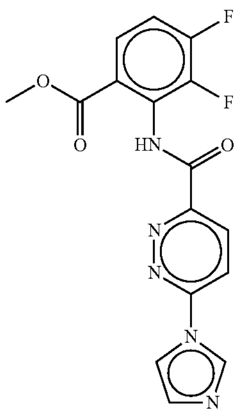

-continued
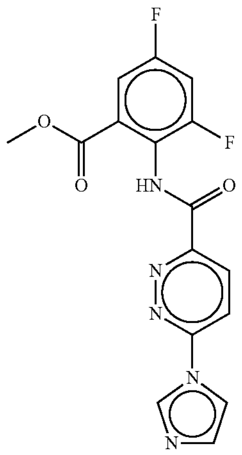
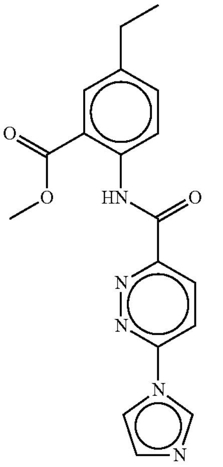
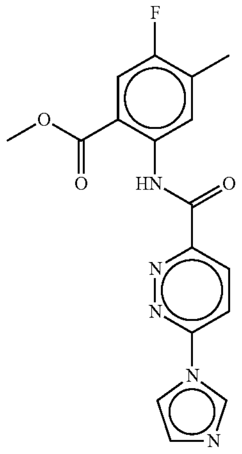
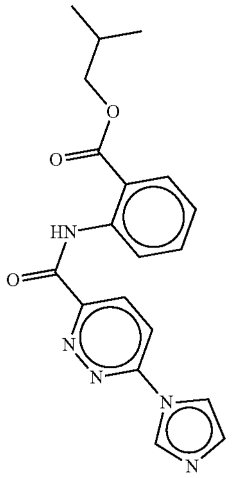
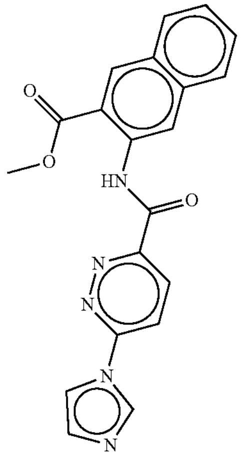
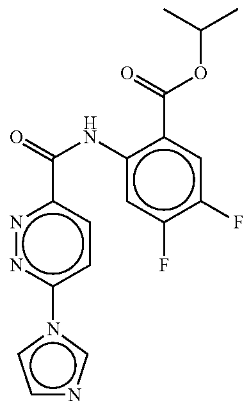
-continued
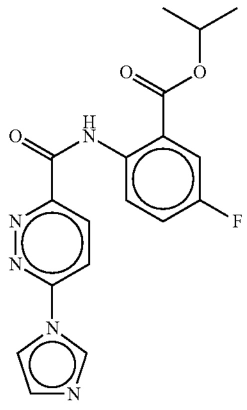
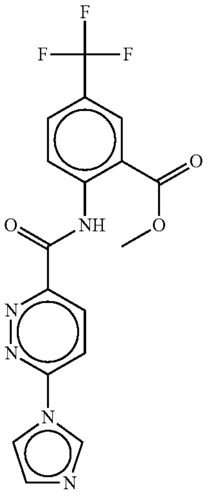
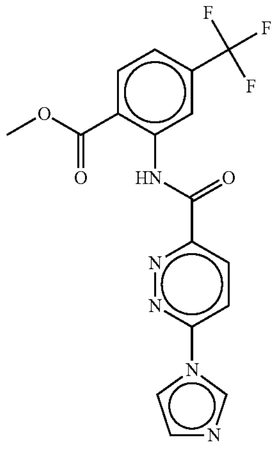
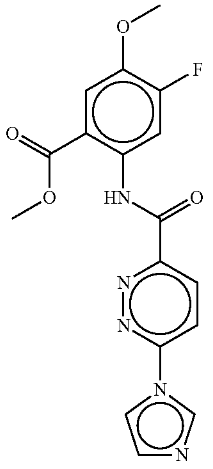
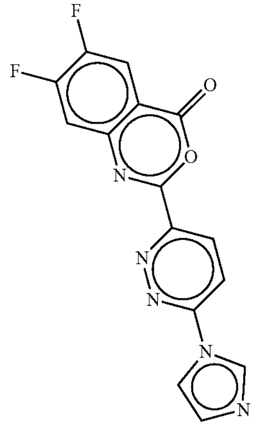
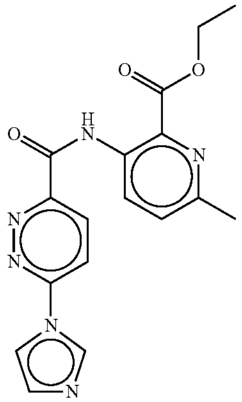

-continued
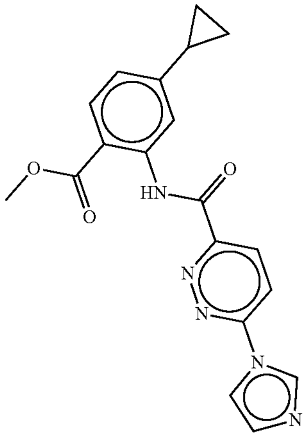
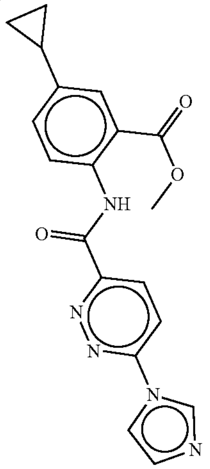
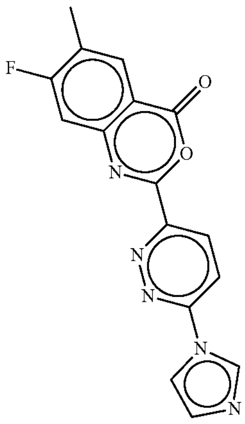
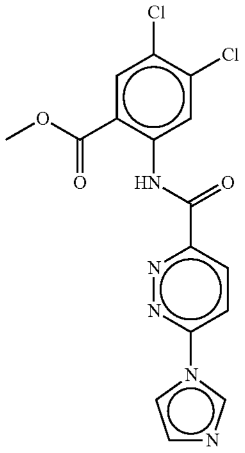
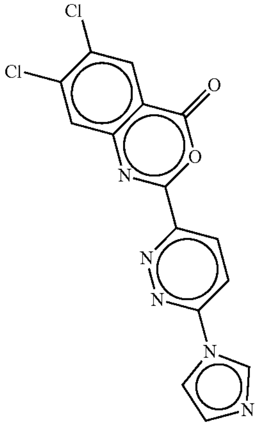
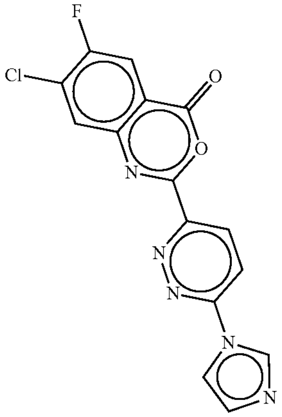
-continued
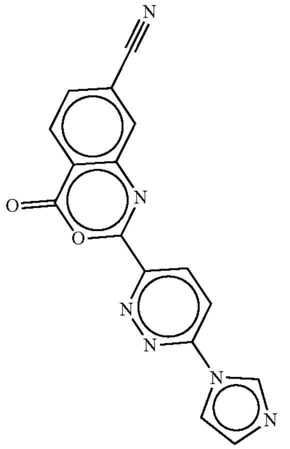
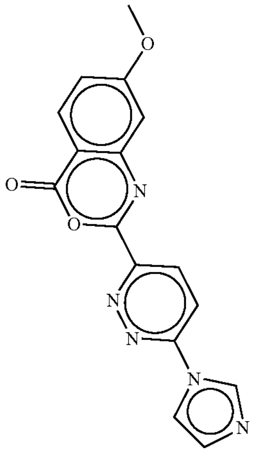
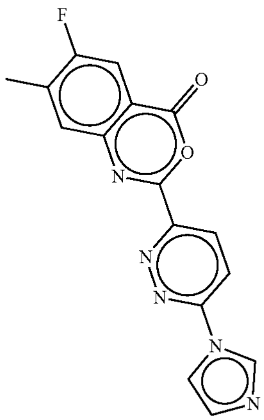
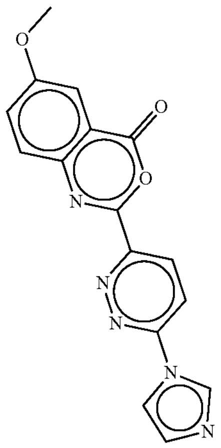
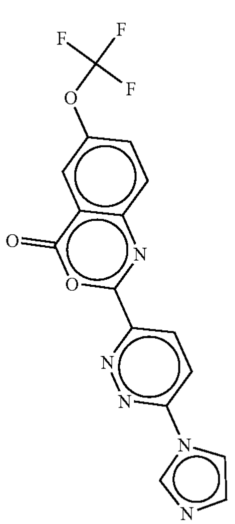
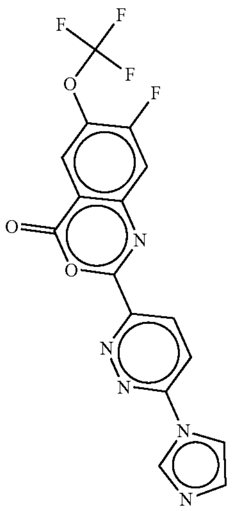

-continued
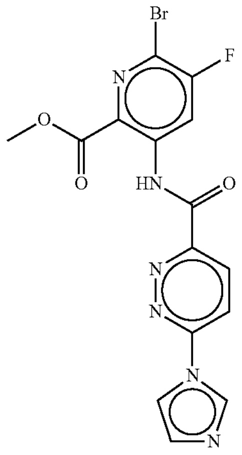
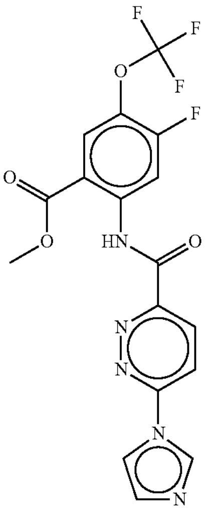
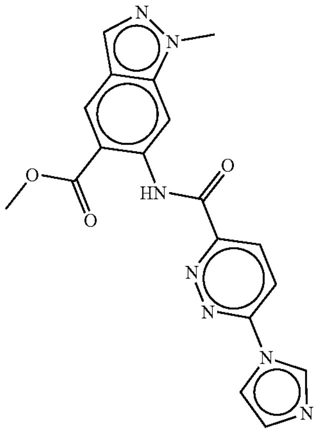
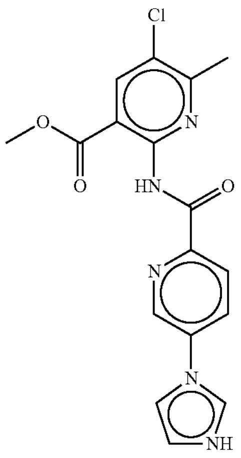
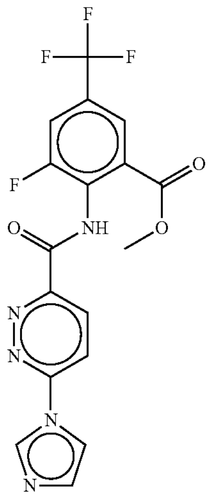
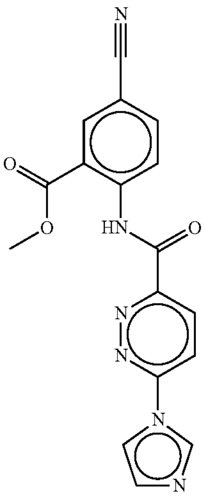
-continued
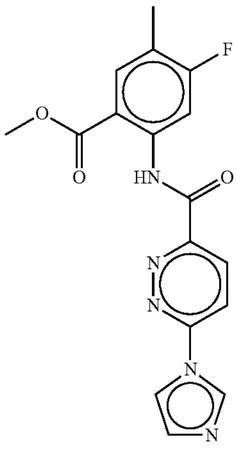
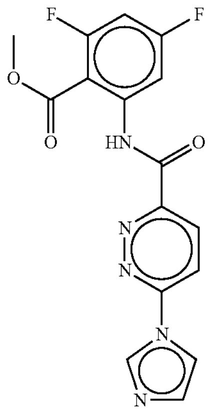
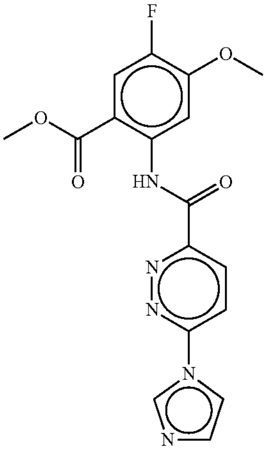
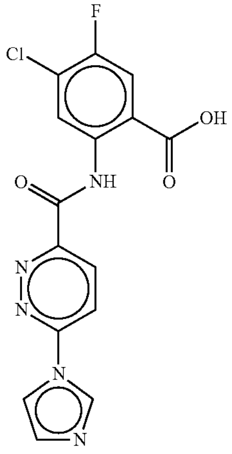
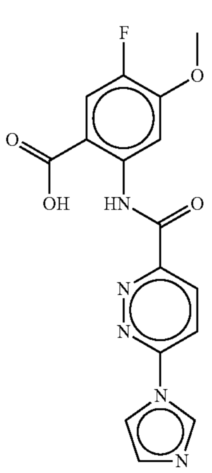
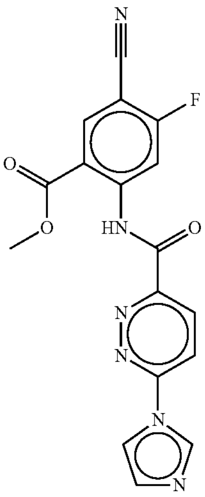

-continued
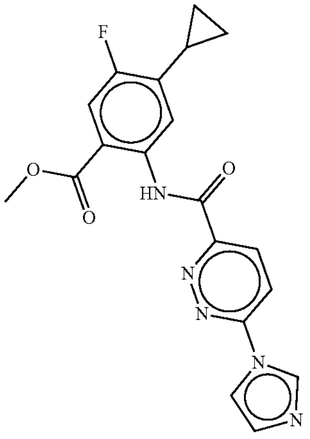
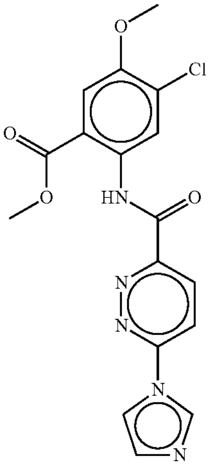
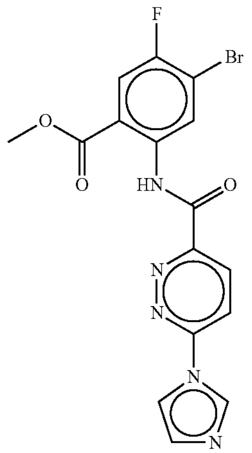
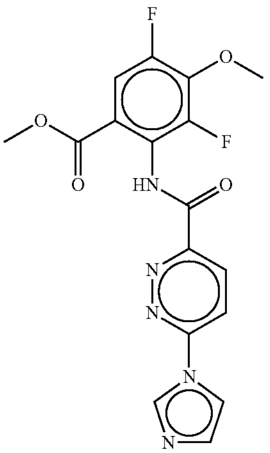
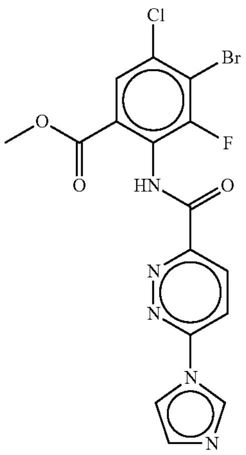
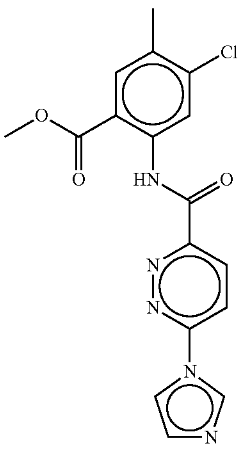
-continued
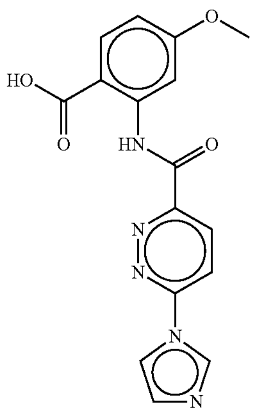
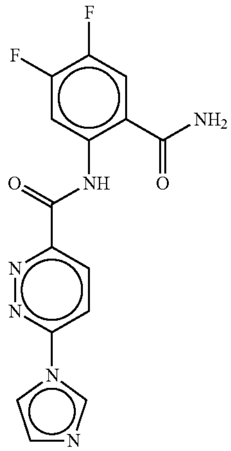
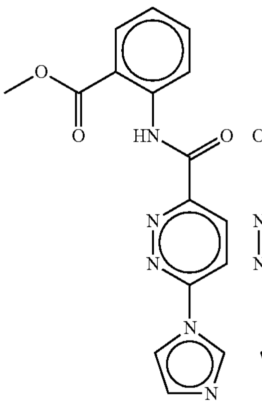
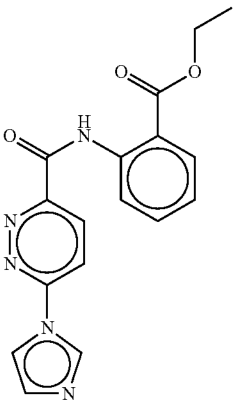
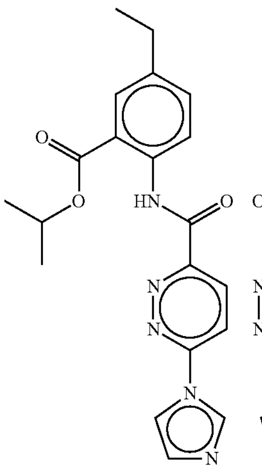
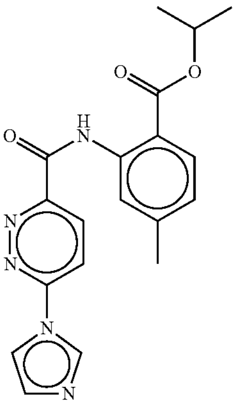

-continued
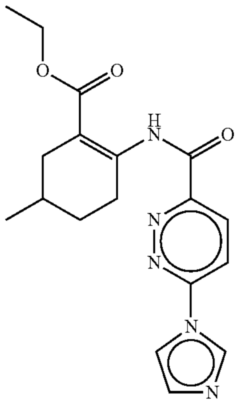
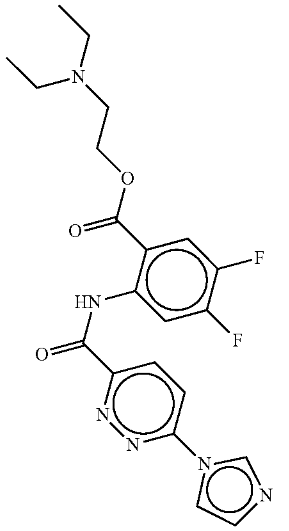
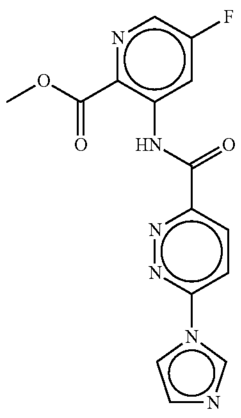
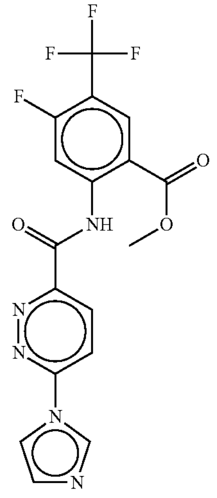
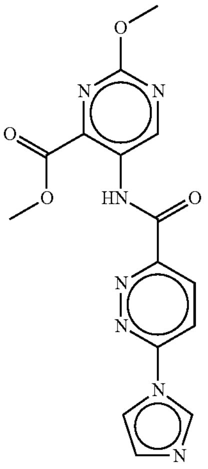
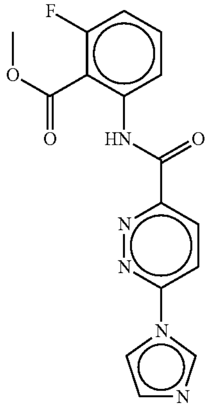
-continued
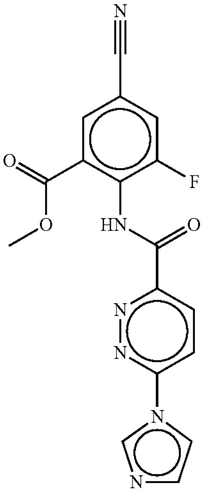
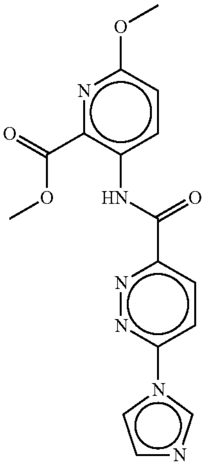
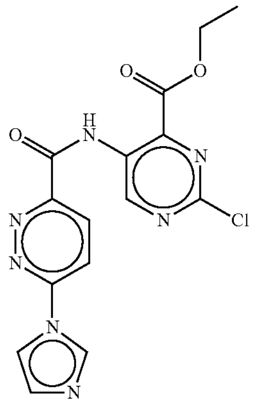
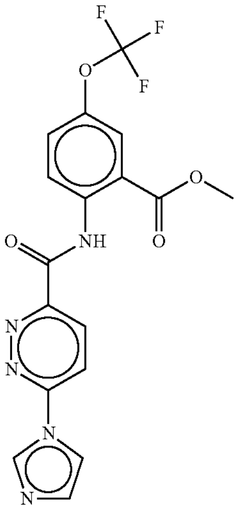
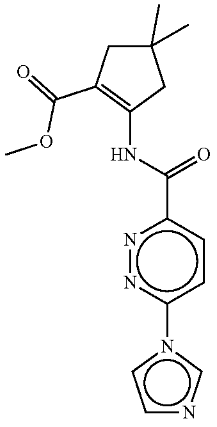
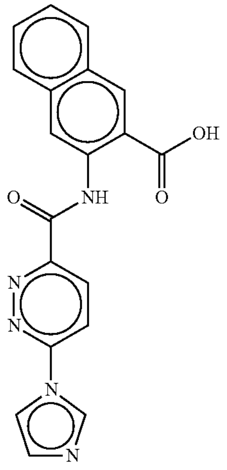

-continued
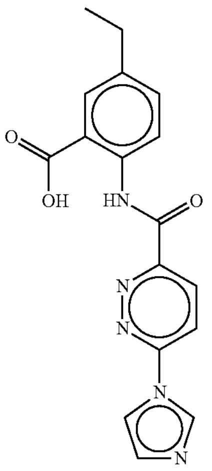
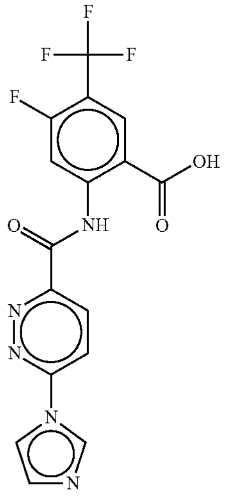
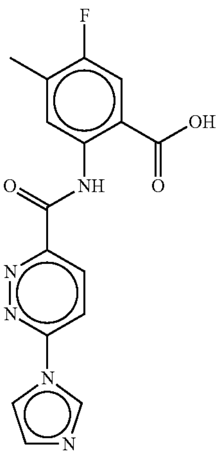
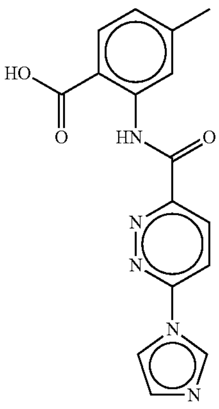
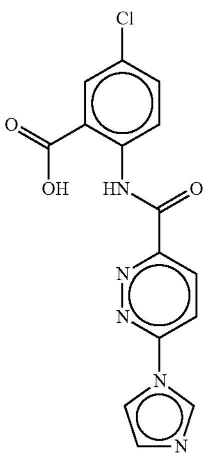
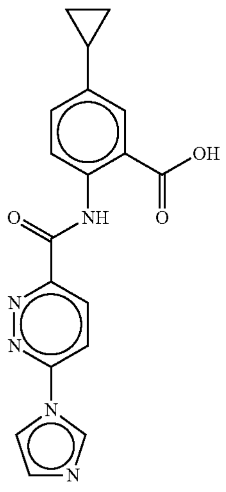
-continued
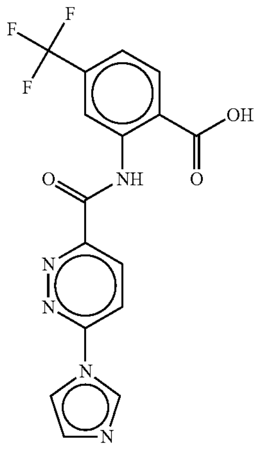
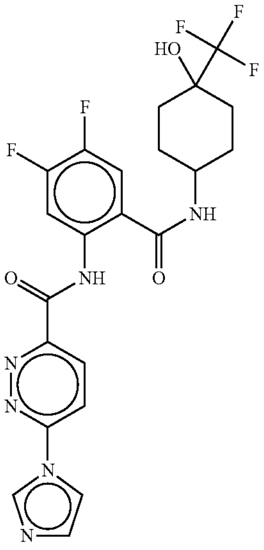
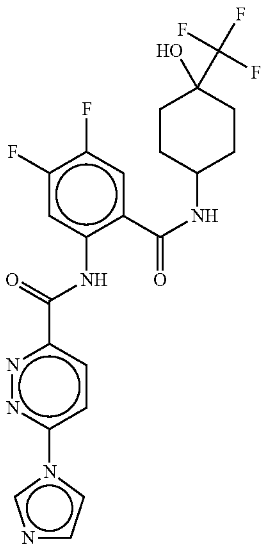
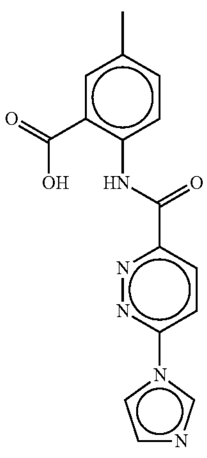
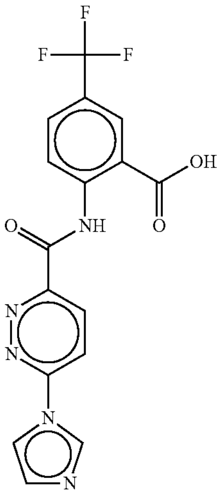
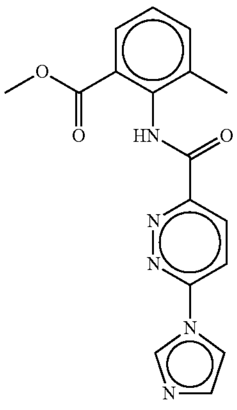

-continued
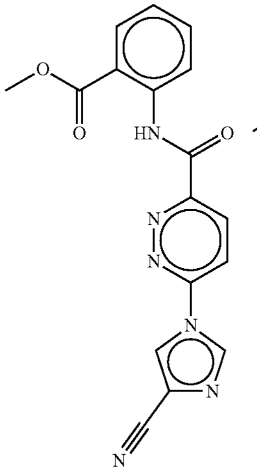
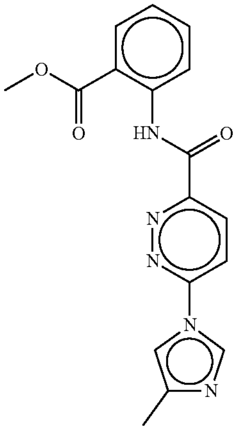
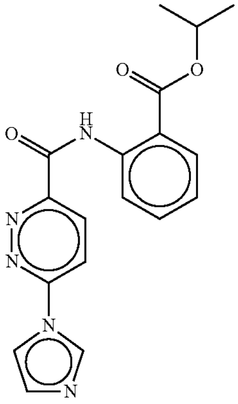
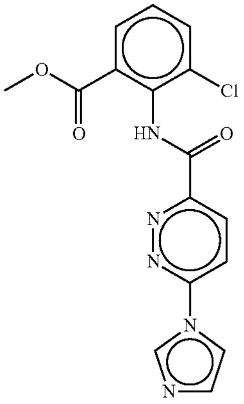
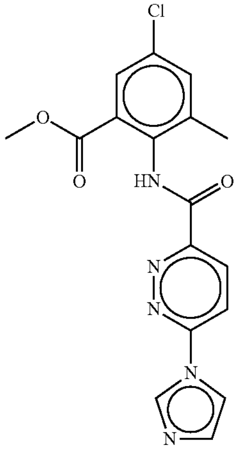
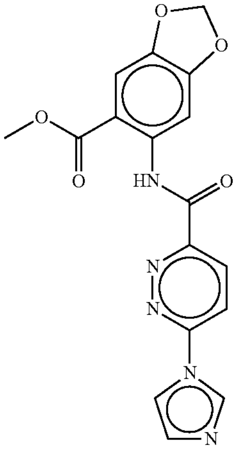
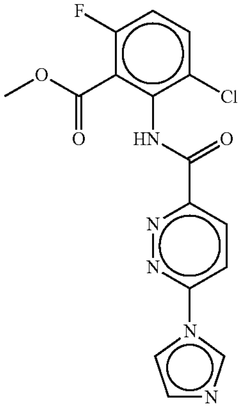
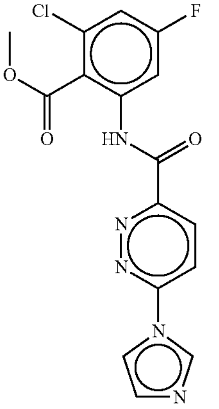
-continued
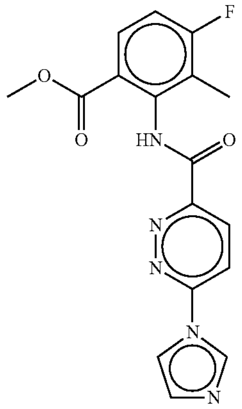
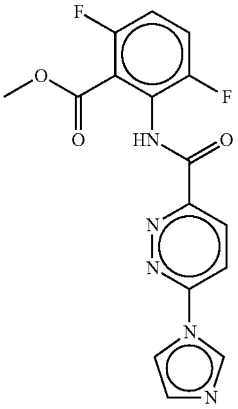
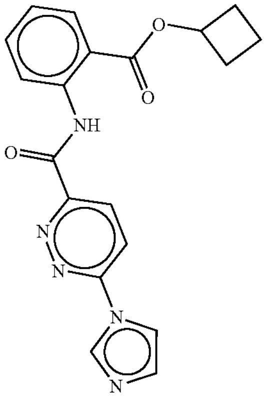
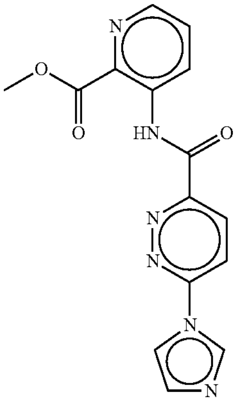
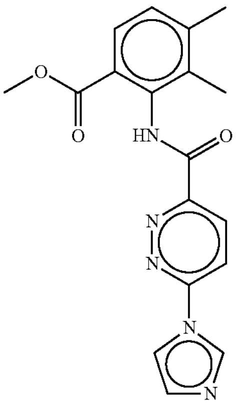
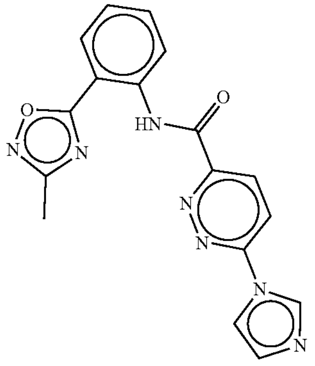
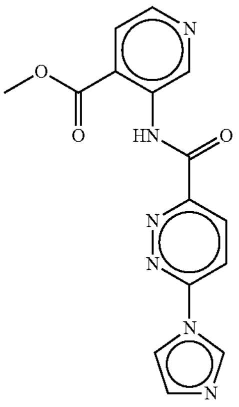
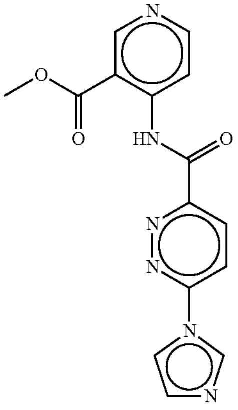

-continued
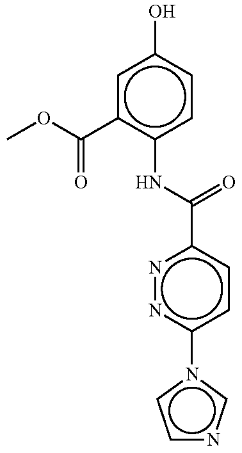
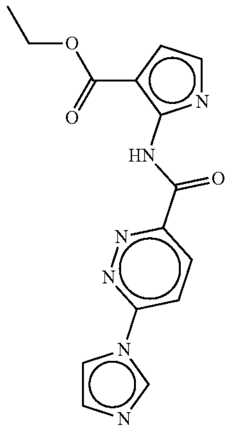
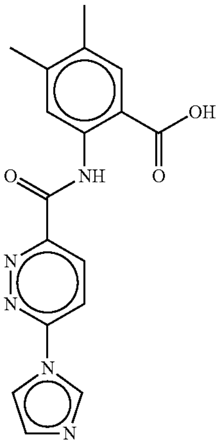
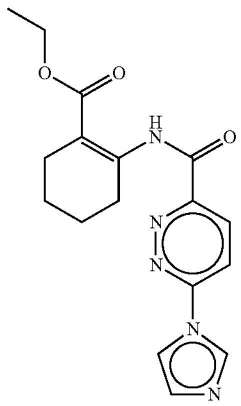
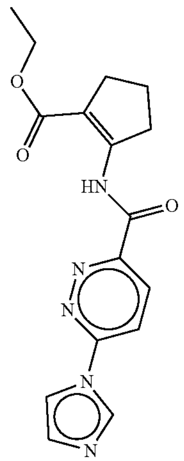
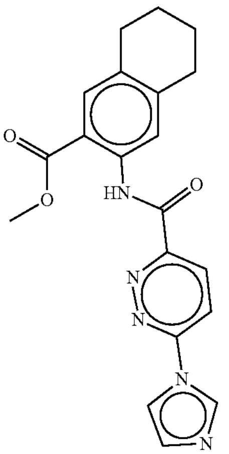
-continued
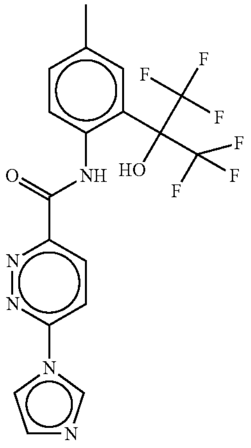
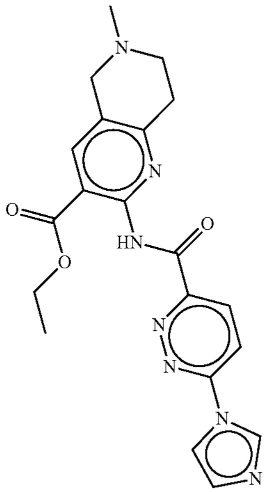
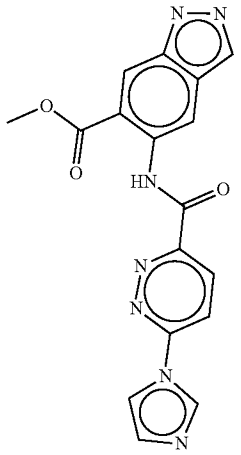
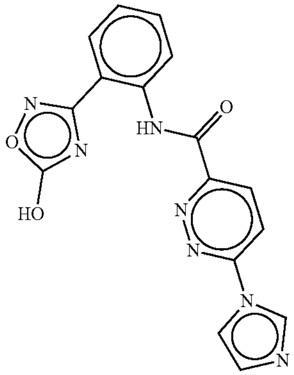
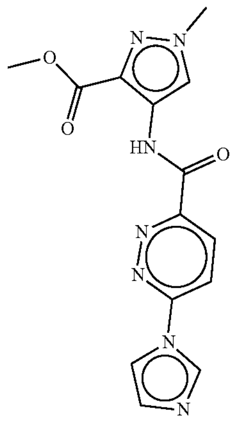
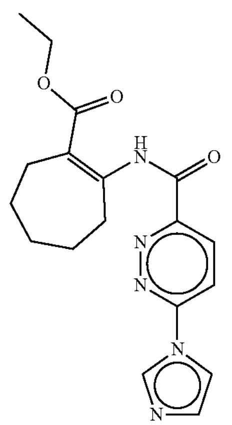

-continued
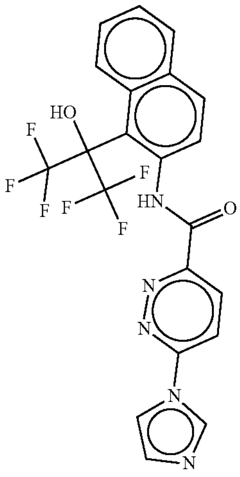
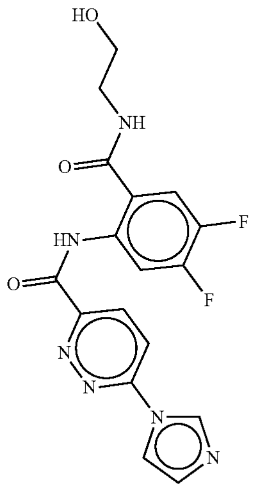
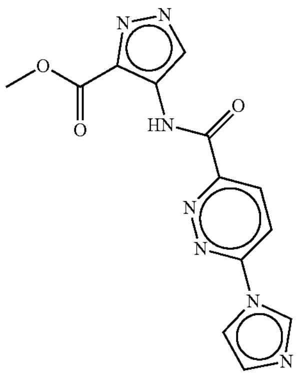
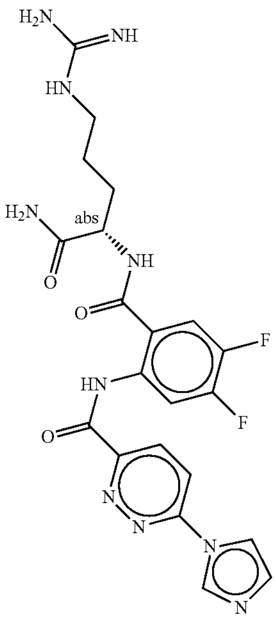
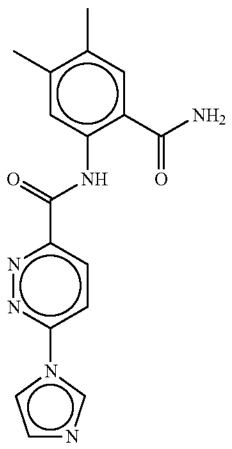
-continued
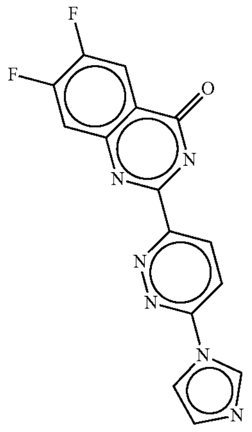
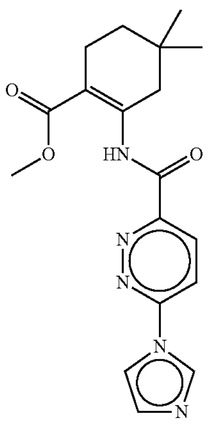
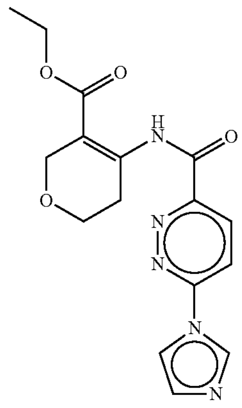
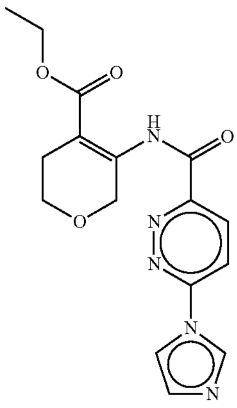
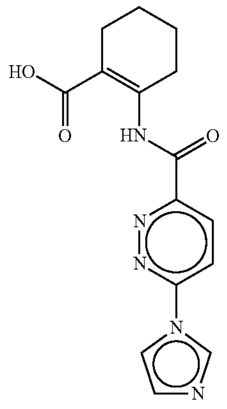
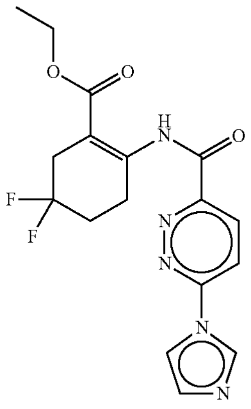
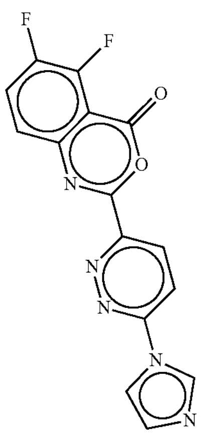
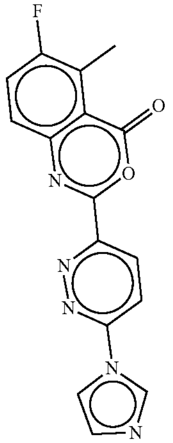

-continued
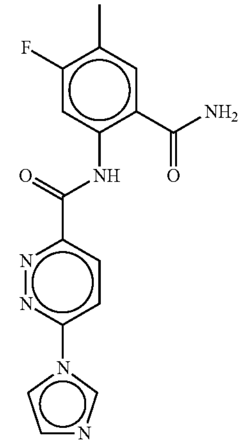
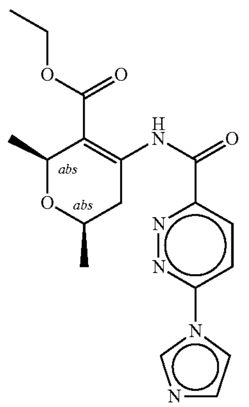
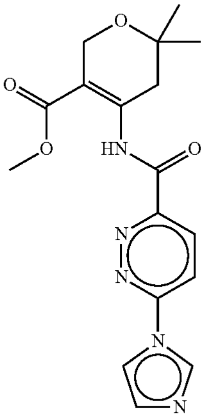
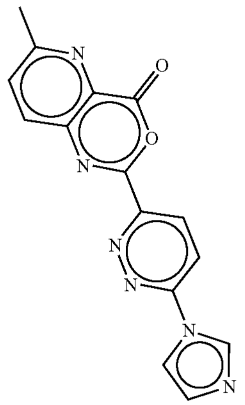
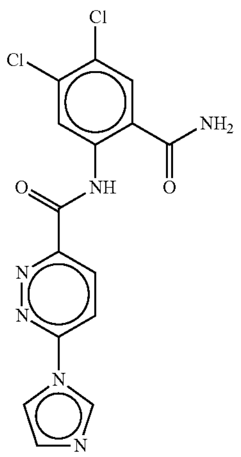
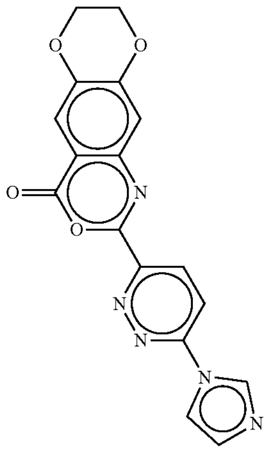
-continued
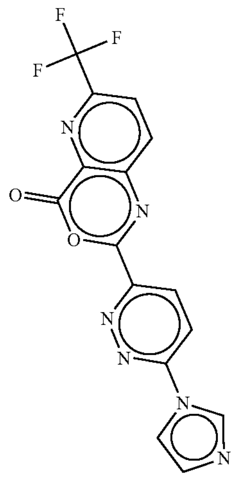
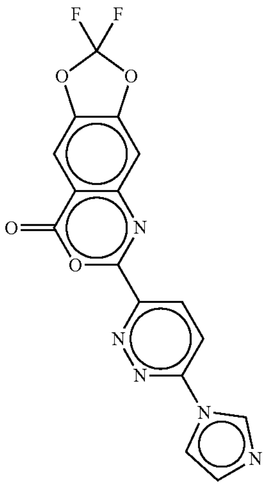
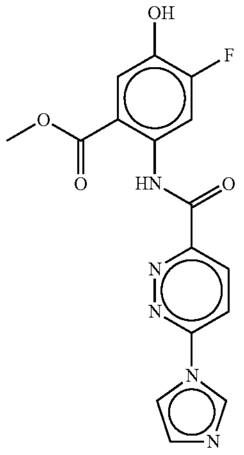
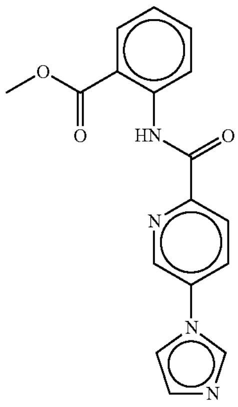
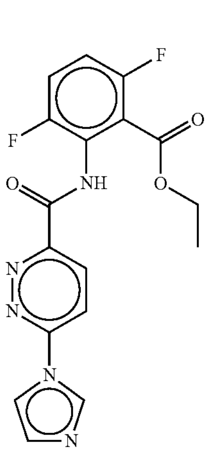
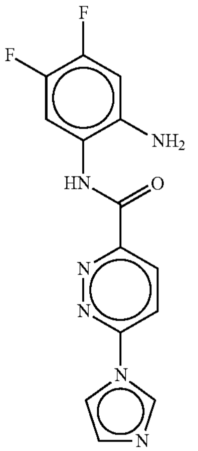

-continued
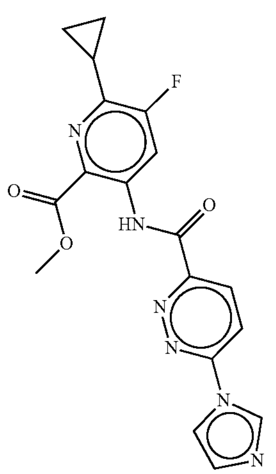
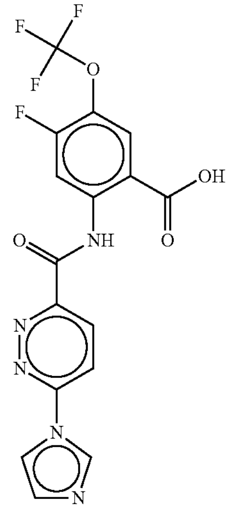
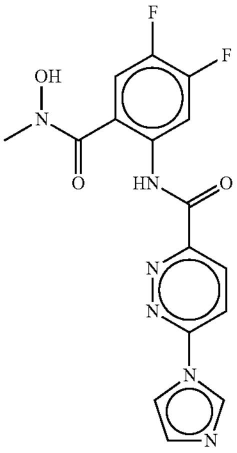
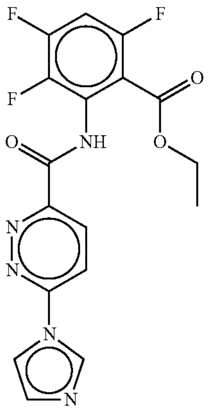
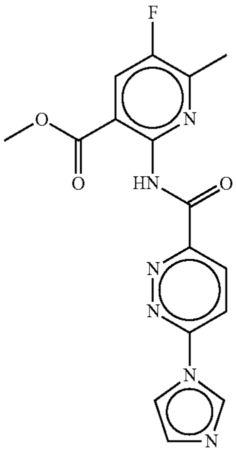
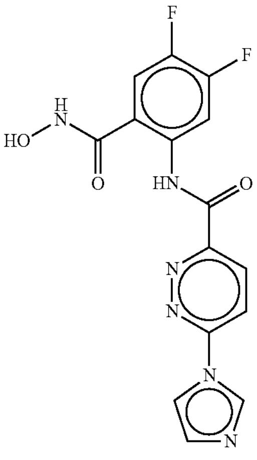
-continued
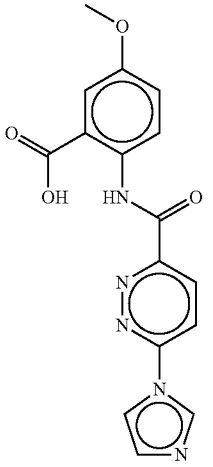
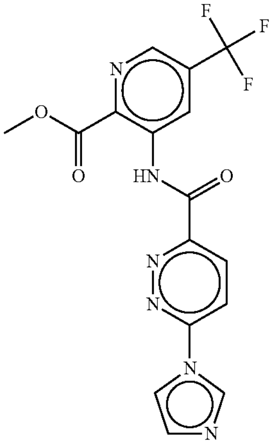
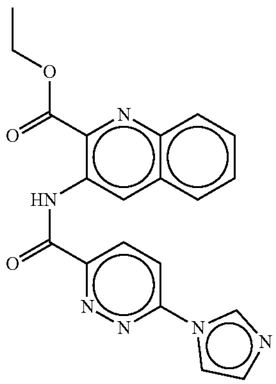
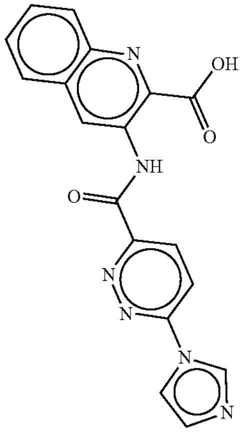
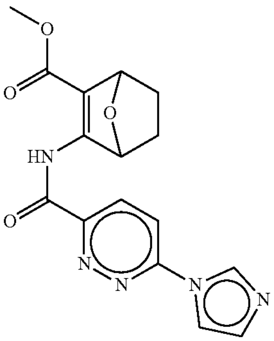
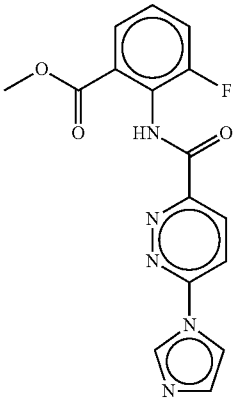

-continued
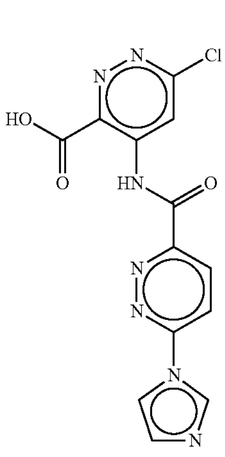
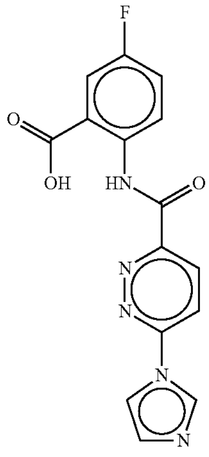
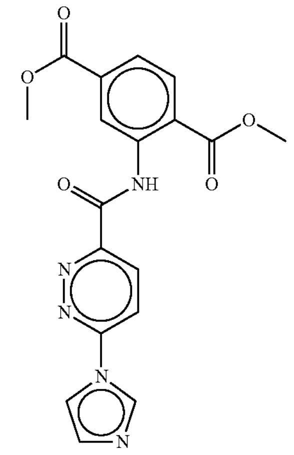
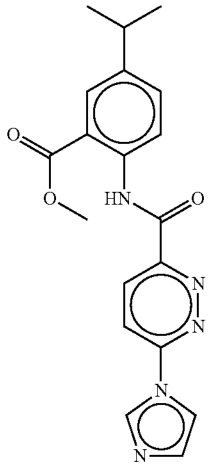
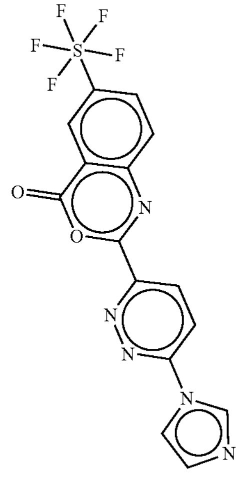
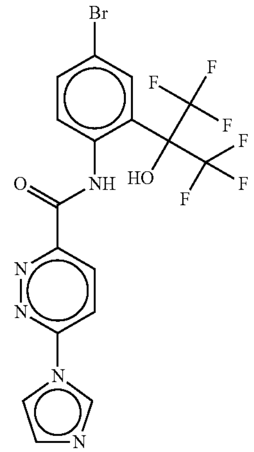
-continued
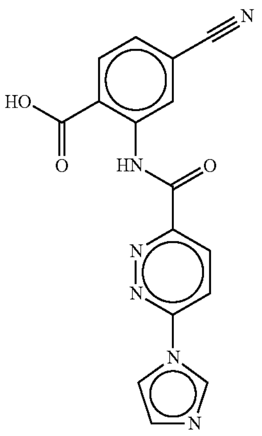
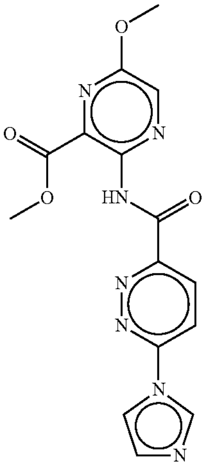
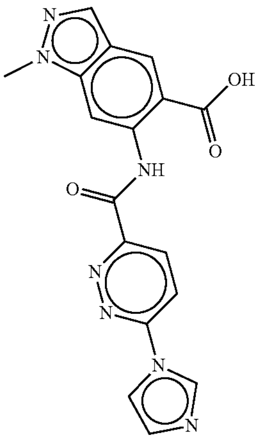
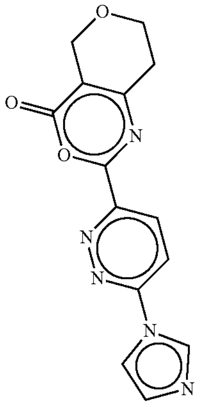
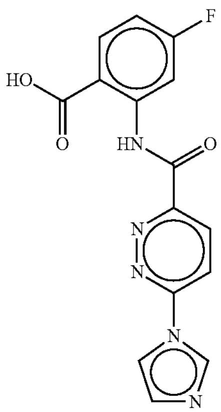
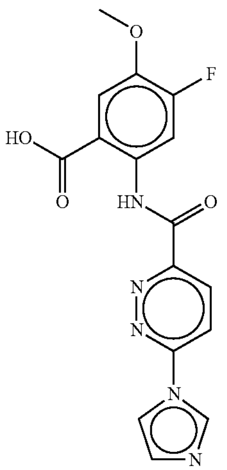

-continued
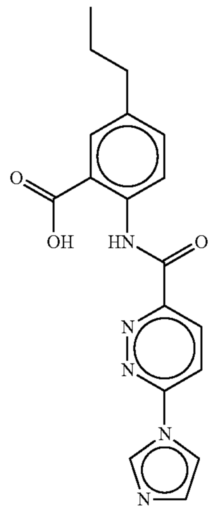
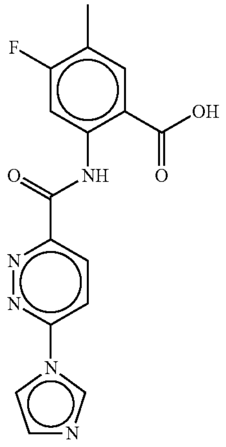
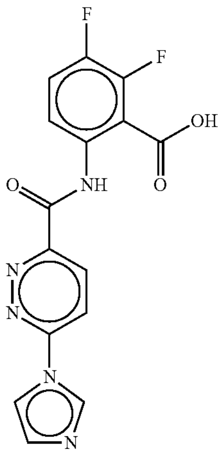
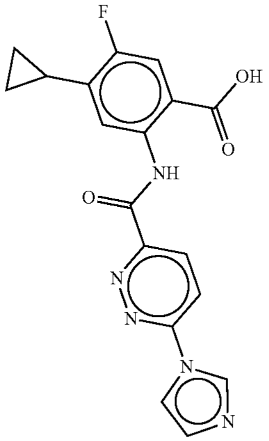
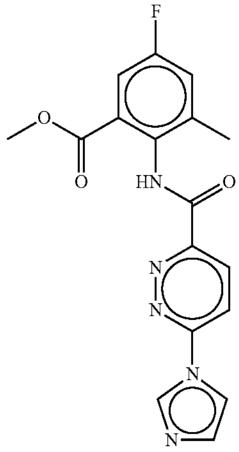
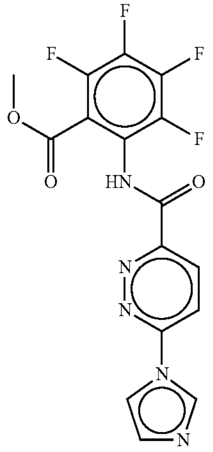
-continued
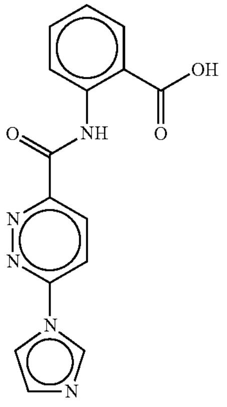
or a pharmaceutically acceptable salt thereof.
14. A compound of any one of the following formulae:
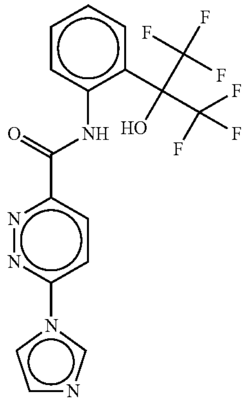
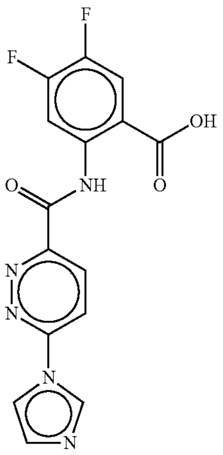
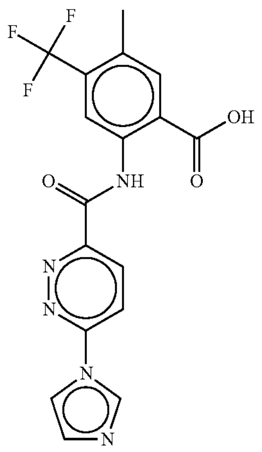
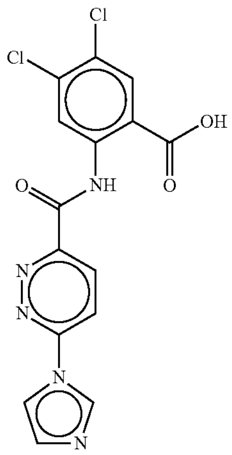

-continued
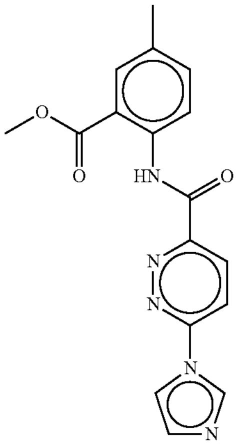
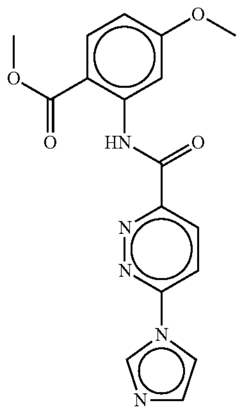
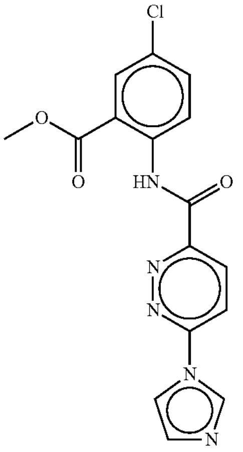
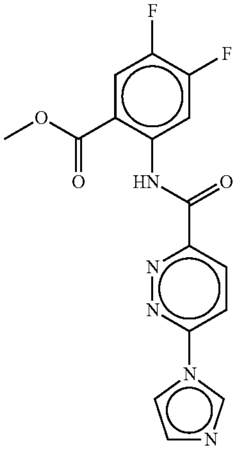
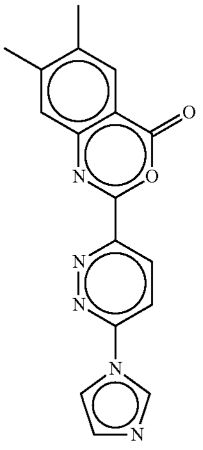
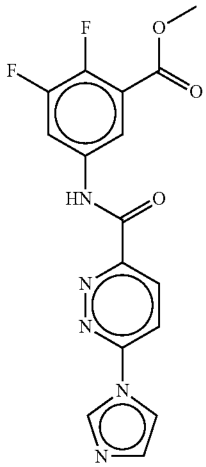
-continued
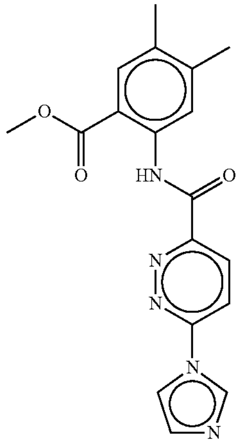
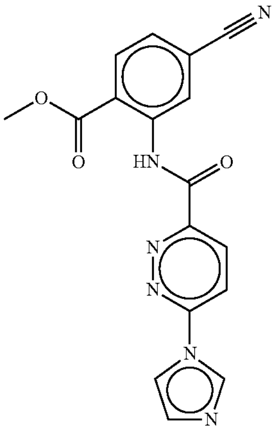
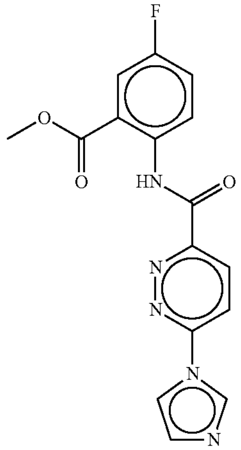
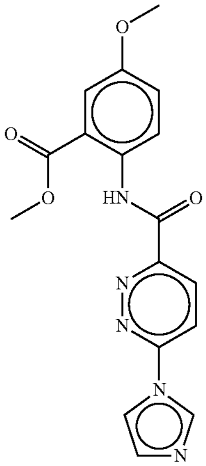
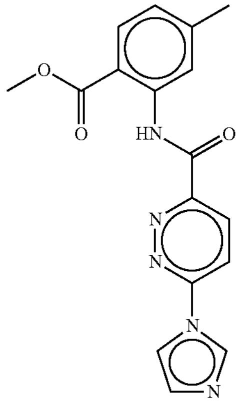
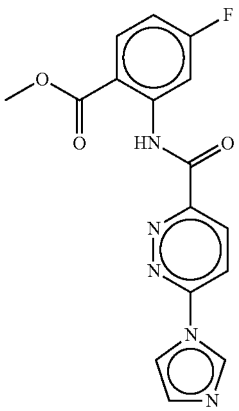
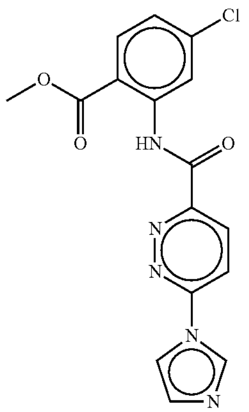
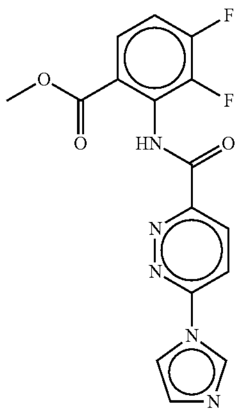

-continued
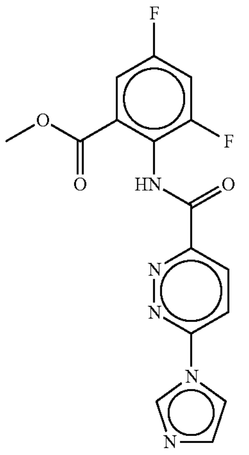
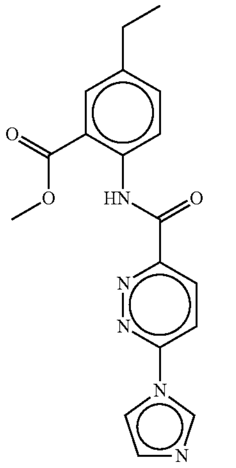
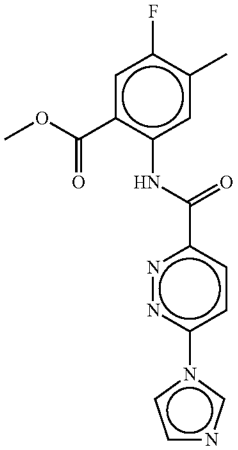
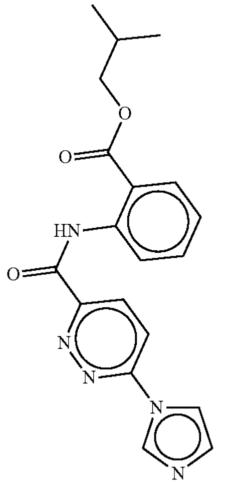
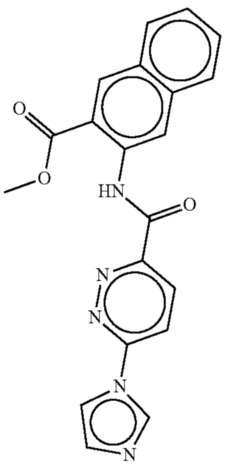
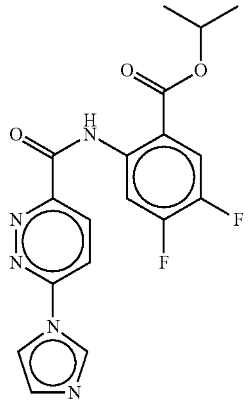
-continued
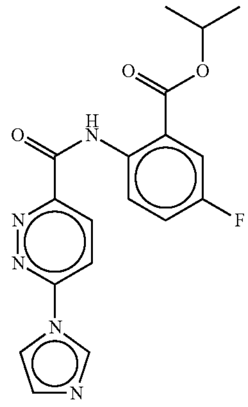
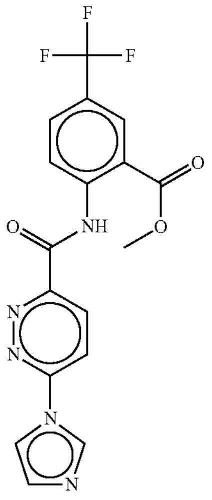
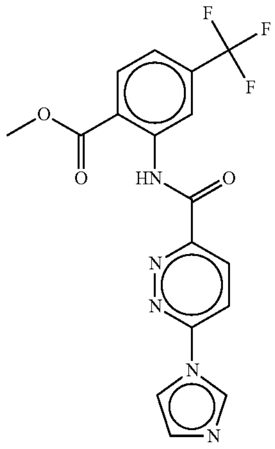
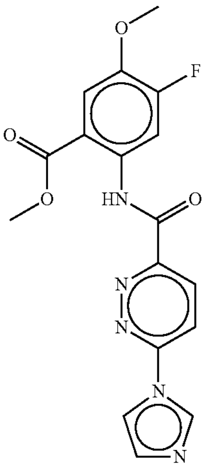
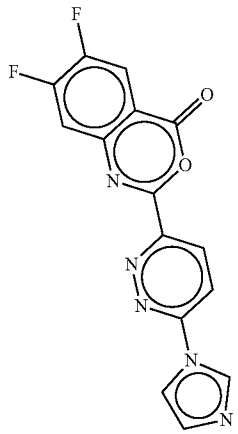
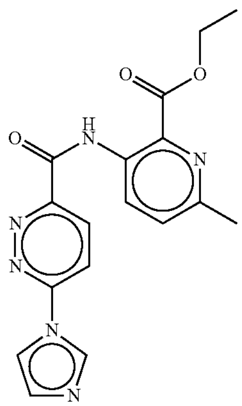

-continued
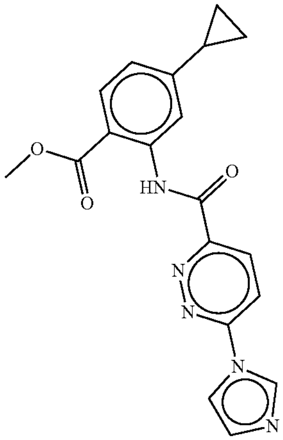
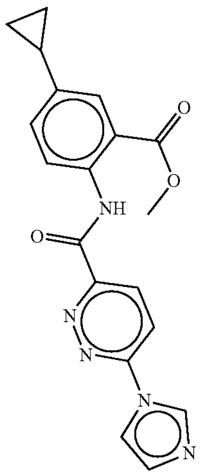
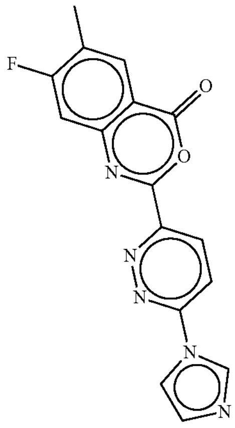
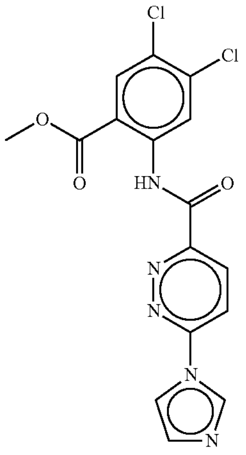
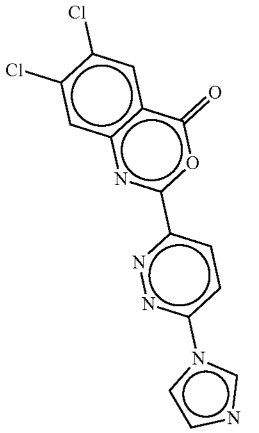
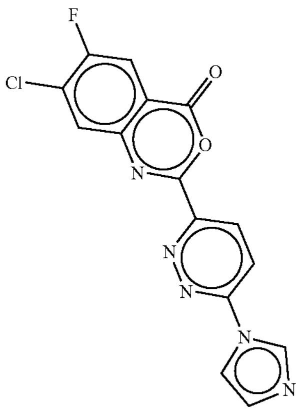
-continued
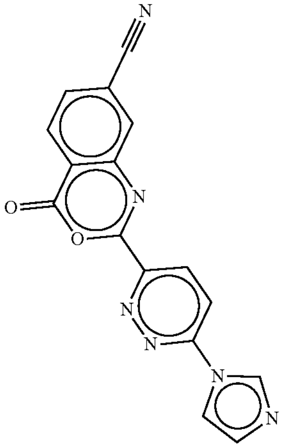
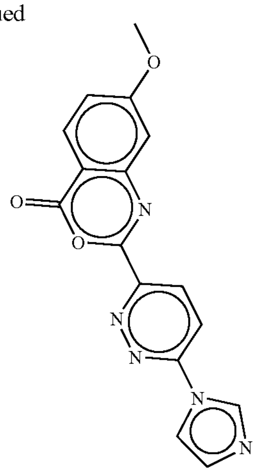
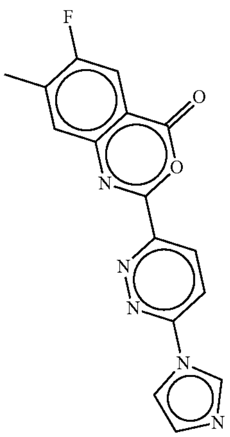
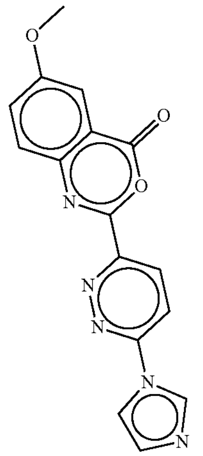
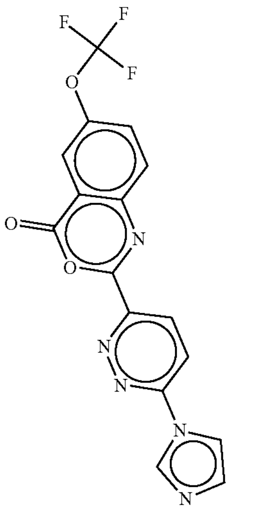
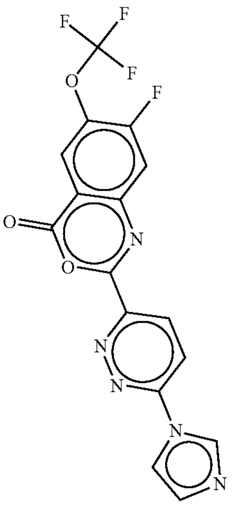

-continued
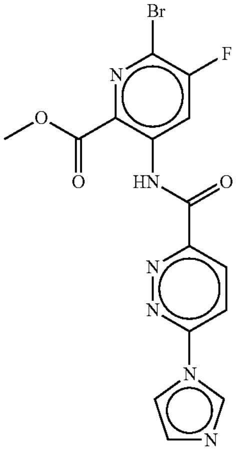
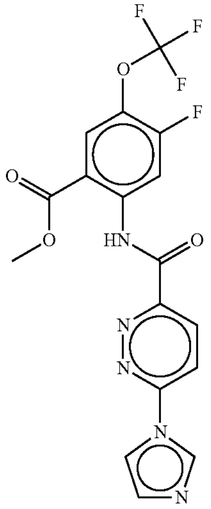
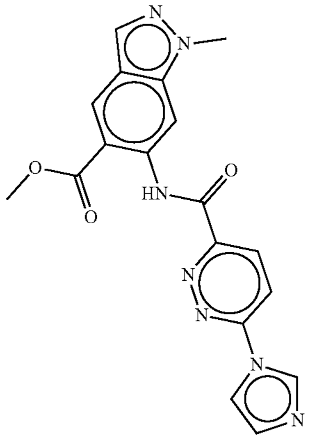
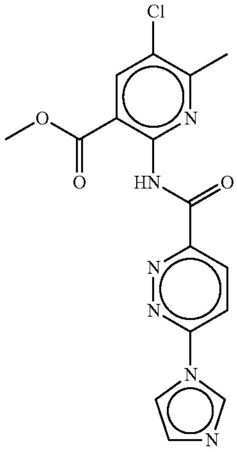
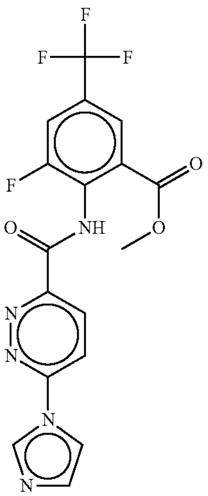
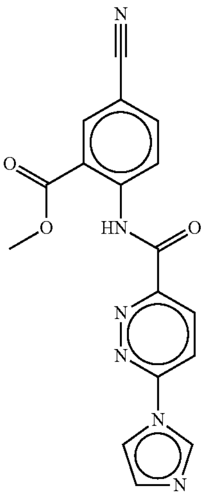
-continued
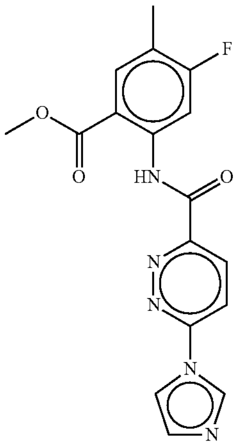
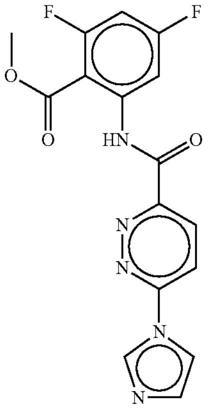
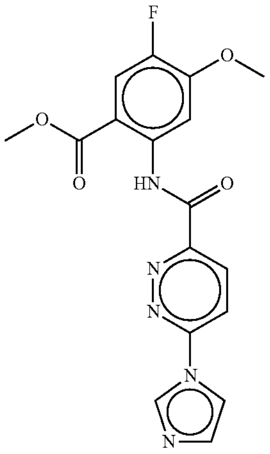
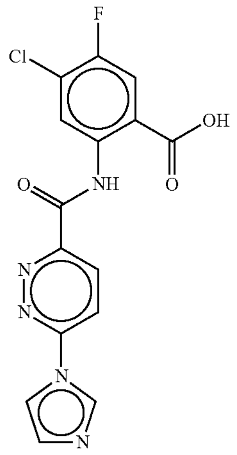
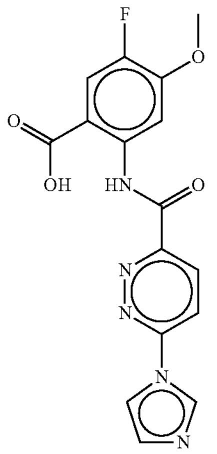
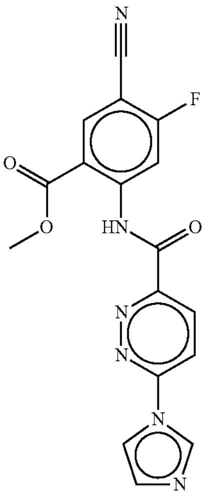

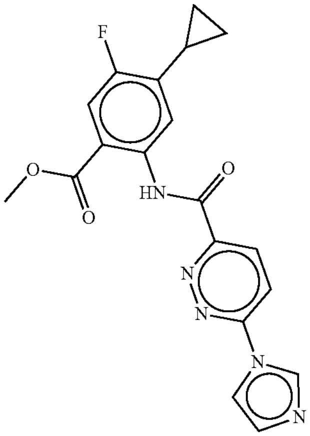
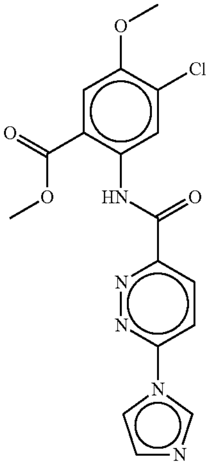
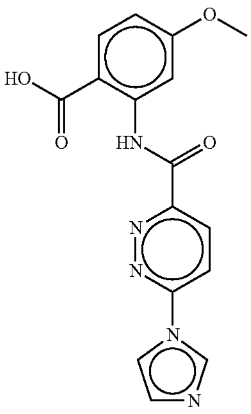
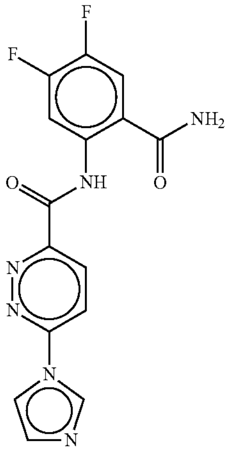
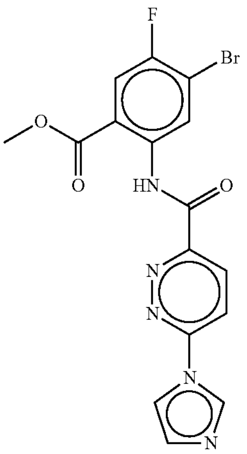
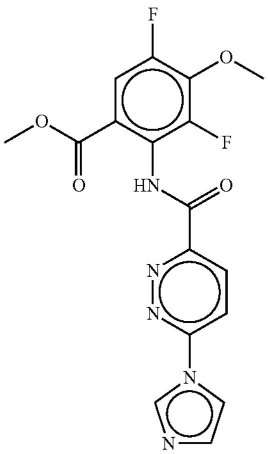
-continued
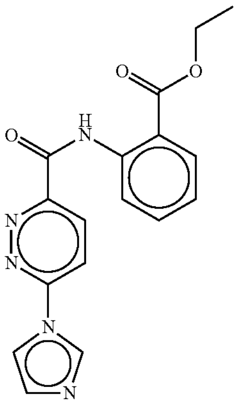
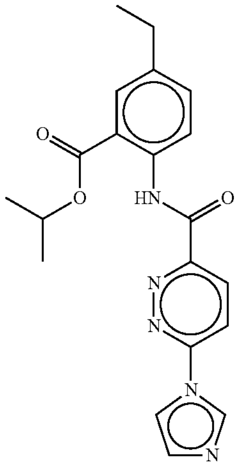
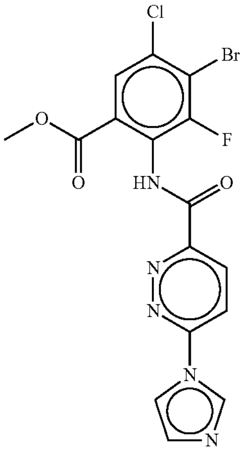
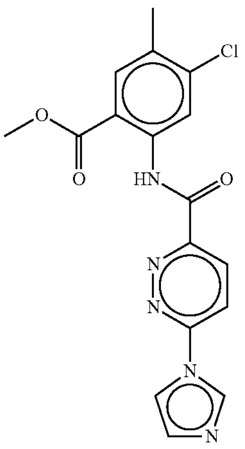
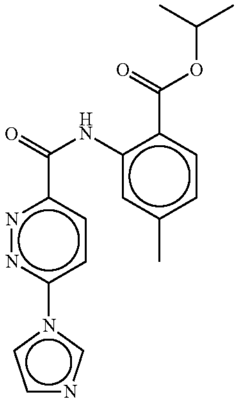
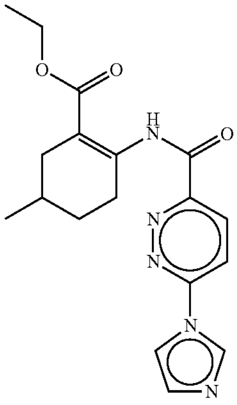

-continued
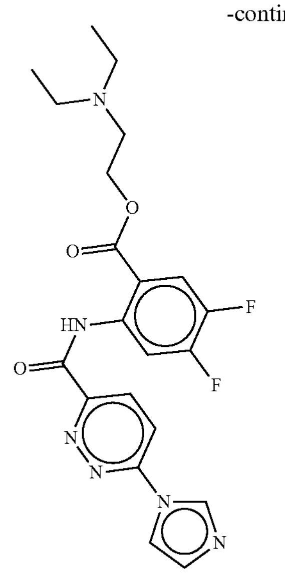
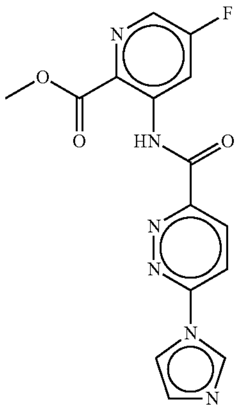
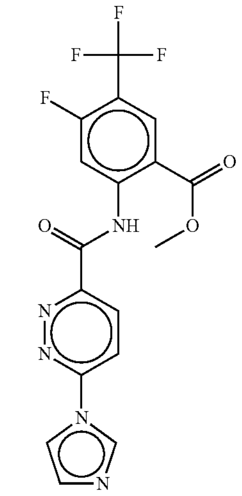
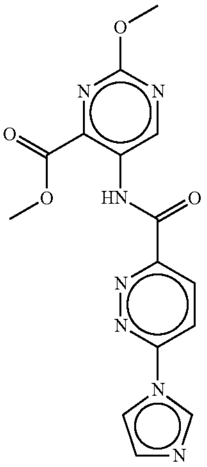
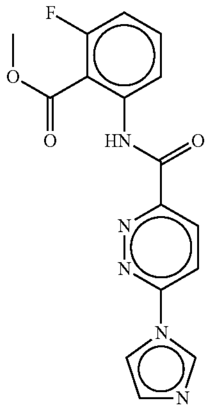
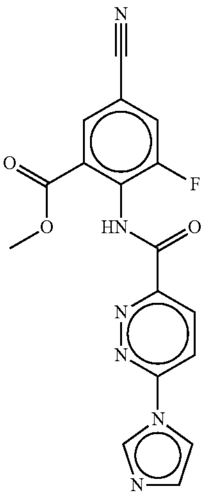
-continued
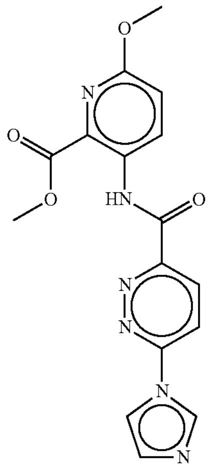
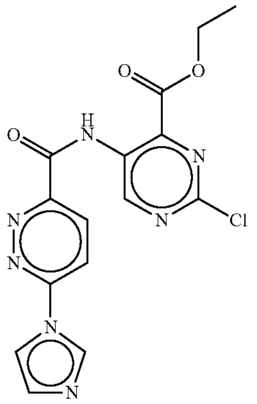
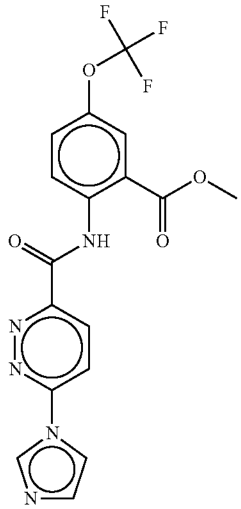
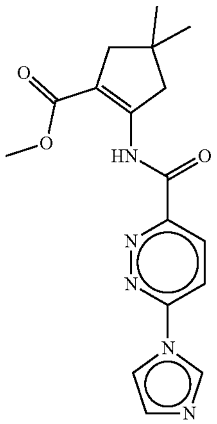
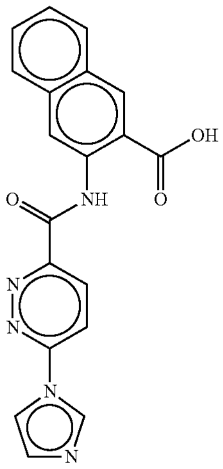
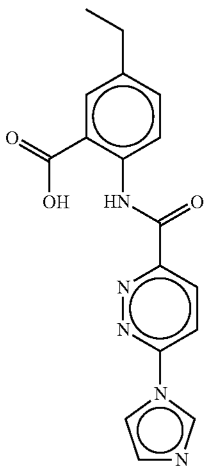

-continued
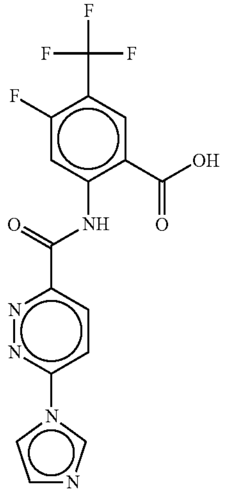
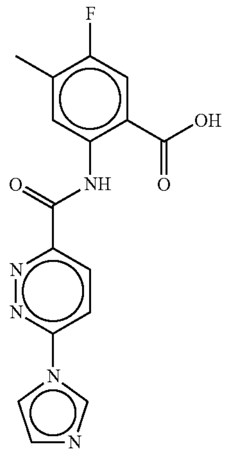
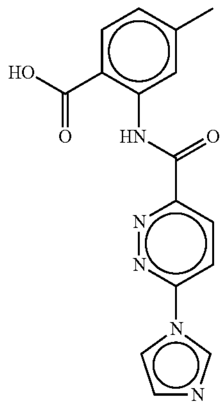
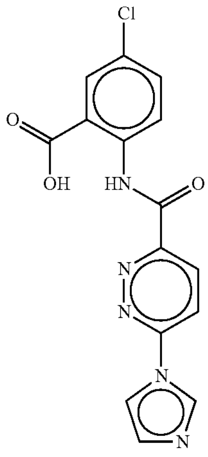
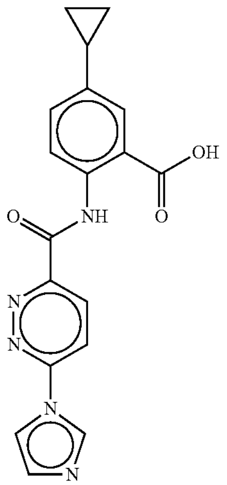
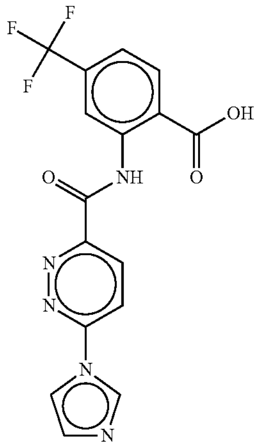
-continued
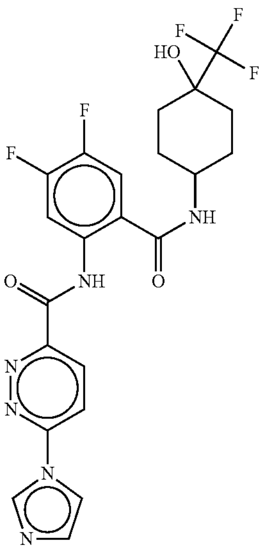
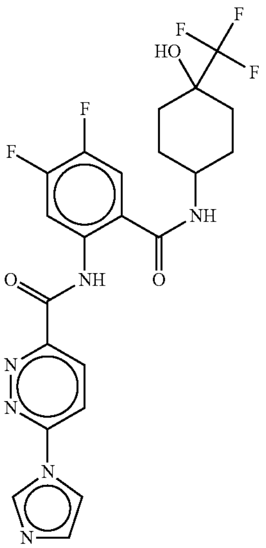
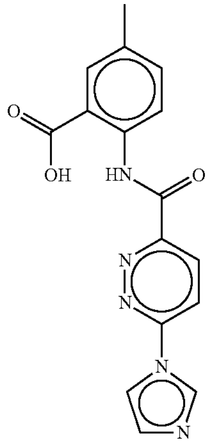
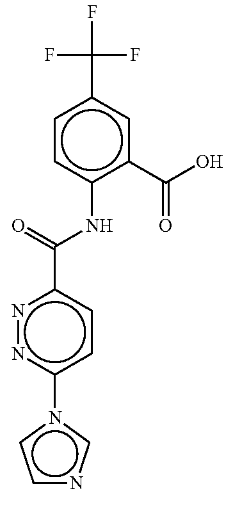
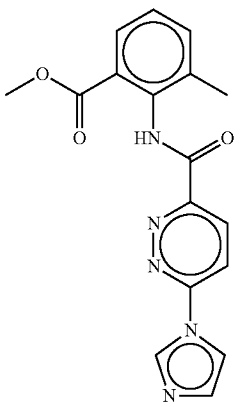
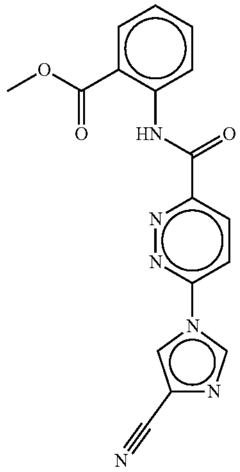

-continued
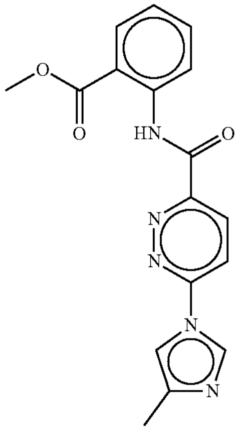
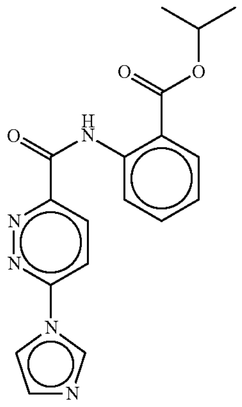
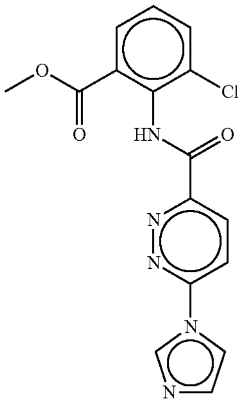
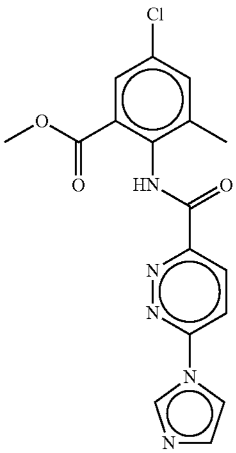
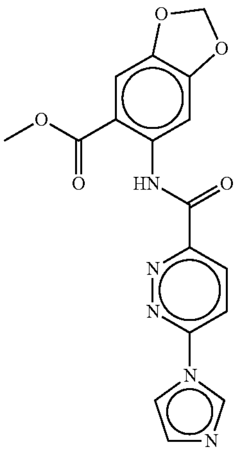
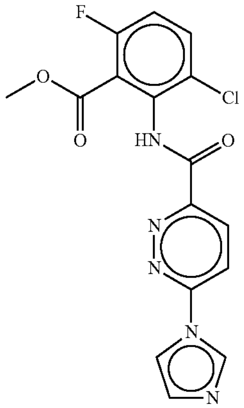
-continued
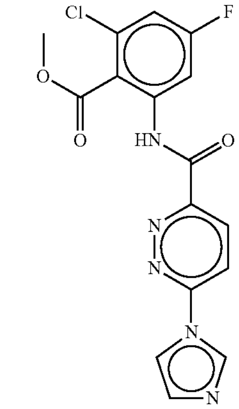
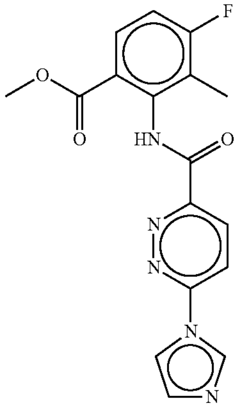
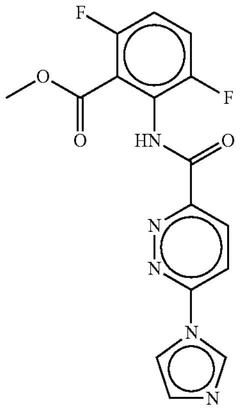
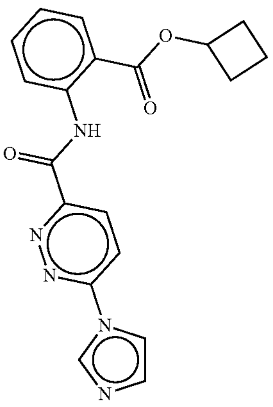
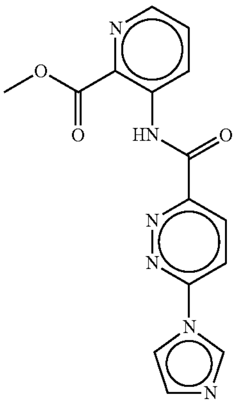
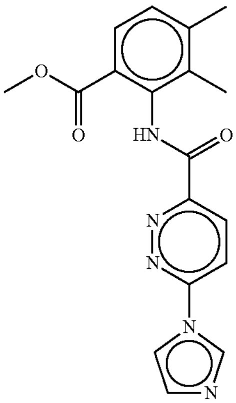
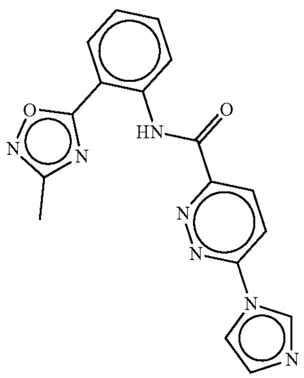
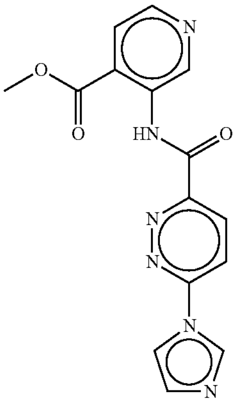

-continued
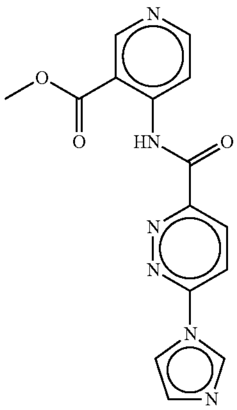
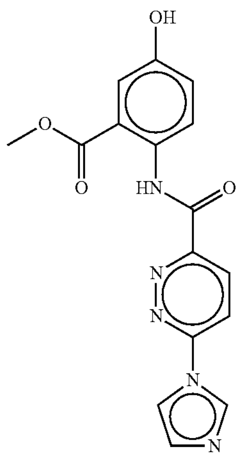
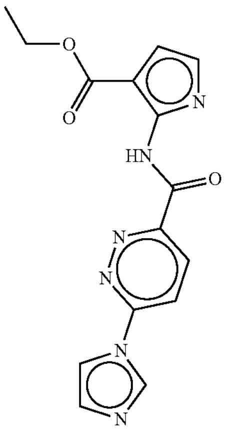
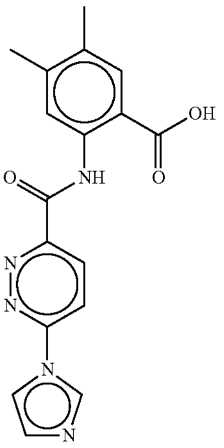
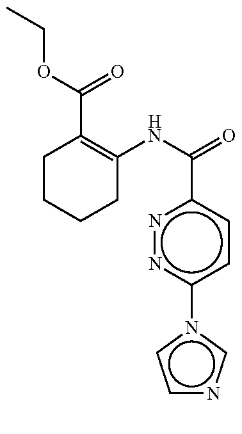
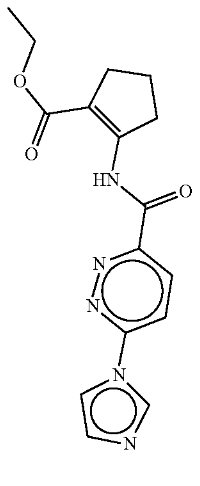
-continued
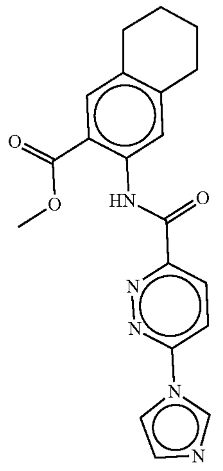
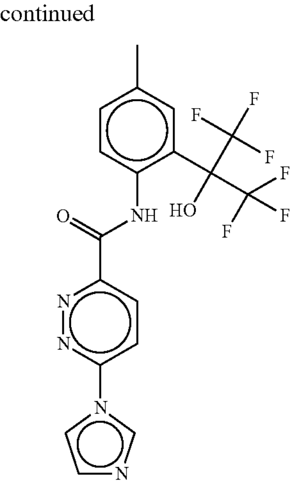
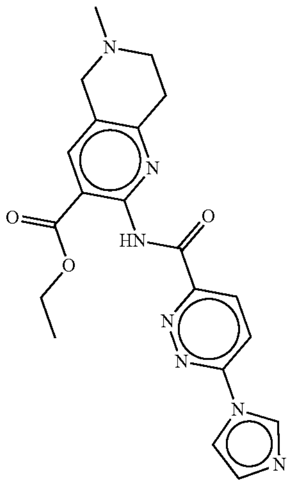
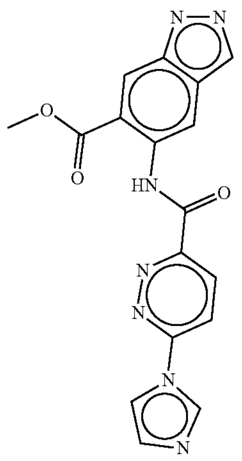
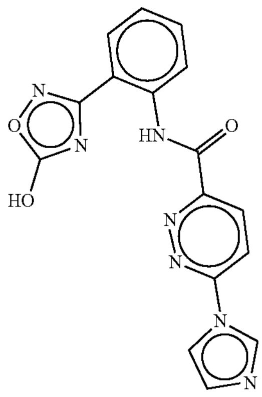
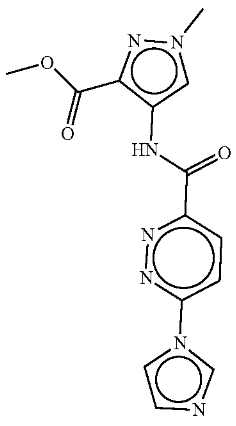

-continued
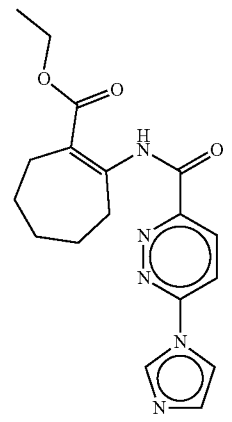
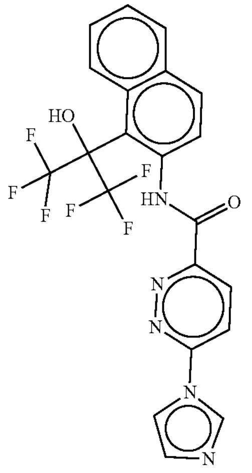
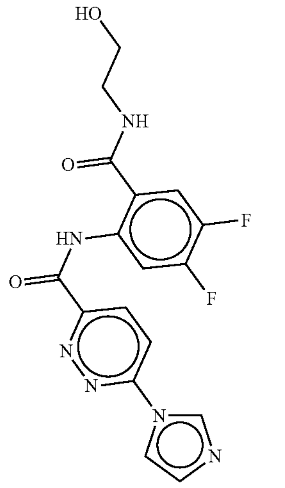
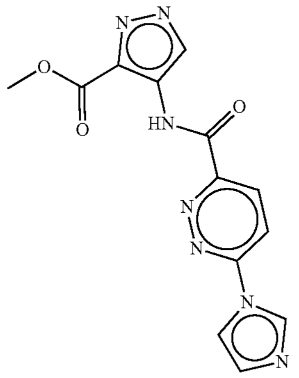
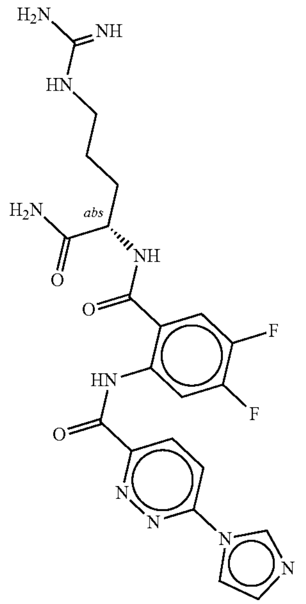
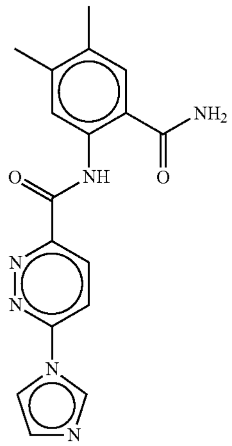
-continued
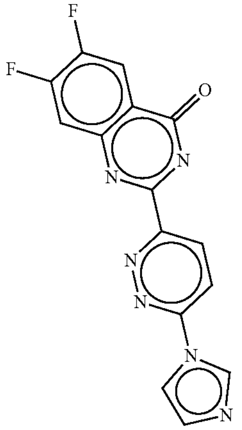
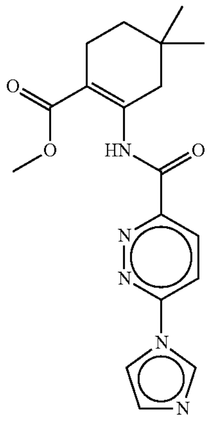
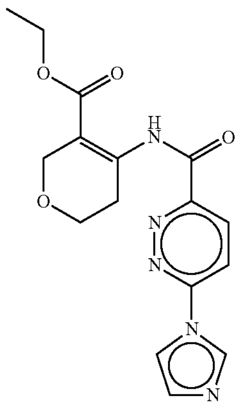
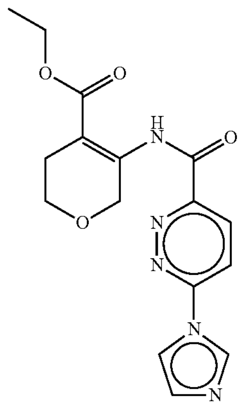
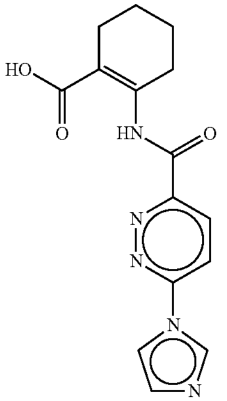
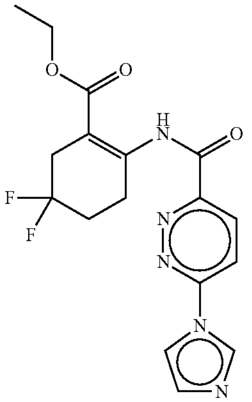

-continued
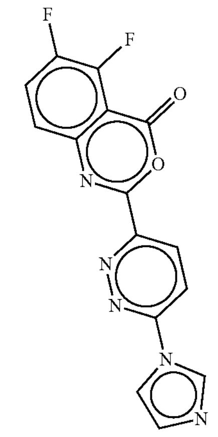
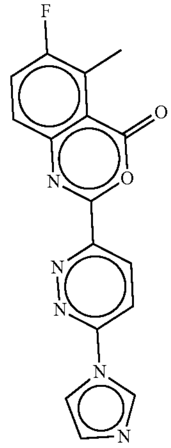
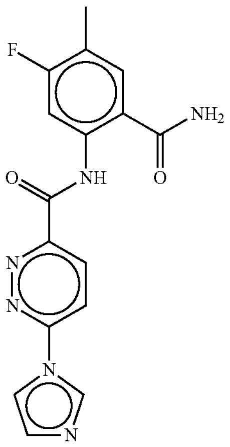
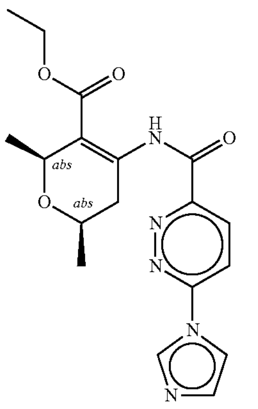
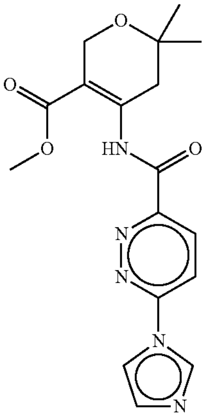
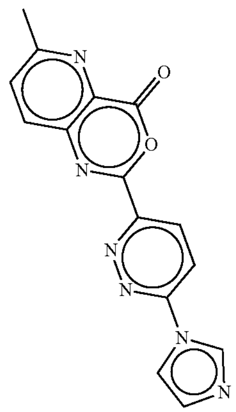
-continued
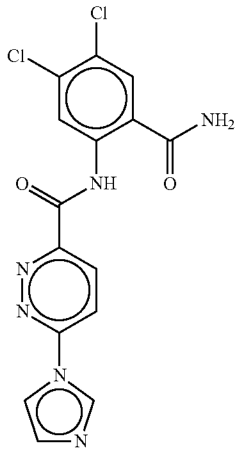
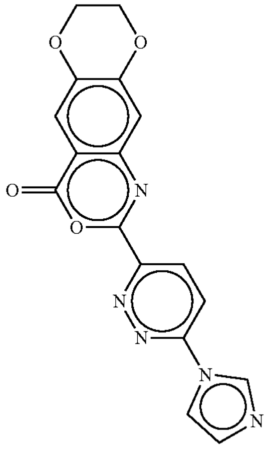
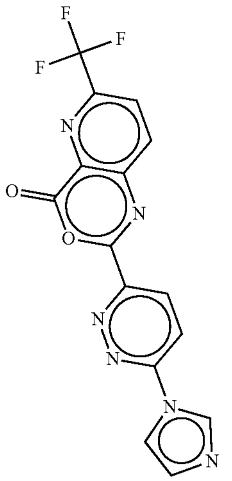
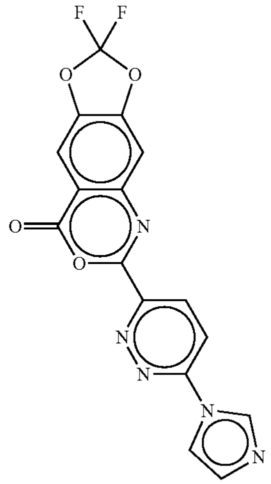
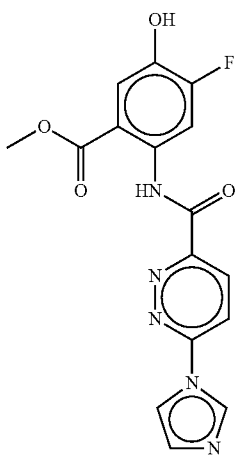
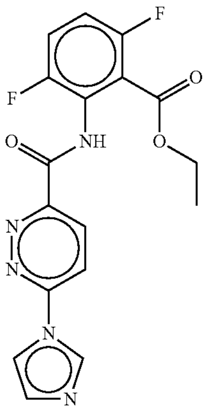

-continued
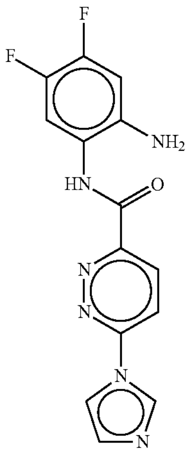
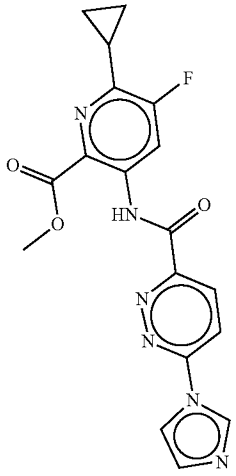
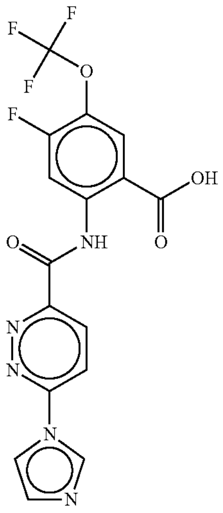
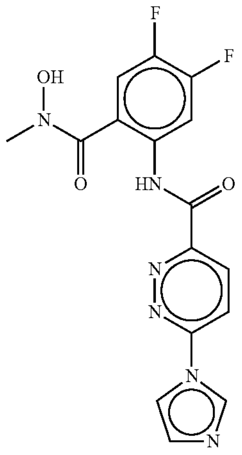
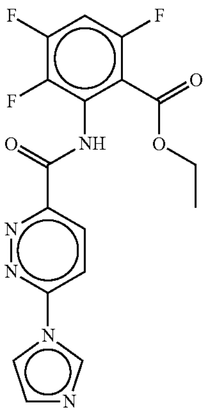
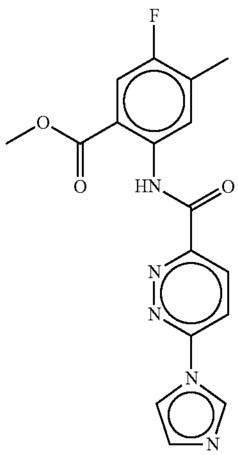
-continued
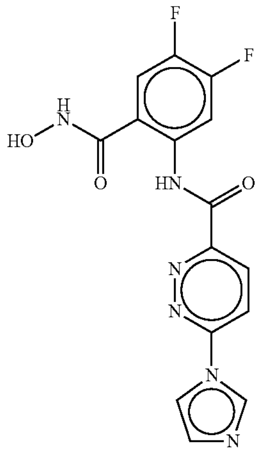
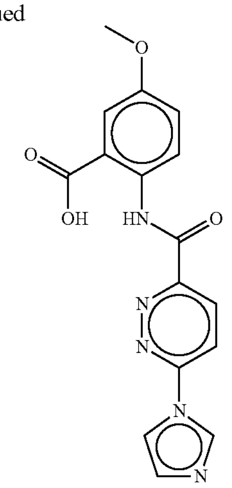
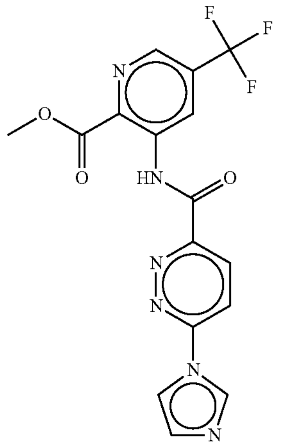
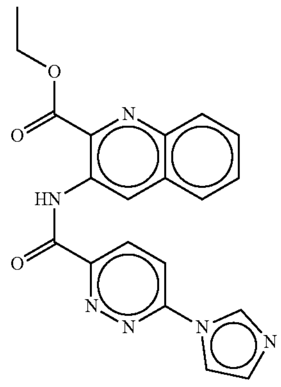
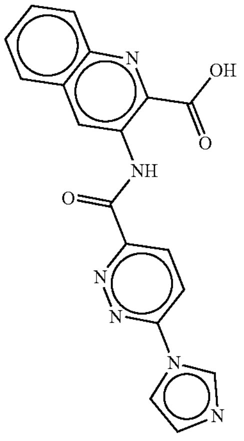
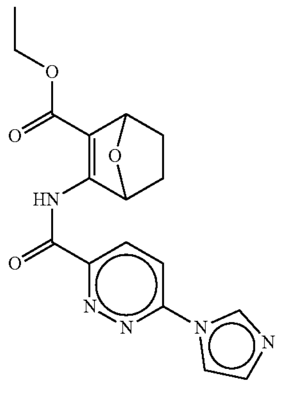

-continued
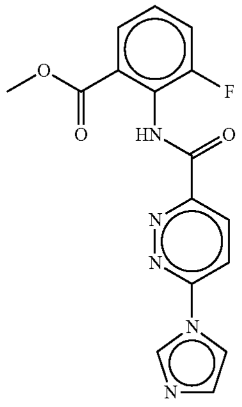
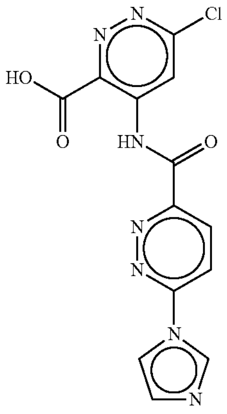
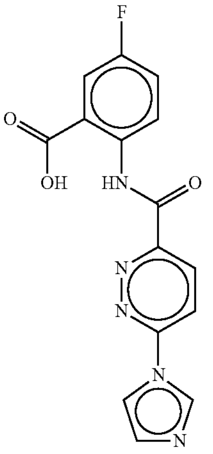
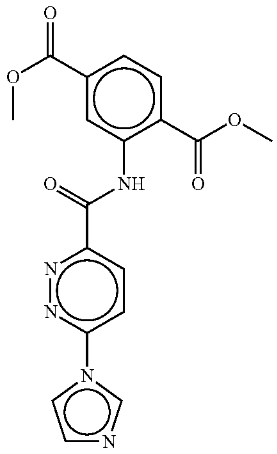
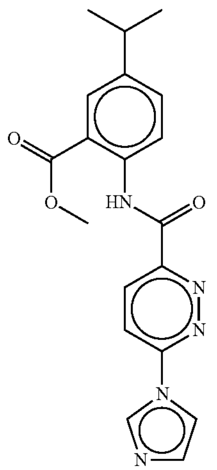
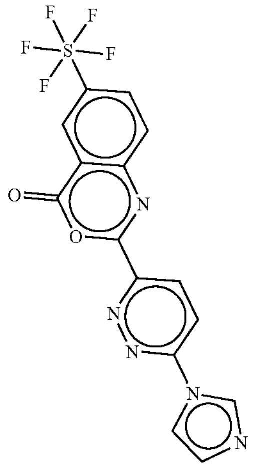
-continued
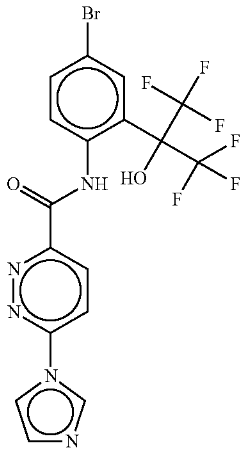
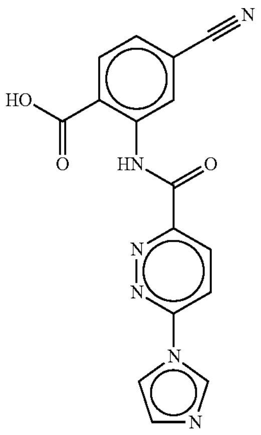
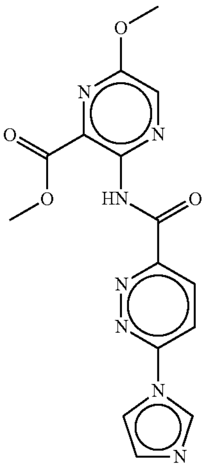
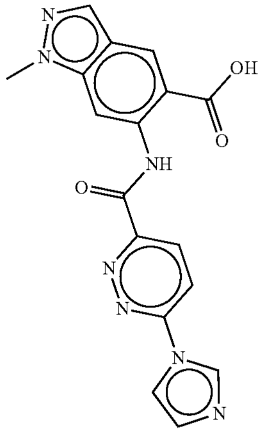
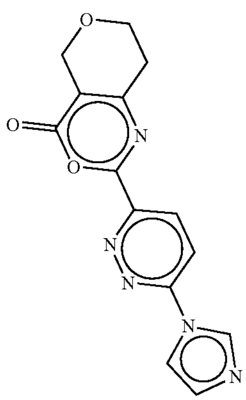
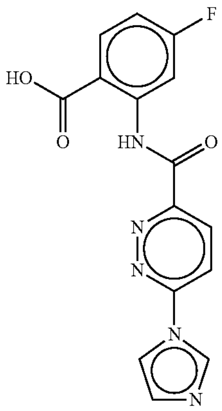

-continued
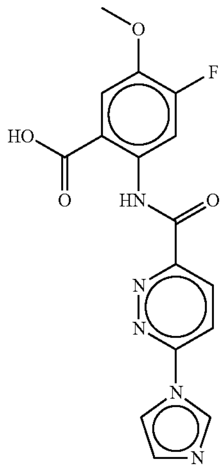
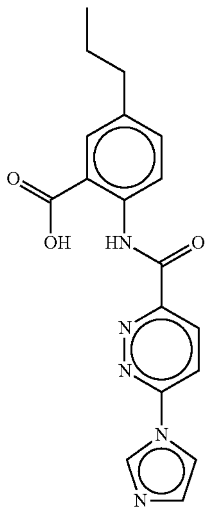
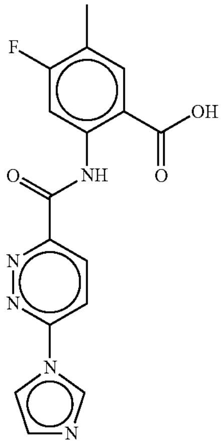
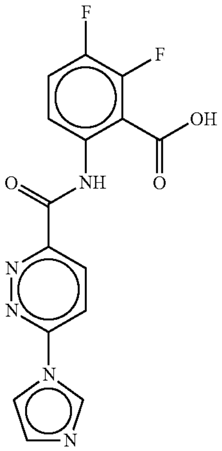
-continued
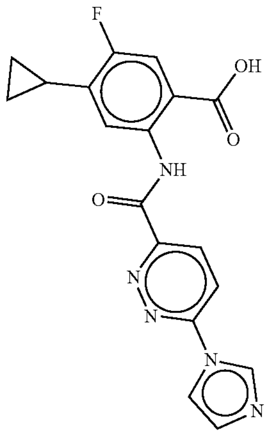
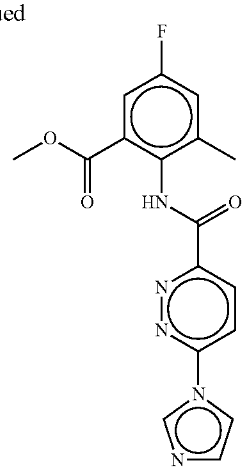
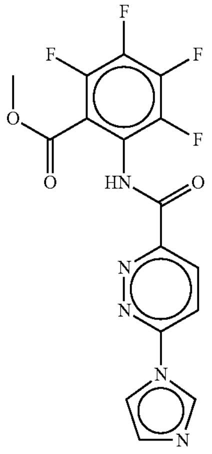
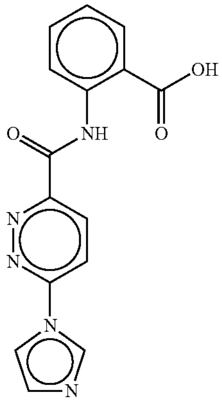
or a pharmaceutically acceptable salt thereof.
* * * * *